US012605464B2

(12) United States Patent
Cigler et al.

(10) Patent No.: US 12,605,464 B2
(45) Date of Patent: Apr. 21, 2026

(54) CYCLOHEXANE LIPIDOIDS FOR NUCLEIC ACID TRANSFECTION AND USE THEREOF

(71) Applicant: USTAV ORGANICKE CHEMIE A BIOCHEMIE AV CR V.V.I., Prague (CZ)

(72) Inventors: Petr Cigler, Prague (CZ); Klara Grantz Saskova, Prague (CZ); Vaclav Vanek, Prague (CZ); Zuzana Hejdankova, Prague (CZ); Lenka Loukotova, Praha-Lysolaje (CZ); Pavel Svec, Ceske Budejovice (CZ); Anastasiia Priss, Prague (CZ); Silvia Petrezselyova, Prague (CZ)

(73) Assignee: USTAV ORGANICKE CHEMIE A BIOCHEMIE AV CR, V.V.I., Prague (CZ)

( * ) Notice: Subject to any disclaimer, the term of this patent is extended or adjusted under 35 U.S.C. 154(b) by 180 days.

(21) Appl. No.: 18/579,456

(22) PCT Filed: Jul. 15, 2022

(86) PCT No.: PCT/CZ2022/050065

§ 371 (c)(1),
(2) Date: Jan. 15, 2024

(87) PCT Pub. No.: WO2023/001323

PCT Pub. Date: Jan. 26, 2023

(65) Prior Publication Data

US 2024/0335559 A1 Oct. 10, 2024

(30) Foreign Application Priority Data

Jul. 19, 2021 (CZ) .............................. PV 2021-345

(51) Int. Cl.
*A61K 48/00* (2006.01)
*A61K 8/42* (2006.01)
(Continued)

(52) U.S. Cl.
CPC ............ *A61K 48/0033* (2013.01); *A61K 8/42* (2013.01); *A61K 9/1271* (2013.01);
(Continued)

(58) Field of Classification Search
None
See application file for complete search history.

(56) References Cited

U.S. PATENT DOCUMENTS 3,452,082 A 6/1969 Peter
3,534,086 A 10/1970 Lakshmi
(Continued)

FOREIGN PATENT DOCUMENTS

CA 879102 A 8/1971
EP 3156077 A1 4/2017
(Continued)

OTHER PUBLICATIONS

International Search Report and Written Opinion for corresponding PCT application No. PCT/CZ2022/050065, mailed Dec. 2, 2022.
(Continued)

*Primary Examiner* — Bong-Sook Baek
(74) *Attorney, Agent, or Firm* — Riverside Law LLP

(57) ABSTRACT

A lipidoid of general formula I, where X is selected from —C(═O)NH—, —C(═O)O—, —C(═S)O—, —C(═O)S—, —C(═S)S—, —C(═O)NHNH—, —$CH_2$—, —O—, —OC(═O)—, —S—, —SC(═O)—, —NH—, —NHNH—, —NHC(═O)—, —NHNHC(═O)—, —C≡C—, —CH═CH—, a five-membered heterocycle containing at least 2 nitrogen atoms, —$CH_2$C(═O)NH—, —$CH_2$C(═S)O—, —$CH_2$C(═S)S—, —$CH_2$C(═O)
(Continued)

NHNH—, —N═CH—, —CH═N—, —NH—N═CH—, and —CH═N—NH—; Y is alkylene $C_2$-$C_{10}$ chain; $R^1$ is selected from alkyl $C_1$-$C_{46}$, alkenyl $C_2$-$C_{46}$, alkynyl $C_2$-$C_{46}$; Z is selected from H, —OH, —$CH_3$, —$CH_2OH$, —$NH_2$, —C(═O)$NH_2$, CONH$(CH_2)_2$OH, —CON$[(CH_2)_2OH]_2$, —CONHCH$(CH_2OH)_2$, —CONH$CH_2$CH(—OH)$CH_2$OH, —CONH$(CH_2)_2$C(═O)$NH_2$, —CON$[CH_2C(═O)NH_2]_2$, —CONH$(CH_2)_2$NHC(═O)$NH_2$, —CONH$(CH_2)_3$—N+$(CH_3)_2$—$(CH_2)_2$—$SO_3$—, —CONH$(CH_2)_3$—N+$(CH_3)_2$—$(CH_2)_2$—COO—, —COO(CH—COO$(CH_2)_2$—O—P(═O)(O—)—O$(CH_2)_2$—N+$(CH_3)_3$, —N+$(CH_3)_2$—$(CH_2)_3$—$SO_3$—, —N+$(CH_3)_2$—$(CH_2)_2$—COO—. Transfection reagents, transfection particles containing this lipidoid are also described.

21 Claims, 10 Drawing Sheets

Specification includes a Sequence Listing.

(51) Int. Cl.

| | |
|---|---|
| ***A61K 9/1271*** | (2025.01) |
| ***A61K 9/51*** | (2006.01) |
| ***C07C 233/62*** | (2006.01) |
| ***C07C 237/10*** | (2006.01) |
| ***C07D 207/12*** | (2006.01) |
| ***C07D 311/00*** | (2006.01) |
| ***C12N 15/88*** | (2006.01) |

(52) U.S. Cl.

CPC .......... *A61K 9/5123* (2013.01); *C07C 233/62* (2013.01); *C07C 237/10* (2013.01); *C07D 207/12* (2013.01); *C07D 311/00* (2013.01); *C12N 15/88* (2013.01); *C07C 2601/14* (2017.05)

(56) References Cited

U.S. PATENT DOCUMENTS

| | | | |
|---|---|---|---|
| 3,565,942 | A | 2/1971 | Krimmel |
| 3,573,312 | A | 3/1971 | Krimmel |
| 3,624,086 | A | 11/1971 | Krimmel |
| 3,625,985 | A | 12/1971 | Krimmel |
| 3,657,273 | A | 4/1972 | Krimmel |
| 3,663,565 | A | 5/1972 | Krimmel |
| 3,671,527 | A | 6/1972 | Krimmel |
| 3,682,922 | A | 8/1972 | Klimstra |
| 3,704,306 | A | 11/1972 | Krimmel |
| 3,705,141 | A | 12/1972 | Krimmel |
| 3,816,509 | A | 6/1974 | Krimmel |
| 4,448,972 | A | 5/1984 | Pfeiffer |
| 6,511,832 | B1 | 1/2003 | Guarino |
| 7,074,596 | B2 | 7/2006 | Darzynkiewicz |
| 7,288,262 | B1 | 10/2007 | Livoreil |
| 8,058,069 | B2 | 11/2011 | Yaworski |
| 8,323,686 | B2 | 12/2012 | Mirkin |
| 8,329,070 | B2 | 12/2012 | Maclachlan |
| 8,492,359 | B2 | 7/2013 | Yaworski |
| 8,598,333 | B2 | 12/2013 | Maclachlan |
| 8,822,668 | B2 | 9/2014 | Yaworski |
| 9,006,417 | B2 | 4/2015 | Yaworski |
| 9,216,155 | B2 | 12/2015 | Thaxton |
| 9,364,435 | B2 | 6/2016 | Yaworski |
| 9,404,127 | B2 | 8/2016 | Yaworski |
| 9,504,651 | B2 | 11/2016 | Maclachlan |
| 9,518,272 | B2 | 12/2016 | Yaworski |
| 9,668,980 | B2 | 6/2017 | Derosa |
| 9,687,448 | B2 | 6/2017 | Akinc |
| 9,872,900 | B2 | 1/2018 | Ciaramella |
| 9,877,919 | B2 | 1/2018 | Derosa |
| 9,878,042 | B2 | 1/2018 | Yaworski |
| 9,974,862 | B2 | 5/2018 | Nishikawa |
| 10,041,091 | B2 | 8/2018 | Cullis |
| 10,137,087 | B2 | 11/2018 | Derosa |
| 10,143,758 | B2 | 12/2018 | Guild |
| 10,201,499 | B2 | 2/2019 | Bell |
| 10,238,754 | B2 | 3/2019 | Guild |
| 10,238,756 | B2 | 3/2019 | Ho |
| 10,325,026 | B2 | 6/2019 | Cardillo |
| 10,369,122 | B2 | 8/2019 | Dong |
| 10,369,226 | B2 | 8/2019 | Maier |
| 10,471,153 | B2 | 11/2019 | Derosa |
| 10,487,332 | B2 | 11/2019 | Geall |
| 10,507,183 | B2 | 12/2019 | Guild |
| 10,626,393 | B2 | 4/2020 | Lee |
| 10,709,779 | B2 | 7/2020 | Ciaramella |
| 10,933,127 | B2 | 3/2021 | Ciaramella |
| 11,045,418 | B2 | 6/2021 | Hefesha |
| 11,141,378 | B2 | 10/2021 | Yaworski |
| 11,246,933 | B1 | 2/2022 | Maier |
| 11,291,682 | B2 | 4/2022 | Geall |
| 11,342,770 | B2 | 5/2022 | Liu |
| 11,357,726 | B2 | 6/2022 | Karve |
| 11,382,979 | B2 | 7/2022 | Maier |
| 11,395,799 | B2 | 7/2022 | Haas |
| 11,446,383 | B2 | 9/2022 | Yaworski |
| 11,471,525 | B2 | 10/2022 | Rauch |
| 11,524,023 | B2 | 12/2022 | Packer |
| 11,583,504 | B2 | 2/2023 | Brader |
| 11,590,229 | B2 | 2/2023 | Maier |
| 11,591,544 | B2 | 2/2023 | Drummond |
| 11,596,645 | B2 | 3/2023 | Geall |
| 11,612,657 | B2 | 3/2023 | Maier |
| 11,633,479 | B2 | 4/2023 | Maier |
| 11,633,480 | B2 | 4/2023 | Maier |
| 11,638,693 | B2 | 5/2023 | Geall |
| 11,638,694 | B2 | 5/2023 | Geall |
| 11,655,475 | B2 | 5/2023 | Geall |
| 11,666,534 | B2 | 6/2023 | Geall |
| 11,679,159 | B2 | 6/2023 | Anitha |
| 11,690,862 | B1 | 7/2023 | Geall |
| 11,707,482 | B2 | 7/2023 | Geall |
| 11,718,852 | B2 | 8/2023 | Yaworski |
| 11,766,401 | B2 | 9/2023 | Geall |
| 11,771,652 | B2 | 10/2023 | Casimiro |
| 11,786,467 | B2 | 10/2023 | Geall |
| 11,786,598 | B2 | 10/2023 | Yaworski |
| 11,839,686 | B2 | 12/2023 | Geall |
| 11,850,305 | B2 | 12/2023 | Geall |
| 11,857,681 | B2 | 1/2024 | Geall |
| 11,865,190 | B2 | 1/2024 | Leavitt |
| 11,883,534 | B2 | 1/2024 | Geall |
| 11,938,227 | B2 | 3/2024 | Bao |
| 11,951,177 | B2 | 4/2024 | An |
| 12,011,507 | B2 | 6/2024 | Kurek |
| 12,016,929 | B2 | 6/2024 | Yaworski |
| 12,059,498 | B2 | 8/2024 | Haas |
| 12,064,479 | B2 | 8/2024 | Drummond |
| 12,064,515 | B2 | 8/2024 | Karve |
| 12,077,725 | B2 | 9/2024 | Drummond |
| 2005/0245534 | A1 | 11/2005 | Link |
| 2012/0172411 | A1 | 7/2012 | Heyes |
| 2012/0295832 | A1 | 11/2012 | Constien |
| 2015/0018436 | A1 | 1/2015 | Drasar |
| 2016/0151284 | A1 | 6/2016 | Heyes |
| 2016/0256567 | A1 | 9/2016 | Heyes |
| 2016/0376224 | A1 | 12/2016 | Du |
| 2018/0043320 | A1 | 2/2018 | Ramsay |
| 2018/0147166 | A1 | 5/2018 | Dong et al. |
| 2018/0221510 | A1 | 8/2018 | Manoharan |
| 2018/0311176 | A1 | 11/2018 | Ozsolak |
| 2018/0311343 | A1 | 11/2018 | Huang |
| 2019/0002609 | A1 | 1/2019 | Klein |
| 2019/0032051 | A1 | 1/2019 | Yaworski |
| 2019/0076358 | A1 | 3/2019 | Ishihara |
| 2019/0106379 | A1 | 4/2019 | Heyes |
| 2019/0374466 | A1 | 12/2019 | Klein |
| 2020/0308603 | A1 | 10/2020 | Stewart |
| 2020/0330607 | A1 | 10/2020 | Dahlman |
| 2021/0059953 | A1 | 3/2021 | Kotin |

(56) References Cited

U.S. PATENT DOCUMENTS

| | | | | |
|---|---|---|---|---|
| 2021/0171521 | A1 | 6/2021 | Plewe | |
| 2021/0346306 | A1 | 11/2021 | Dimitrov | |
| 2021/0353556 | A1 | 11/2021 | Karve | |
| 2021/0378962 | A1 | 12/2021 | Karve | |
| 2021/0378980 | A1 | 12/2021 | Horhota | |
| 2022/0001025 | A1 | 1/2022 | Barz | |
| 2022/0016029 | A1 | 1/2022 | Karve | |
| 2022/0047519 | A1 | 2/2022 | Sagi | |
| 2022/0062175 | A1 | 3/2022 | Smith | |
| 2022/0071905 | A1 | 3/2022 | Karve | |
| 2022/0110884 | A1 | 4/2022 | Karve | |
| 2022/0133631 | A1 | 5/2022 | Shah | |
| 2022/0162552 | A1 | 5/2022 | Thomas | |
| 2022/0168222 | A1 | 6/2022 | Heyes | |
| 2022/0280427 | A1 | 9/2022 | Su | |
| 2022/0280639 | A1 | 9/2022 | Huang | |
| 2022/0287966 | A1 | 9/2022 | Karve | |
| 2022/0296517 | A1 | 9/2022 | Benenato | |
| 2022/0370624 | A1 | 11/2022 | Rajappan | |
| 2022/0381748 | A1 | 12/2022 | Haas | |
| 2022/0395589 | A1 | 12/2022 | Green | |
| 2022/0396548 | A1 | 12/2022 | Jain | |
| 2023/0000781 | A1 | 1/2023 | Derosa | |
| 2023/0097090 | A1 | 3/2023 | Tam | |
| 2023/0099898 | A1 | 3/2023 | Heinrich | |
| 2023/0159449 | A1 | 5/2023 | Perez-Garcia | |
| 2023/0241002 | A1 | 8/2023 | Smith | |
| 2023/0241223 | A1 | 8/2023 | Heinrich | |
| 2023/0265049 | A1* | 8/2023 | Cigler .................... | C12N 15/11 514/228.8 |
| 2023/0277457 | A1 | 9/2023 | Shepard | |
| 2023/0285297 | A1 | 9/2023 | Smith | |
| 2023/0285310 | A1 | 9/2023 | Cadete Pires | |
| 2023/0302153 | A1 | 9/2023 | An | |
| 2023/0364024 | A1 | 11/2023 | Brader | |
| 2023/0372537 | A1 | 11/2023 | Hope | |
| 2023/0398076 | A1 | 12/2023 | Karmali | |
| 2023/0398082 | A1 | 12/2023 | Kurek | |
| 2023/0414516 | A1 | 12/2023 | Bhatnagar | |
| 2023/0414747 | A1 | 12/2023 | Panzner | |
| 2024/0009131 | A1 | 1/2024 | Schariter | |
| 2024/0009238 | A1 | 1/2024 | Sahin | |
| 2024/0024422 | A1 | 1/2024 | Frederick | |
| 2024/0041785 | A1 | 2/2024 | Panzner | |
| 2024/0110214 | A1 | 4/2024 | Ziegenhals | |
| 2024/0123035 | A1 | 4/2024 | De Fougerolles | |
| 2024/0131193 | A1 | 4/2024 | De Fougerolles | |
| 2024/0148794 | A1 | 5/2024 | Alvarez | |
| 2024/0197636 | A1 | 6/2024 | Patil | |
| 2024/0216291 | A1 | 7/2024 | Van Der Meel | |
| 2024/0229034 | A1 | 7/2024 | Morris | |
| 2024/0238211 | A1 | 7/2024 | Brader | |
| 2024/0269323 | A1 | 8/2024 | Kulkarni | |

FOREIGN PATENT DOCUMENTS

| | | | |
|---|---|---|---|
| EP | 3192788 | A1 | 7/2017 |
| EP | 3604533 | A1 | 2/2020 |
| GB | 1310652 | A | 3/1973 |
| WO | 2008042973 | A2 | 4/2008 |
| WO | 2011071860 | A2 | 6/2011 |
| WO | 2011141705 | A1 | 11/2011 |
| WO | 2013086354 | A1 | 6/2013 |
| WO | 2013126803 | A1 | 8/2013 |
| WO | 2015199952 | A1 | 12/2015 |
| WO | 2015200465 | A1 | 12/2015 |
| WO | 2016187531 | A1 | 11/2016 |
| WO | 2017008076 | A1 | 1/2017 |
| WO | 2017019891 | A2 | 2/2017 |
| WO | 2017117528 | A1 | 7/2017 |
| WO | 2017176974 | A1 | 10/2017 |
| WO | 2018081480 | A1 | 5/2018 |
| WO | 2018087753 | A1 | 5/2018 |
| WO | 2018157009 | | 8/2018 |
| WO | 2019099501 | A1 | 5/2019 |
| WO | 2020070040 | A1 | 4/2020 |
| WO | 2020072324 | A1 | 4/2020 |
| WO | 2020077007 | A1 | 4/2020 |
| WO | 2020097520 | A1 | 5/2020 |
| WO | 2020097548 | A1 | 5/2020 |
| WO | 2020185293 | A1 | 9/2020 |
| WO | 2020227642 | A1 | 11/2020 |
| WO | 2020247604 | A1 | 12/2020 |
| WO | 2021021634 | A1 | 2/2021 |
| WO | 2021026358 | A1 | 2/2021 |
| WO | 2021113365 | A1 | 6/2021 |
| WO | 2022011156 | A1 | 1/2022 |
| WO | 2022063350 | A1 | 3/2022 |
| WO | 2022132926 | A1 | 6/2022 |
| WO | 2022159475 | A1 | 7/2022 |
| WO | 2022225918 | A1 | 10/2022 |
| WO | 2022251953 | A1 | 12/2022 |
| WO | 2022251959 | A1 | 12/2022 |
| WO | 2023001323 | A1 | 1/2023 |
| WO | 2023009421 | A1 | 2/2023 |
| WO | 2023009422 | A1 | 2/2023 |
| WO | 2023021427 | A1 | 2/2023 |
| WO | 2023031392 | A1 | 3/2023 |
| WO | 2023043038 | A1 | 3/2023 |
| WO | 2023205628 | A1 | 10/2023 |
| WO | 2023220815 | A1 | 11/2023 |
| WO | 2023239756 | A1 | 12/2023 |
| WO | 2024006863 | A1 | 1/2024 |
| WO | 2024026475 | A1 | 2/2024 |
| WO | 2024086929 | A1 | 5/2024 |
| WO | 2024119276 | A1 | 6/2024 |
| WO | 2024133635 | A1 | 6/2024 |
| WO | 2024136626 | A1 | 6/2024 |

OTHER PUBLICATIONS

International Application Status Report for corresponding PCT application No. PCT/CZ2022/05006, downloaded Nov. 27, 2023.
Grillaud Maxime et al, "Polycationic Adamantane-Based Dendrons of Different Generations Display High Cellular Uptake without Triggering Cytotoxicity", Journal of the American Chemical Society, vol. 136, No. 2, Jan. 3, 2014 (Jan. 3, 2014), p. 810-819, XP055842774.

* cited by examiner

1 2 3 4 5 6 7

8

9

10

11

37 38 39 43 44

39 40 41 42

53

54

55

56

B40 B45

CYCLOHEXANE LIPIDOIDS FOR NUCLEIC ACID TRANSFECTION AND USE THEREOF

FIELD OF ART

The invention relates to novel ionizable lipidoids and to the use of these compounds for the transfection and administration of nucleotides and nucleic acids and their synthetic analogues into cells and tissues.

BACKGROUND ART

The development of nucleic acid (NA)-based therapies has experienced an unprecedented renaissance in recent years. Due to the high efficacy and at the same time the low risk of adverse side effects compared to previously tested therapeutic deoxyribonucleic acids (DNA), ribonucleic acid (RNA) therapies are now gaining ground. Several such drugs have already reached clinical use, for example patisiran for hereditary transthyretin amyloidosis, eteplirsen for certain types of Duchenne muscular dystrophy, or nusinersen for the treatment of spinal muscular atrophy. All of these diseases are life-threatening and there is no alternative treatment for them. Potential drugs targeting ribonucleic acid (RNA) or its use can be divided into three categories based on whether they target NA or proteins or encode proteins. The first category includes single-stranded antisense oligonucleotides of 13-25 nucleotides (nt) that block the translation of messenger RNA (mRNA) or RNA splicing (nusinersen, eteplirsen); and small interfering RNAs (siRNA, 21-23nt) that degrade mRNA (patisiran). Therapeutic RNA molecules that target proteins use a type of molecule known as an RNA aptamer. It is designed to modulate the function of a particular protein. An example of such a drug is pegaptanib, used to treat neovascular age-related macular degeneration, which was the first drug approved of its kind in 2004. Therapies utilising mRNA are mainly used for the preparation of so-called personalized vaccines against cancer or vaccines against infectious diseases (e.g., Zika virus). In viral diseases, candidates for a prophylactic vaccine based on mRNA against rabies and pandemic influenza have been shown to induce safe antibody production in healthy volunteers. Protein-replacing mRNA therapies are also in the preclinical stages of development, for example, for the treatment of hemophilia.

Molecular technologies enabling direct genome editing, especially those based on the CRISPR-Cas9 system, are now booming. CRISPR technology is a tool that allows to change DNA sequences and modify gene function. Potential applications include the repair of genetic defects, the treatment and prevention of the spread of diseases or the improvement of agricultural crops. The CRISPR-Cas9 system has been tested in a number of preclinical and clinical studies, including HIV treatment, treatment of hematological malignancies, and genetic disorders, including sickle cell disease and β-thalassemia. RNA editing is then enabled by the ADAR system (adenosine deaminase acting on RNA), which so far seems to be safer from a clinical point of view. Molecular technologies for direct genome editing can be delivered to the site of action in the form of mRNA that encodes the appropriate enzyme responsible for editing.

A key factor enabling the safe use of all these technologies (or others, based on NA) is their safe and efficient transport to the site of action. The critical step is the penetration of negatively charged NAs through the phospholipid membrane of the cell; the process of deliberately introducing NAs into eukaryotic cells is called transfection. In recent decades, there has been an intensive development of carriers (so-called vectors) to efficiently transport NAs across the cell membrane while protecting the NAs from degradation in vivo (Stewart, M. P.: *Chem. Rev.* 2018, 118, 7409-7531).

Both viral and non-viral (physical, chemical) vectors are used for NA transfection. Although approximately 70% of clinical trials in the field of gene therapy have so far been performed using viral vectors, this approach carries numerous risks (carcinogenicity, induction of an immune response, tissue nonspecificity, limited NA incorporation capacity, and manufacturing complexity). Physical methods (e.g., electroporation) are difficult to use systemically in human medicine.

In contrast, synthetic chemical vectors usually have lower immunogenicity, are able to transport larger amounts of genetic material, and because they are composed of well-defined molecules, their structure can be adjusted as needed to increase their efficiency and suppress toxicity. Cationic polymers or cationic lipids are used as chemical vectors, which form a complex with negatively charged NAs. This complex can penetrate the cell membrane and at the same time protects NAs from degradation in the extracellular environment.

From a structural point of view, so-called lipid nanoparticles (LNPs) are currently the most promising and clinically advanced form of these complexes. In them, cationic lipids are usually formulated with a PEGylated lipid that prevents aggregation, affects particle size and transfection efficiency, with a helper lipid and cholesterol, which are necessary for stable NA encapsulation, as shown, for example, in an siRNA transfection system (Kulkarni, J.: *Nanoscale,* 2019, 11, 21733-21739). LNPs can accommodate NA molecules ranging in size from a few nucleotide units to millions.

Synthetic cationic lipids and lipidoids (synthetic molecules similar to lipids that differ in a larger number of hydrophobic chains) are formed by a cationic and a hydrophobic domain. To date, a large number of these substances have been developed with high structural variability in both domains, both by targeted design and by testing combinatorially generated libraries.

Lipids and lipidoids such as D-Lin-MC3-DMA, C12-200, cKK-E12, SA2-SC8 and others have been specially developed for siRNA transfection (Dong, Y.: *Adv. Drug Deliv. Rev.* 2019, 144, 133-147). A formulation containing D-Lin-MC3-DMA was recently (August 2018) introduced into clinical practice under the name Onpattro (formerly Patisiran), making it the first approved siRNA drug in history (Zhang, X.: *J Clin. Pharmacol.* 2020, 60 (1), 37-49). However, formulations developed for siRNA may not be effective for mRNA, and therefore, targeted optimization is necessary (Cullis, P.: *Mol. Ther.* 2017, 25 (7), 1467-1475).

Ionizable lipids and lipidoids such as D-Lin-MC3-DMA, C12-200, cKK-E12, and TT3 are used to transfect mRNA (Zhong, Z.: *Nano Today* 2018, 23, 16-39; Kowalski, P.: *Mol. Ther.* 2019, 27 (4), 1-19; Li, B.: *Nano Lett.* 2015, 15, 8099-8107). Ionizable lipids are also used for DNA transfection. Again, it should be emphasized that transfection systems optimized for small-molecule (siRNA) transfection are not always suitable for DNA transfection, and even formulations developed for mRNA may not be effective for DNA (Buck, J.: *ACS Nano* 2019, 13, 3754-3782).

Because, despite their enormous therapeutic potential, very few synthetic vectors based on ionizable lipids have been brought to the stage of clinical use so far, it is necessary to develop new systems with higher efficiency and also with very low in vivo toxicity.

DISCLOSURE OF THE INVENTION

The present invention provides a solution to the problem of the efficiency of transfection and targeted delivery of nucleotides and nucleic acids and their synthetic analogs using ionizable (cationic) lipids and the problem of the toxicity of these lipids to the target organism or cell. We have surprisingly found that, if cyclohexane is used as the central core of the ionizable lipidoid, the transfection efficiency of such lipidoids is significantly increased in comparison to previously known solutions. At the same time, these cyclohexane-containing lipidoids exhibit extremely low cytotoxicity at relevant doses. Specific properties of the cyclohexane core, which is used as the central structural motif of the new ionizable lipidoids, are steric complexity in its vicinity and a wide range of substitutions in comparison to the ionizable lipids and lipidoids known so far.

The object of the present invention are ionizable lipidoids of general formula I (I)

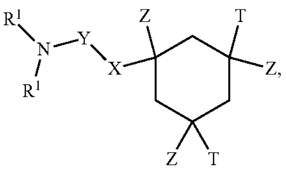

wherein

X is selected from a group comprising —C(═O)NH—, —C(═O)O—, —C(═S)O—, —C(═O)S—, —C(═S)S—, —C(═O)NHNH—, $—CH_2—$, —O—, —OC(═O)—, —S—, —SC(═O)—, —NH—, —NHNH—, —NHC(═O)—, —NHNHC(═O)—, —C≡C—, —CH═CH—, a five-membered heterocycle containing at least 2 nitrogen atoms, $—CH_2C(═O)NH—$, $—CH_2C(═O)O—$, $—CH_2C(═S)O—$, $—CH_2C(═S)S—$, $—CH_2C(═O)NHNH—$, —N═CH—, —CH═N—, —NH—N═CH—, and —CH═N—NH—;

Y is selected from a group comprising alkylene $C_2$-$C_{10}$ chains, wherein in the said alkylene chain, one or more $—CH_2—$ groups may optionally be replaced with one or more O and/or S atoms; preferably, Y is selected from a group comprising alkylene $C_2$-$C_{10}$ chains, in particular alkylene $C_3$-$C_6$ chains, preferably propylene ($—(CH_2)_3—$), pentylene ($—(CH_2)_5—$), hexylene ($—(CH_2)_6—$);

$R^1$ are the same or different from each other, each $R^1$ being independently selected from the group comprising alkyl $C_1$-$C_{46}$, alkenyl $C_2$-$C_{46}$, alkynyl $C_2$-$C_{46}$, wherein said alkyl, alkenyl or alkynyl may be linear or branched, and wherein in the said alkyl, alkenyl or alkynyl, one or more $—CH_2—$ groups may optionally be replaced with one or more groups selected from —CH(OH)—, —OC(═O)—, —C(═O)O—, —S—S—, —C(═O)NH—, —NHC(═O)—, —O—, and —S—;

wherein if said alkyl, alkenyl or alkynyl is branched, then one or more >CH— groups may optionally be replaced with >C(OH)—;

and wherein if $R^1$ is alkyl $C_1$-$C_4$, then one hydrogen from the terminal $—CH_3$ group may be substituted with Z;

with the proviso that at least one $R^1$ contains at least 8 carbon atoms, preferably at least 10 carbon atoms, more preferably at least 12 carbon atoms; more preferably, at least two $R^1$ substituents contain at least 8 carbon atoms, preferably at least 10 carbon atoms, more preferably at least 12 carbon atoms;

Z are the same or different from each other, each Z being independently selected from the group comprising hydrogen, —OH, $—CH_3$, $—CH_2OH$, $—NH_2$, $—C(═O)NH_2$, $—CONH(CH_2)_2OH$, $—CON[(CH_2)_2OH]_2$, $—CONHCH(CH_2OH)_2$, $—CONHCH_2CH(—OH)CH_2OH$, $—CONH(CH_2)_2C(═O)NH_2$, $—CON[CH_2C(═O)NH_2]_2$, $—CONHCH[C(═O)NH_2]_2$, $—CONH(CH_2)_2NHC(═O)NH_2$, $—CONH(CH_2)_3—N^+(CH_3)_2—(CH_2)_2—SO_3—$, $—CONH(CH_2)_3—N^+(CH_3)_2—(CH_2)_3—SO_3—$, $—CONH(CH_2)_3—N^+(CH_3)_2—(CH_2)_2—COO^-$, $—COO(CH_2)_2—O—P(═O)(O—)—O(CH_2)_2—N+(CH_3)_3$, $—N+(CH_3)_2—(CH_2)_3—SO_3—$, $—N+(CH_3)_2—(CH_2)_2—COO^-$,

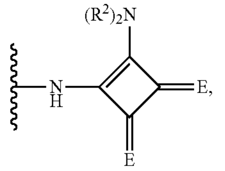

and

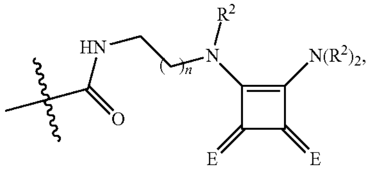

wherein $R^2$ is independently selected from hydrogen and $—CH_3$;

E is independently selected from O and S atoms;

n is an integer within the range of from 1 to 5;

and T are the same or different from each other, each T being independently selected from the group comprising $—X—Y—N(R^1)_2$, $—C(═O)O(C_1$-$C_3$ alkyl), $—C(═O)OCH_2CH_2OH$, $—C(═O)NH_2$,

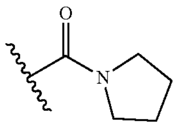

, $—C(═O)OH$, $—CONH(CH_2)_2OH$, $—CON[(CH_2)_2OH]_2$, $—CONHCH(CH_2OH)_2$, $—CONHCH_2CH(—OH)CH_2OH$, $—CONH(CH_2)_2C(═O)NH_2$, $—CON[CH_2C(═O)NH_2]_2$, $—CONHCH[C(═O)NH_2]_2$, $—CONH(CH_2)_2NHC(═O)NH_2$, $—CONH(CH_2)_3—N+(CH_3)_2—(CH_2)_2—SO_3—$, $—CONH(CH_2)_3—N+(CH_3)_2—(CH_2)_3—SO_3$, $—CONH(CH_2)_3—N+(CH_3)_2—(CH_2)_2—COO^-$, $—COO(CH_2)_2—O—P(═O)(O—)—O(CH_2)_2—N^+(CH_3)_3$,

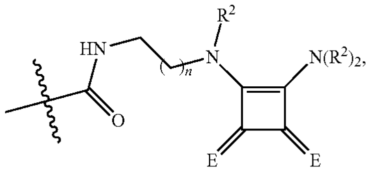

—OH, —O($C_1$-$C_3$ alkyl), —$NH_2$, —NHC(=O)$CH_3$, —NHS(=O)$_2$$CH_3$, —NHC(=O)N($CH_3$)$_2$, —NHC(=O)NH($CH_3$), —NHC(=S)N($CH_3$)$_2$, —NHC(=S)NH($CH_3$), —NHC(=N—CN)$NH_2$, —NHC(=N—CN)NH($CH_3$), —NHC(=N—CN)N($CH_3$)$_2$, —NHC[=N—S(=O)$_2$$NH_2$]$NH_2$,

—$N^+$($CH_3$)$_2$—($CH_2$)$_3$—$SO_3$—, —$N^+$($CH_3$)$_2$—($CH_2$)$_2$—$COO^-$

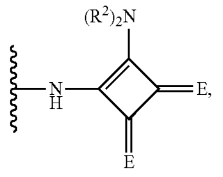

wherein $R^2$, E and n are as defined above;

and/or if Z is —OH or —$CH_2$OH, and T is —C(=O)OH, then Z together with T and three carbon atoms between them may form a cyclic lactone containing 4 to 5 carbon atoms. The invention also encompasses the pharmaceutically acceptable salts, addition salts and solvates of the above defined lipidoids.

The term "alkyl" means a saturated hydrocarbon chain, which may be straight, branched or cyclic or cycle-containing, and which is derived from an alkane by removal of one hydrogen atom.

The term "alkenyl" means a hydrocarbon chain containing at least one double bond between carbon atoms, and which is derived from an alkene by removal of one hydrogen atom. The hydrocarbon chain may be straight, branched or cyclic or cycle-containing.

The term "alkynyl" means a hydrocarbon chain containing at least one triple bond between carbon atoms, and optionally also one or more double bonds between carbon atoms, and which is derived from an alkyne by removal of one hydrogen atom. The hydrocarbon chain may be straight, branched or cyclic or cycle-containing.

The term "alkylene" means a bivalent saturated hydrocarbon chain, which may be linear, branched, cyclic or cycle-containing, preferably it is linear. The chain has two valencies, i.e. it is derived from an alkane by removal of two hydrogen atoms from different carbon atoms, and it binds as a linker or bridge via two single bonds.

The terms "branched alkyl", "branched alkenyl", "branched alkynyl" mean an alkyl, alkenyl or alkynyl comprising from one to five branches (hydrocarbon chains) attached to the main hydrocarbon chain.

When the molecule of general formula I has a positive charge, the compound includes a counterion, which may be a pharmaceutically acceptable anion of an organic or inorganic acid, to form a pharmaceutically acceptable salt. Such an anion may be selected, for example, from the group comprising acetate, aspartate, benzesulphonate, benzoate, besylate, bicarbonate, bitartrate, bromide, camsylate, carbonate, chloride, citrate, decanoate, edetate, esylate, fumarate, gluceptate, gluconate, glutamate, glycolate, hexanoate, iodide, lactate, malate, maleate, mandelate, mesylate, methanesulphate, napsylate, nitrate, octanoate, oleate, palmoate, pantothenate, phosphate, polygalacturonate, propionate, salicylate, stearate, succinate, sulphate, tartrate, and tosylate.

When the compound of formula I contains chiral centers, then the formula I includes pure enantiomers as well as mixtures of enantiomers, including the racemate. Formula I includes compounds of formula I in free form, as well as in the form of salts, addition salts (with acids or bases) and/or solvates, including hydrates or alcohol solvates.

In one embodiment, X is selected from a group consisting of —C(=O)NH—, —C(=O)O—, —C(=O)NHNH—, —OC(=O)—, —O—, —NHC(=O)—, —NHNHC(=O)—, and a five-membered heterocycle containing at least 2 nitrogen atoms. Preferably X is —C(=O)NH— or —NHC(=O)—.

The $R^1$ chains may be the same within the whole molecule or different from each other or $R^1$ chains are the same for one nitrogen atom but not within the whole molecule. Preferably $R^1$ chains are the same within the whole molecule, or all nitrogen atoms are substituted identically (either with two identical $R^1$ or with two different $R^1$), for synthetic simplicity. At least one $R^1$ substituent is fatty chain of at least 8 carbon atoms, and $R^1$ are selected from the group comprising alkyl $C_1$-$C_{46}$, alkenyl $C_2$-$C_{46}$, alkynyl $C_2$-$C_{46}$, wherein said alkyl, alkenyl or alkynyl may be linear or branched, and wherein in the said alkyl, alkenyl or alkynyl, one or more —$CH_2$— groups may optionally be replaced with one or more groups selected from —CH(OH)—, —OC(=O)—, —C(=O)O—, —S—S—, —C(=O)NH—, —NHC(=O)—, —O—, and —S—; wherein if said alkyl, alkenyl or alkynyl is branched, then one or more >CH— groups may optionally be replaced with >C(OH)—;

wherein if $R^1$ is alkyl $C_1$-$C_4$, then one hydrogen from the terminal —$CH_3$ group may be substituted with Z.

In one embodiment, $R^1$ are independently selected from the group comprising alkyl $C_1$-$C_{46}$, and alkenyl $C_2$-$C_{46}$, wherein in the said alkyl or alkenyl, one or more —$CH_2$— groups may optionally be replaced with one or more groups selected from —CH(OH)—, —OC(=O)—, —C(=O)O—.

Preferably, $R^1$ are independently selected from the group comprising linear or branched alkyl $C_8$-$C_{20}$, and linear or branched alkenyl $C_8$-$C_{20}$, wherein in the said alkyl or alkenyl, one or more —$CH_2$— groups may optionally be replaced with one or more groups selected from —OC(=O)—, —C(=O)O—. More preferably, $R^1$ is selected from the group comprising linear or branched alkyl $C_{10}$-$C_{15}$, which may optionally be replaced with one or more groups selected from —OC(=O)—, —C(=O)O—; and linear or branched alkenyl C12-Cis, which may optionally be replaced with one or more groups selected from —OC(=O)—, —C(=O)O—.

Preferably, alkenyl chain contains from one to five carbon-carbon double bonds.

In one embodiment, all $R^1$ in the molecule are the same.

In one embodiment, each nitrogen atom in the molecule, bearing $R^1$ groups, is substituted identically by two identical $R^1$ (but $R^1$ bound to different nitrogen atoms within the same lipidoid structure may not be identical).

In one embodiment, two different $R^1$ are bound to one nitrogen atom.

At least one $R^1$ in the lipidoid structure must contain at least 8 carbon atoms, preferably at least 10 carbon atoms, more preferably at least 12 carbon atoms in order to enable for the lipid-like properties of the molecule. Preferably, two $R^1$ in the lipidoid structure contain at least 8 carbon atoms, preferably at least 10 carbon atoms, more preferably at least 12 carbon atoms.

In one embodiment, one substituent T is —X—Y—N($R^1$)$_2$.

In another embodiment, both substituents T are —X—Y—N($R^1$)$_2$.

In the latter case, the resulting molecule of the lipidoid has a general formula II (II)

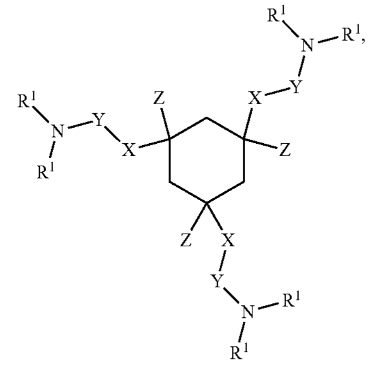

wherein X, Y, Z and $R^1$ are as defined above.

The structure of the general formula II preferably has the following substituents:

X is selected from a group comprising —C(═O)NH—, —C(═O)O—, —C(═S)O—, —C(═O)S—, —C(═S)S—, —C(═O)NHNH—, —$CH_2$—, —O—, —OC(═O)—, —S—, —SC(═O)—, —NH—, —NHNH—, —NHC(═O)—, —NHNHC(═O)—, —C≡C—, —CH═CH—, a five-membered heterocycle containing at least 2 nitrogen atoms, —$CH_2$C(═O)NH—, —$CH_2$C(═O)O—, —$CH_2$C(═S)O—, —$CH_2$C(═S)S—, —$CH_2$C(═O)NHNH—, —N═CH—, —CH═N—;

Y is an alkylene chain $C_2$-$C_{10}$, wherein one or more —$CH_2$— groups may optionally be replaced with one or more O and/or S atoms;

Z are the same or different from each other, each Z being selected from the group consisting of hydrogen atom, —OH, —$CH_3$, —$CH_2$OH, —$NH_2$, —C(═O)$NH_2$, —CONH$(CH_2)_2$OH, —CON[$(CH_2)_2$OH]$_2$, —CONHCH$(CH_2OH)_2$, —CONH$CH_2$CH(—OH)$CH_2$OH, —CONH$(CH_2)_2$C(═O)$NH_2$, —CON[$CH_2$C(═O)$NH_2$]$_2$, —CONHCH[C(═O)$NH_2$]$_2$, —CONH$(CH_2)_2$NHC(═O)$NH_2$, —$N^+(CH_3)_2$—$(CH_2)_3$—$SO_3$—, —$N^+(CH_3)_2$—$(CH_2)_2$—$COO^-$

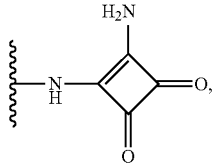

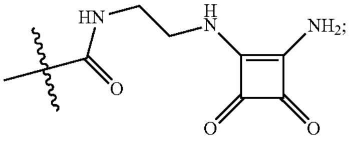

and $R^1$ are the same or different from each other, each $R^1$ being selected from the group consisting of alkyl $C_8$-$C_{20}$, alkenyl $C_8$-$C_{20}$, alkynyl $C_8$-$C_{20}$, wherein in the said alkyl, alkenyl or alkynyl, one or more —$CH_2$— groups may optionally be replaced with one or more groups selected from —CH(OH)—, —OC(═O)—, —C(═O)O—, —S—S—, —C(═O)NH—, —NHC(═O)—, —O—, —S—.

The linker X is formed by a reaction of attachment of the amine moieties of the molecule to the central cyclohexane core. These may therefore be different linkers, depending on the reaction chosen, e.g. the formation of ester, amide and their analogues, via click reaction (e.g. azido-alkyne cycloaddition), etc. X is thus selected from the group comprising —C(═O)NH—, —C(═O)O—, —C(═S)O—, —C(═O)S—, —C(═S)S—, —C(═O)NHNH—, —$CH_2$—, —O—, —OC(═O)—, —S—, —SC(═O)—, —NH—, —NHNH—, —NHC(═O)—, —NHNHC(═O)—, —C≡C—, —CH═CH—, a five-membered heterocycle containing at least 2 nitrogen atoms, —$CH_2$C(═O)NH—, —$CH_2$C(═O)O—, —$CH_2$C(═S)O—, —$CH_2$C(═S)S—, —$CH_2$C(═O)NHNH—, —N═CH—, —CH═N—, —NH—N═CH—, and —CH═N—NH—. Preferably, X is selected from —C(═O)NH—, —NHC(═O)—, a five-membered heterocycle containing at least 2 nitrogen atoms, —OC(═O)—, and —C(═O)O—.

The linker Y is an alkylene chain providing at least a minimum distance of the amine from the linker X and the cyclohexane core. Y is a $C_2$-$C_{10}$ alkylene chain, preferably a $C_2$-$C_5$ alkylene chain, wherein one or more —$CH_2$— groups may optionally be replaced with one or more O and/or S atoms.

The substituent Z may further modify the properties of the compound of formula I and II.

In one embodiment, Z is selected from the group consisting of hydrogen, —OH, —$CH_3$, —$CH_2$OH, —$NH_2$, —C(═O)$NH_2$, —CONH$(CH_2)_2$OH, —CON[$(CH_2)_2$OH]$_2$, —CONHCH$(CH_2OH)_2$, —CONH$CH_2$CH(—OH)$CH_2$OH, —CONH$(CH_2)_2$C(═O)$NH_2$, —CON[$CH_2$C(═O)$NH_2$]$_2$, —CONHCH[C(═O)$NH_2$]$_2$, —CONH$(CH_2)_2$NHC(═O)$NH_2$, —$N^+(CH_3)_2$—$(CH_2)_3$—$SO_3^-$, —$N^+(CH_3)_2$—$(CH_2)_2$—$COO^-$,

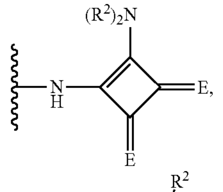

and

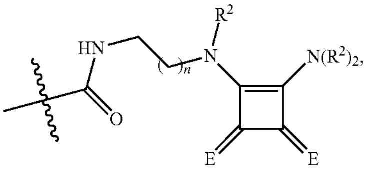

wherein $R^2$, E and n are as defined above. Preferably Z is H, —$CH_3$, —$CH_2$OH, or if Z is —OH or —$CH_2$OH, and T is —C(═O)OH, then Z together with T and three carbon atoms between them may form a cyclic lactone containing 4 to 5 carbon atoms.

The substituent T may further modify the properties of the compound of formula I and II. In one embodiment, T is selected from the group consisting of —X—Y—N$(R^1)_2$, —C(═O)O($C_1$-$C_3$ alkyl),

—C(═O)O$CH_2CH_2$OH, —C(═O)$NH_2$,

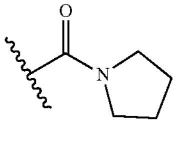

,

—C(═O)OH, —CONH$(CH_2)_2$OH, —CON$[(CH_2)_2OH]_2$, —CONHCH$(CH_2OH)_2$, —CONH$CH_2$CH(—OH)$CH_2$OH, —CONH$(CH_2)_2$C(═O)$NH_2$, —CON$[CH_2C(═O)NH_2]_2$, —CONHCH$[C(═O)NH_2]_2$, —CONH$(CH_2)_2$NHC(═O)$NH_2$, —CONH$(CH_2)_3$—$N^+(CH_3)_2$—$(CH_2)_2$—$SO_3$—, —CONH$(CH_2)_3$—$N^+(CH_3)_2$—$(CH_2)_3$—$SO_3$—, —CONH$(CH_2)_3$—$N^+(CH_3)_2$—$(CH_2)_2$—$COO^-$,

—COO$(CH_2)_2$—O—P(═O)(O—)—O$(CH_2)_2$—$N^+(CH_3)_3$,

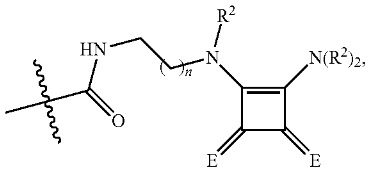

wherein $R^2$, E and n are as defined above. More preferably, T is selected from the group consisting of —X—Y—N$(R^1)_2$, —C(═O)O($C_1$-$C_3$ alkyl),

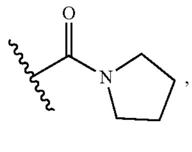 [SMILES: *C(=O)N1CCCC1],

—C(═O)OH. Most preferably, T is selected from the group consisting of —X—Y—N$(R')_2$, —C(═O)$OCH_3$

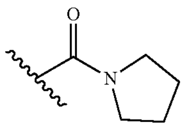,

—C(═O)OH.

In one specific embodiment, the lipidoid of formula I has Z selected from the group consisting of hydrogen, —OH, —$CH_3$, —$CH_2$OH;

and T selected from the group consisting of —X—Y—N$(R^1)_2$, —C(═O)O($C_1$-$C_3$ alkyl),

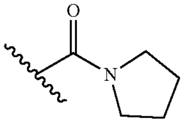,

—C(═O)OH;

and/or if Z is —OH or —$CH_2$OH, and T is —C(═O)OH, then Z together with T and three carbon atoms between them may form a cyclic lactone containing 4 to 5 carbon atoms. Preferably, lipidoid of formula I has the following substituents:

X is —C(═O)NH— or —NHC(═O)—;

Y is selected from —$(CH_2)_3$—, —$(CH_2)_4$—, —$(CH_2)_5$—, and —$(CH_2)_6$—;

$R^1$ is selected from the group comprising linear or branched alkyl $C_{10}$-$C_{15}$, which may optionally be replaced with one or more groups selected from —OC(═O)—, —C(═O)O—; and linear or branched alkenyl $C_{12}$-$C_{18}$, which may optionally be replaced with one or more groups selected from —OC(═O)—, —C(═O)O—;

T is selected from —X—Y—N$(R^1)_2$, —C(═O)$OCH_3$,

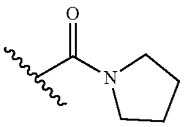, and —C(═O)OH;

Z is selected from H, —$CH_3$, and —$CH_2$OH.

Specifically, the following lipidoids are preferred:

cis,cis-N',N[3],N[5]-Tris(6-(didodecylamino)hexyl)cyclohexane-1,3,5-tricarboxamide (3);

cis,cis-N',N[3],N[5]-Tris(6-(di((hexyloxycarbonyl)butyl)amino)hexyl)cyclohexane-1,3,5-tricarboxamide (7);

cis,cis-N',N[3],N[5]-Tris(6-(didodecylamino)hexyl)-1,3,5-trimethylcyclohexane-1,3,5-tricarboxamide (8);

cis,cis-N',N[3],N[5]-Tris(3-(didodecylamino)propyl)-1,3,5-trimethylcyclohexane-1,3,5-tricarboxamide (11);

cis,cis-N',N[3],N[5]-Tris(6-(di((9Z,12Z)-octadeca-9,12-dien-1-yl)amino)hexyl)-1,3,5-trimethylcyclohexane-1,3,5-tricarboxamide (15);

Hexa(octan-2-yl) cis,cis-6,6',6",6'",6"",6'""-((((cyclohexane-1,3,5-tricarbonyl)tris(azanediyl))tris(hexane-6,1-diyl))tris(azanetriyl))hexahexanoate (19);

Hexakis(3-methylhexyl) cis,cis-7,7',7",7'",7" ",7'""-((((cyclohexane-1,3,5-tricar-bonyl)tris(azanediyl))tris(hexane-6,1-diyl))tris(azanetriyl))hexaheptanoate (23);

Hexakis((E)-3,7-dimethylocta-2,6-dien-1-yl) cis,cis-5,5',5",5'",5" ",5'""-((((cyclohexane-1,3,5-tricar-bonyl)tris(azanediyl))tris(hexane-6,1-diyl))tris(azanetriyl))hexapentanoate (27);

Hexakis((Z)-3,7-dimethylocta-2,6-dien-1-yl) cis,cis-5,5',5",5'",5" ",5'""-((((cyclohexane-1,3,5-tricar-bonyl)tris(azanediyl))tris(hexane-6,1-diyl))tris(azanetriyl))hexapentanoate (31);

Tetra(octan-2-yl) cis,cis-6,6',6",6'"-((((5-(methoxycarbonyl)cyclohexane-1,3-dicar-bonyl)bis(azanediyl))bis(hexane-6,1-diyl))bis(azanetriyl))tetrahexanoate (32);

Tetrakis(3-methylhexyl) cis,cis-7,7',7",7'"-((((5-(methoxycarbonyl)cyclohexane-1,3-dicar-bonyl)bis(azanediyl))bis(hexane-6,1-diyl))bis(azanetriyl))tetraheptanoate (33);

cis,cis-3,5-Bis((6-(bis(6-(octan-2-yloxy)-6-oxohexyl)amino)hexyl)carbamoyl)cyclohexane-1-carboxylic acid (35);

Tetra(octan-2-yl) cis,cis-6,6',6",6'"-((((5-(pyrrolidine-1-carbonyl)cyclohexane-1,3-dicar-bonyl)bis(azanediyl))bis(hexane-6,1-diyl))bis(azanetriyl))tetrahexanoate (36);

Hexakis(3-methylhexyl) cis,cis-7,7',7",7'",7" ",7'""-((((1,3,5-trimethylcyclohexane-1,3,5-tricar-bonyl)tris(azanediyl))tris(hexane-6,1-diyl))tris(azanetriyl))hexaheptanoate (40);

cis,cis-6,6',6",6'",6"",6'""-((((1,3,5-Trimethylcyclohexane-1,3,5-tricarbonyl)tris(azanediyl))tris(hexane-6,1-diyl))tris(azanetriyl))hexahexanoate (41);

cis,cis-3,5-Bis((6-(bis(6-(octan-2-yloxy)-6-oxohexyl)amino)hexyl)carbamoyl)-1,3,5-trimethylcyclohex-ane-1-carboxylic acid (42);

Tetra(octan-2-yl) cis,cis-6,6',6",6'"-((((1,3,5-tris((benzyloxy)methyl)-5-(bis(6-(octan-2-yloxy)-6-oxohexyl)carbamoyl)cyclohexane-1,3-dicarbonyl)bis(azanediyl))bis(hexane-6,1-diyl))bis(azanetriyl))tetrahexanoate (45);

cis,cis-1,3,5-Tris((benzyloxy)methyl)-3,5-bis((6-(bis(6-(octan-2-yloxy)-6-oxohexyl)amino)hexyl)car-bamoyl)cyclohexane-1-carboxylic acid (46);

Hexa(octan-2-yl) cis,cis-6,6',6'',6''',6'''',6'''''-((((1,3,5-tris(hydroxymethyl)cyclohexane-1,3,5-tricar-bonyl)tris(azanediyl))tris(hexane-6,1-diyl))tris(azanetriyl))hexa-hexanoate (47);

cis,cis-3,5-Bis((6-(bis(6-(octan-2-yloxy)-6-oxohexyl)amino)hexyl)carbamoyl)-1,3,5-tris(hydroxyme-thyl)cyclohexane-1-carboxylic acid (48);

Tetra(octan-2-yl) cis,cis-6,6',6'',6'''-((((1,3,5-tris((benzyloxy)methyl)-5-(pyrrolidine-1-carbonyl)cyclohex-ane-1,3-dicarbonyl)bis(azanediyl))bis(hexane-6,1-diyl))bis(azanetriyl))tetrahexanoate (49);

Tetra(octan-2-yl) cis,cis-6,6',6'',6'''-((((1,3,5-tris(hydroxymethyl)-5-(pyrrolidine-1-carbonyl)cyclohexane-1,3-dicarbonyl)bis(azanediyl))bis(hexane-6,1-diyl))bis(azanetriyl))tetrahexanoate (50);

cis,cis-$N^1$,$N^7$-Bis(6-(didodecylamino)hexyl)-5,7-bis(hydroxymethyl)-4-oxo-3-oxabicyclo[3.3.1]nonane-1,7-dicarboxamide (52);

cis,cis-N,N',N''-(Cyclohexane-1,3,5-triyl)tris(6-(didodecylamino)hexanamide) (56).

Compounds of formula I and II are prepared by the corresponding reaction of a cyclohexane precursor substituted with groups Z at positions 1, 3, 5 and precursor groups of linker X at positions 1; 1 and 3; or 1, 3 and 5 with an tertiary amine of general formula X'—Y—$N(R^1)_2$, wherein X' is a precursor group of the linker X. Preferably, X' is —$NH_2$ or activated carboxylic group. The tertiary amine of general formula X'—Y—$N(R^1)_2$ can be prepared by reactions and procedures known to those skilled in the art, and some suitable amines are also commercially available.

In one embodiment, the compounds of formula I are preferably prepared by reacting a compound of formula III, (III)

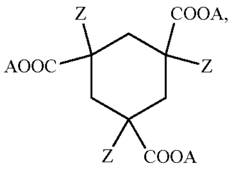

wherein A is H, halogen or benzyl,
with diamine of formula IV, (IV)

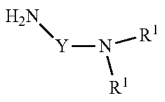

optionally in the presence of an alcohol selected from MeOH, BnOH, and optionally in the presence of pyrrolidine, a condensing agent and/or a base, optionally followed or preceded by hydrogenolysis. In formulas III and IV, $R^1$, Y and Z are as described above for formula I.

In a more specific example, the compounds of formula II are preferably prepared by reacting a compound of formula III, wherein A is hydrogen, with a diamine of formula IV in the presence of a condensing agent and a base, or by reacting a compound of formula III wherein A is a halogen, with a diamine of formula IV in the presence of a base. In formulas III and IV, $R^1$, Y and Z are as described above for formula II.

Another object of the present invention is a transfection agent comprising at least one lipidoid of general formula I or II, and at least one helper lipid. The transfection agent may be prepared in the form of a solution by dissolving and mixing the components, or it can be prepared in the form of particles by means of techniques used in conventional nanoparticle technology, such as microfluidic mixing. The particles are generally understood to mean nanoparticles with dimensions in the range of from 1 to 500 nm. Preferably, the dimensions of the nanoparticles are in the range of from 30 to 250 nm, even more preferably from 40 to 150 nm.

In one embodiment, the transfection agent contains at least one lipidoid of general formula I in an amount of 10 to 50 mol. %, and at least one helper lipid in an amount of 50 to 90 mol. %. Preferably, the transfection agent contains at least one lipidoid of general formula I in an amount of 15 to 40 mol. %, and at least one helper lipid in an amount of 60 to 85 mol. %. In some preferred embodiments, the transfection agent comprises at least one lipidoid of general formula I in an amount of 15 to 40 mol. %, cholesterol in an amount of 30 to 55 mol. %, and at least one other helper lipid in an amount of 20 to 50 mol. %.

In a particularly preferred embodiment, the transfection agent contains at least one lipidoid of general formula I in an amount of 15 to 40 mol. %, cholesterol in an amount of 30 to 55 mol. %, 1,2-dioleoyl-sn-glycero-3-phosphoethanolamine in an amount of 20 to 45 mol. % and 1,2-dimyristoyl-rac-glycero-3-methoxypolyethyleneglycol-2000 in an amount of 0.5 to 5 mol. %.

The present invention also relates to a transfection particle comprising at least one lipidoid of formula I, at least one nucleic acid and/or a part thereof and/or nucleic acid derivative, and preferably also at least one helper lipid. The transfection particles can be prepared, for example, by mixing a solution of a lipidoid of general formula I, optionally containing helper lipids, with a solution of the nucleic acid and/or a part thereof and/or nucleic acid derivative. Mixing can be performed by means of techniques used in conventional nanoparticle technology, for example, by microfluidic mixing.

The weight ratio of the total amount of nucleic acid and/or a part thereof and/or nucleic acid derivative to the total amount of lipidoid of general formula I and helper lipids in the transfection particle is preferably in the range of from 1:2 to 1:500, more preferably from 1:5 to 1:100. Specifically and for illustration: in the particles which are prepared in the examples herein below, this ratio was around 1:9 for mRNA and around 1:68 for siRNA.

Transfection particles are usually nanoparticles, which is generally understood to mean particles with dimensions in the range of from 1 to 500 nm. Typically, the dimensions of the transfection nanoparticles are in the range of from 50 to 250 nm, more preferably from 40 to 150 nm.

The structure of the transfection particles was observed by cryogenic transmission electron microscopy, and the observation showed that the transfection particles were compact layered lipid nanoparticles containing nucleic acid inside.

Helper lipids in transfection reagents and transfection particles are mainly neutral lipids, sterols or lipid conjugates of lipids with hydrophilic polymers.

Neutral lipids have a zero net charge under physiological conditions, and they can exist in an uncharged form or electroneutral zwitterionic form. Neutral lipids can be selected from e.g. 1,2-dioleoyl-sn-glycero-3-phosphoethanolamine (DOPE), 1,2-dioleoyl-sn-glycero-3-phosphocholine (DOPC), 1,2-distearoyl-sn-glycero-3-phosphocholine (DSPC), 1,2-dipalmitoyl-sn-glycero-3-phosphocholine (DPPC), 1,2-dimyristoyl-sn-glycero-3-phosphocholine (DMPC), and 1,2-dioleoyl-sn-glycero-3-phosphoethanolamine-N-(Cyanine 5).

Sterols may, for example, be selected from cholesterol, 0-sitosterol, stigmastanol, campesterol, fucosterol, avenasterol, fecosterol, brassicasterol, ergosterol, and 9,11-dehydroergosterol. Preferably, the sterol is cholesterol.

Lipid conjugates with hydrophilic polymers comprise a lipid portion and a polymer portion such as poly(ethyleneglycol), poly(2-ethyl-2-oxazoline), poly(2-methyl-2-oxazoline), poly(glycerol), poly(sarcosine). Preferably, the polymer portion consists of poly(ethyleneglycol) with a molecular weight which can range from about 500 to about 10,000 Da, more preferably from about 1,000 to about 5,000 Da.

Lipid conjugates with hydrophilic polymers may, for example, be selected from 1,2-dimyristoyl-rac-glycero-3-methoxy poly(ethyleneglycol)-2000, 1,2-dimyristoyl-sn-glycero-3-phosphoethanolamine-poly(ethyleneglycol)-2000, 1,2-distearoyl-sn-glycero-3-phosphoethanolamine poly(ethyleneglycol)-2000, 1,2-dipalmitoyl-sn-glycero-3-phosphoethanolamine poly(ethyleneglycol)-2000, and similar conjugates. A lipid conjugate with hydrophilic polymers may be preferably 1,2-dimyristoyl-rac-glycero-3-methoxy poly(ethyleneglycol)-2000.

The nucleic acid or a part thereof contains one or more nucleotides and/or deoxynucleotides. The nucleic acid or a part thereof may be a therapeutic, diagnostic or prophylactic agent, or may provide labeling for the cells or tissues into which they are transfected. The compounds of formula I thus have predominantly therapeutic or biotechnological uses.

The term "nucleic acid or a part thereof" is understood to mean one or more types of nucleic acids selected preferably from oligonucleotides (1-100 nucleotides, e.g. aptamers), cyclic dinucleotides (e.g. 2',3'-cGAMP), antisense oligonucleotides, deoxyribonucleic acid (single-stranded DNA, double-stranded DNA, cDNA, plasmid DNA encoding a gene or genes), ribonucleic acid, typically messenger RNA (mRNA), transfer RNA (tRNA), small interfering RNA (siRNA), double-stranded RNA, micro-RNA (miRNA), piwi-RNA (piRNA), antisense RNA (asRNA), guide RNA (gRNA) for the CRISPR system and their combinations (typically e.g. gRNA and mRNA encoding Cas9 nuclease, Cas13a/C2c2 and Cas13b, or analogous nucleases, suitable for use in CRISPR, CRISPRi and other variations and subsequent modification of the host cell or tissue genome or modification of the host cell or tissue transcriptome).

Furthermore, all nucleic acids (NA) disclosed herein may be formed or modified with synthetic base analogs, for example, to increase their stability in biological systems. Synthetic NA analogs involve, in particular, the following substitutions: 2'-O-methyl, 2'-O-methoxy-ethyl, 2'-fluoro, a methylene bridge between the 2'-oxygen and the 4'-carbon of the pentose ring (a so-called locked nucleic acid), phosphorylation at the 5' and/or 3' end of the strand, boranophosphonates, or phosphorothioates.

The present invention further includes the use of lipidoids of formula I or transfection agents or transfection particles for transfecting cells or tissues with nucleic acid and/or apart thereof and/or nucleic acid derivative in vitro. In addition, the invention includes lipidoids of formula I or transfection particles for use in transfecting cells or tissues with nucleic acid and/or a part thereof and/or nucleic acid derivative in vivo (excluding the transfection of human embryos for industrial or commercial use, and excluding the modification of a human germ line).

Transfection particles containing lipidoids of general formula I are useful in a number of biological applications in basic research, especially for the transfection of cell cultures or animals to deliver active nucleic acid and subsequent silencing or activation of a chromosomal gene or genes, genome editing (gene excision, gene insertion or mutation introduction) or transcriptome editing, or enabling the expression of a given protein encoded by the nucleic acid inserted by means of a transfection particle, so-called "in trans".

In veterinary and human medicine, transfection particles containing lipidoids of the general formula I can preferably be used for therapeutic or prophylactic purposes. Particles containing therapeutic nucleic acid can be administered to an animal or human to silence or activate chromosomal gene(s), to silence or activate immunogens, to inhibit or activate signaling pathways, to edit the genome (gene excision, gene insertion or mutation introduction) or the transcriptome, or enable the expression of protein(s) encoded by the nucleic acid.

The invention also provides lipidoids of general formula I or transfection agents or transfection particles for use as medicaments, in particular for gene therapy. In particular, they are suitable for use in the treatment of malignancies and/or genetic disorders.

The lipidoids of general formula (I) or the transfection agents or the transfection particles according to the present invention are also suitable for use as a prophylactic vaccines, preferably for the prevention of infectious diseases.

The lipidoids of general formula I or transfection particles can be formulated for therapeutic, cosmetic or biotechnological use in the form of preparations with pharmaceutically acceptable excipients. The formulations may be in liquid or solid form. Liquid forms include solutions, suspensions, dispersions, adapted e.g. for injection or oral administration, gels, ointments. Solid forms include, for example, capsules, tablets, coated tablets, powders, suppositories, and other forms.

The liquid formulations can be nebulized by inert gases. Nebulized suspensions may be breathed in directly, or from the nebulizing device, or the nebulizing device can be attached to a face mask or breathing machine.

The solid forms may be administered using dry-powder inhalers. Suspension or dry powder formulations can be administered orally or nasally from appropriate devices.

For application to the skin or mucous membranes, the preparations can be also prepared in the form of a cream, gel, ointment, paste, balm, liquid and others, and may be applied directly to the site of action.

Pharmaceutically acceptable excipients include solvents, solubility control agents, pH-adjusting agents, carriers, fillers, binders, glidants, disintegrants, preservatives, sorbents, viscosity control agents, agents that affect sensory properties such as taste, odor or the color of the formulation.

Furthermore, lipidoids of general formula I or the transfection agents or transfection particles can preferably be used for the purposes of the cosmetics industry in order to deliver the active substance to the site of action. The transfection particles with the active substance can be prepared in the form of a cream, gel, ointment, paste, balm, liquid or the like, and used as make-up, hair cosmetics or a personal hygiene product.

EXAMPLES

Figure 1:
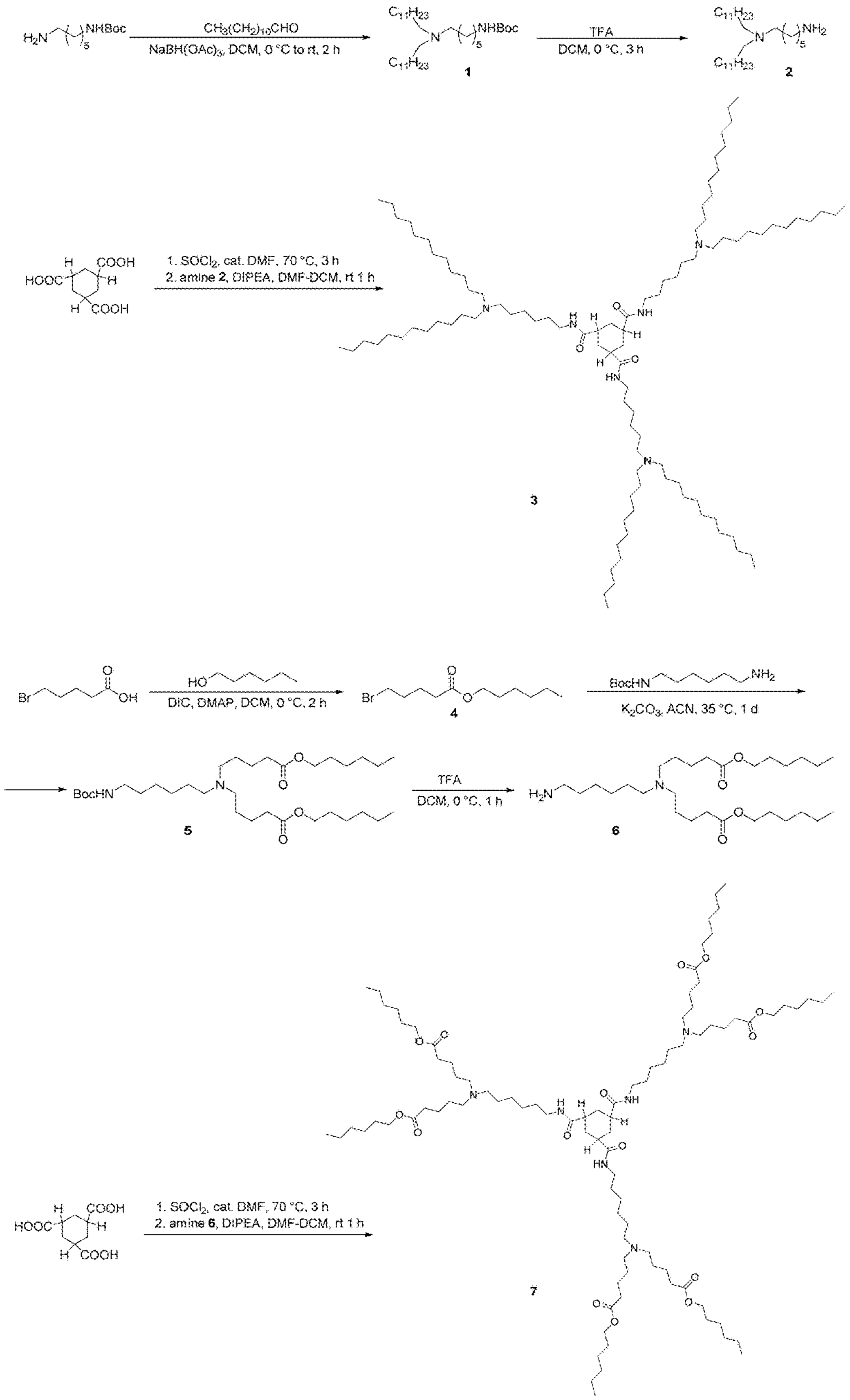
FIG. 1. Synthetic scheme of lipidoids 3 and 7.
Figure 2:
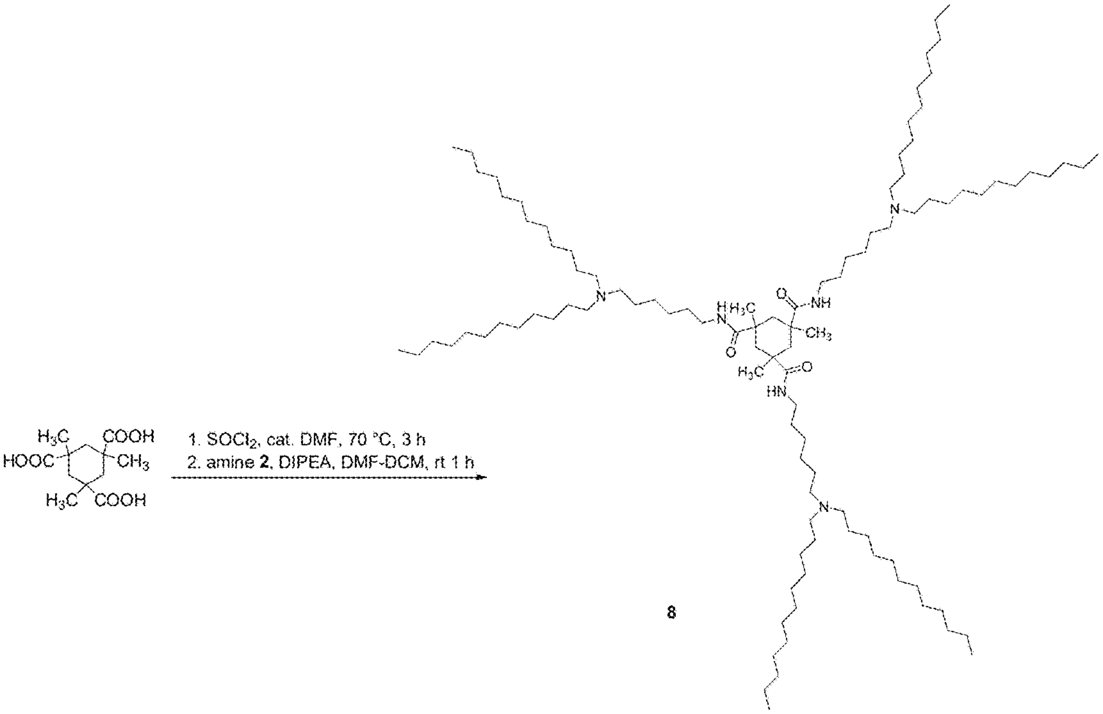
FIG. 2. Synthetic scheme of lipidoids 8 and 11.
Figure 2:
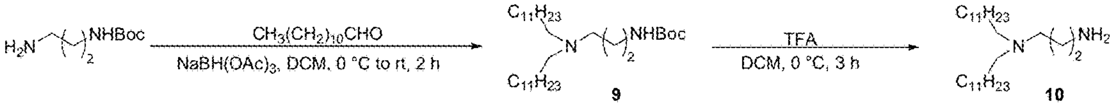
Figure 2:
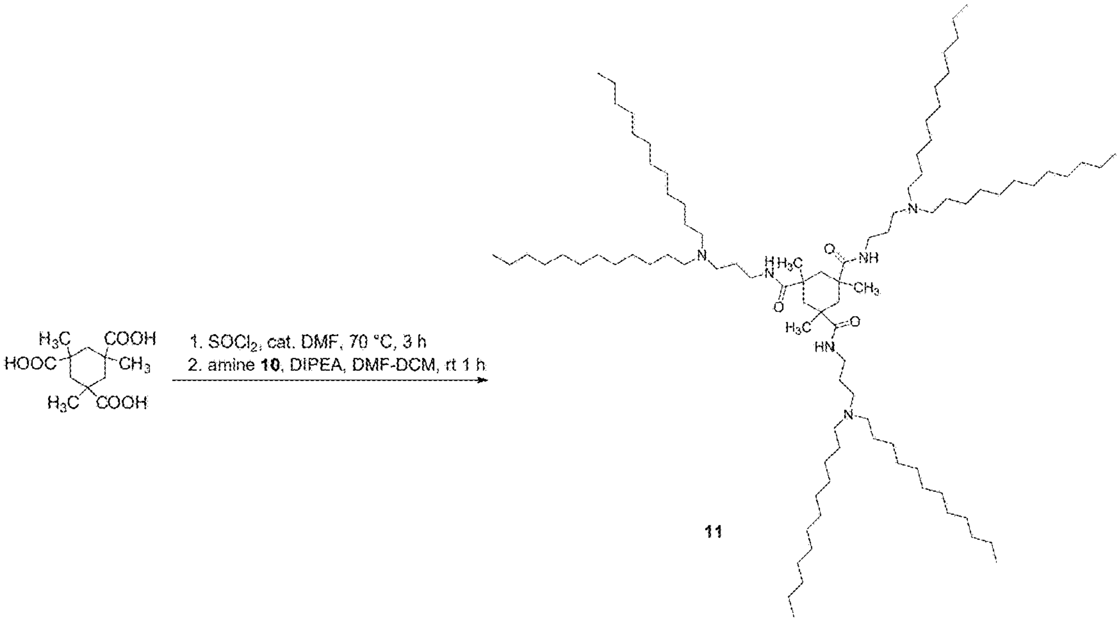
Figure 3:
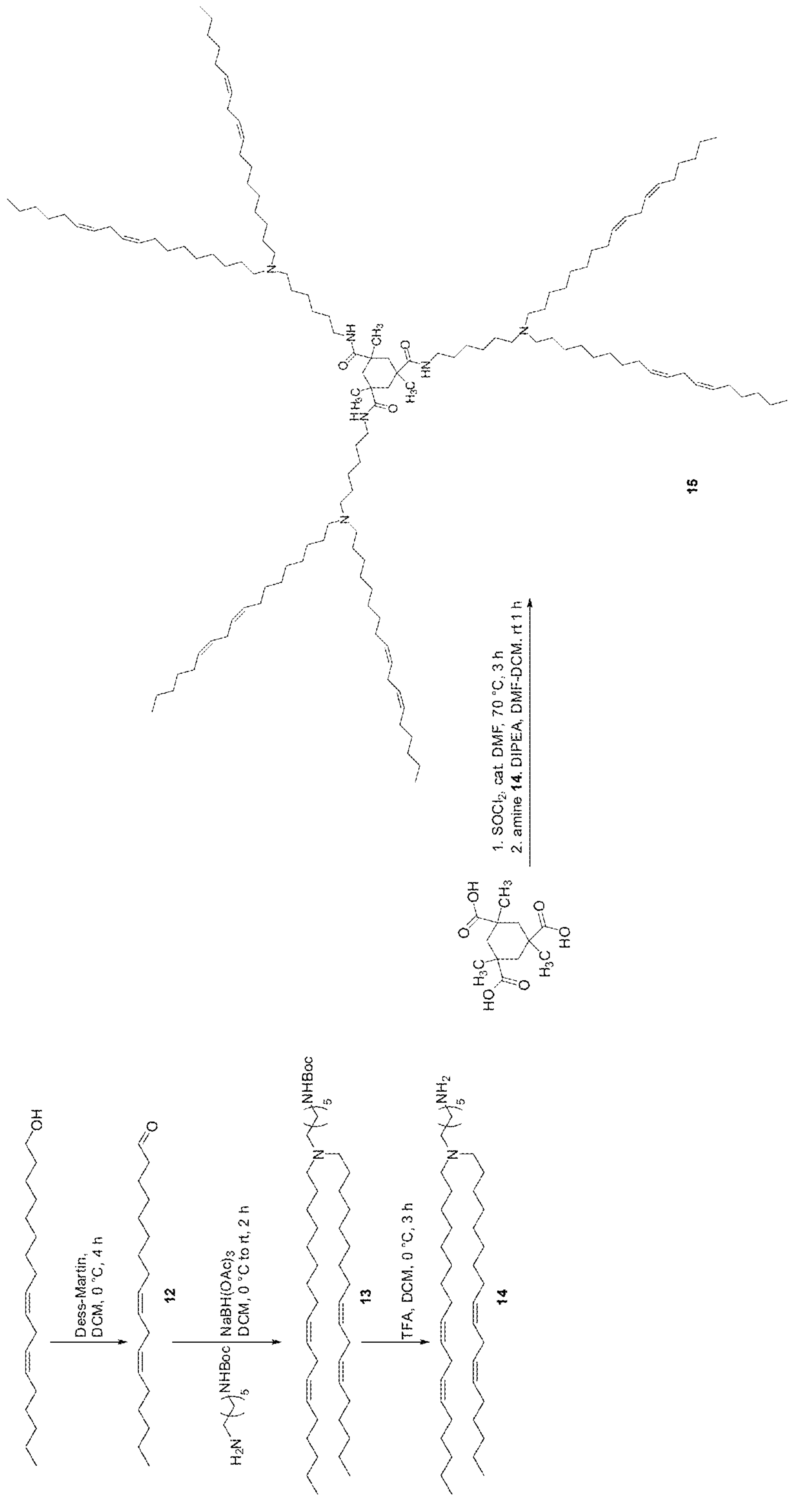
FIG. 3. Synthetic scheme of lipidoid 15.
Figure 4:
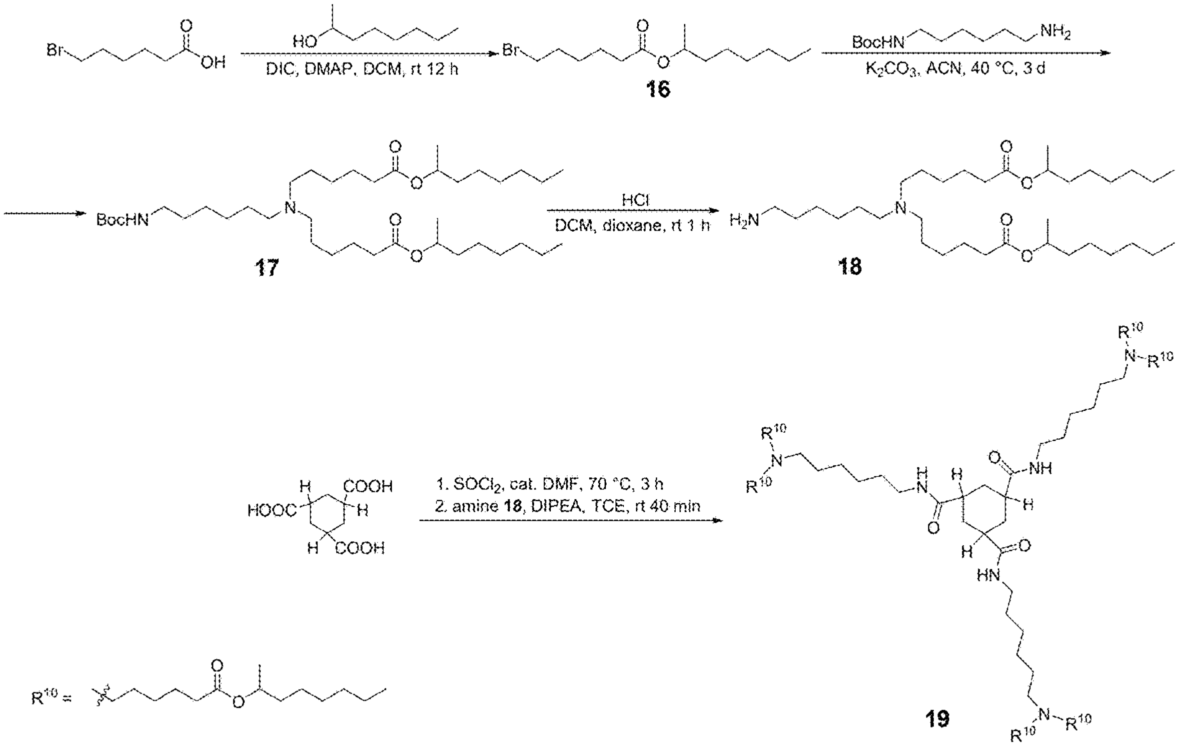
FIG. 4. Synthetic scheme of lipidoids 19 and 23.
Figure 4:
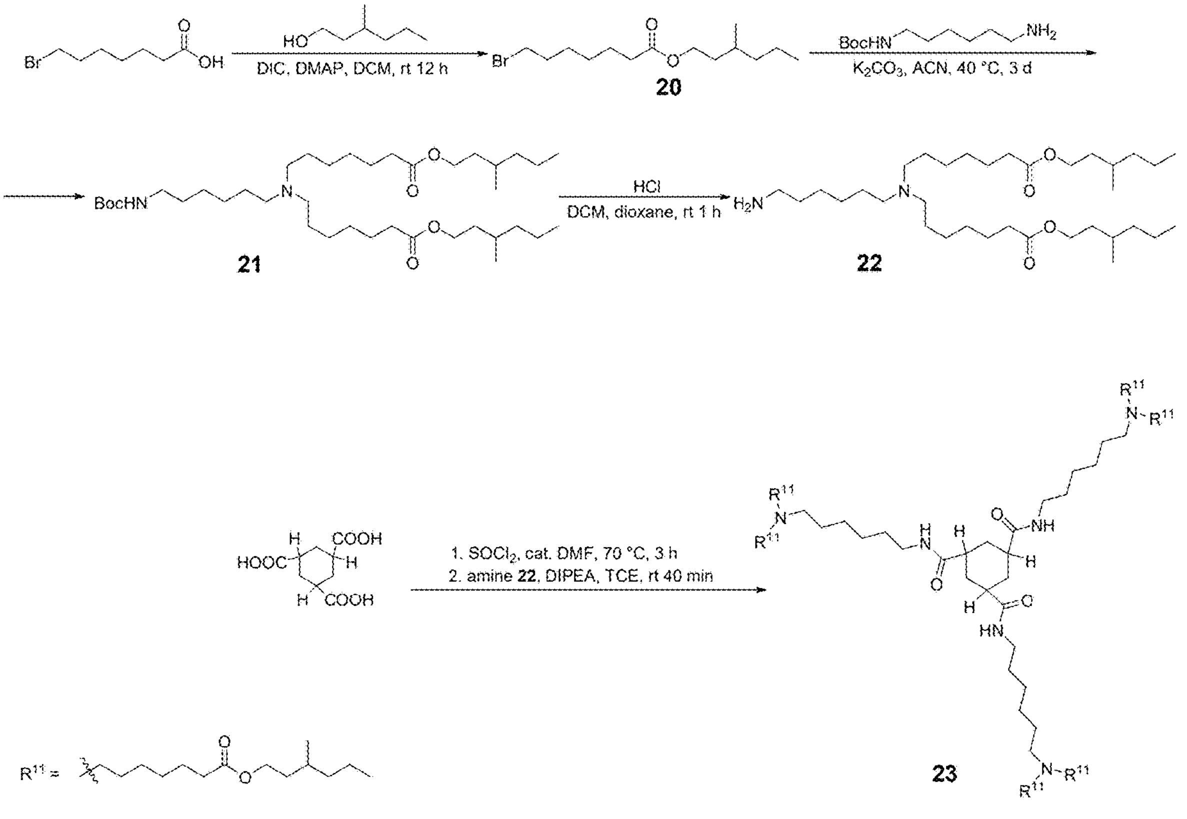
Figure 5:
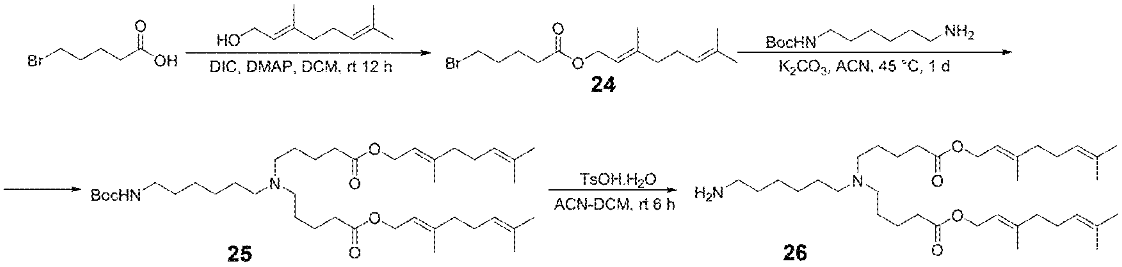
FIG. 5. Synthetic scheme of lipidoids 27 and 31.
Figure 5:
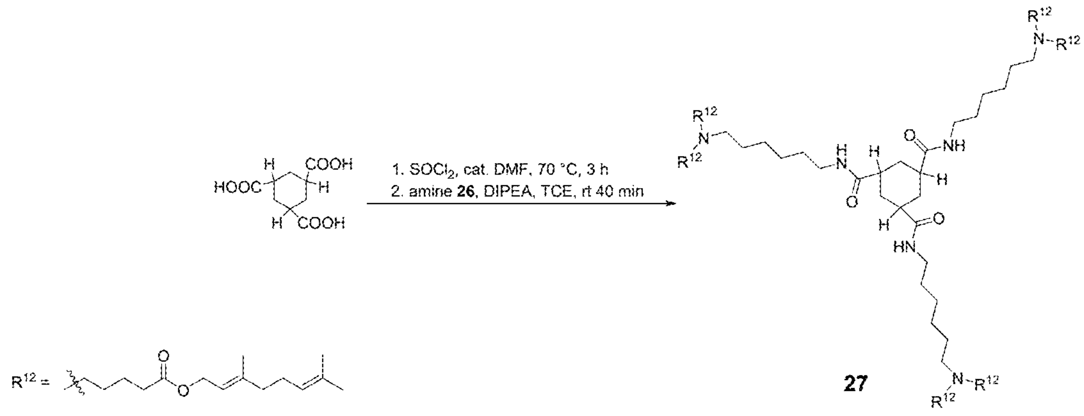
Figure 5:
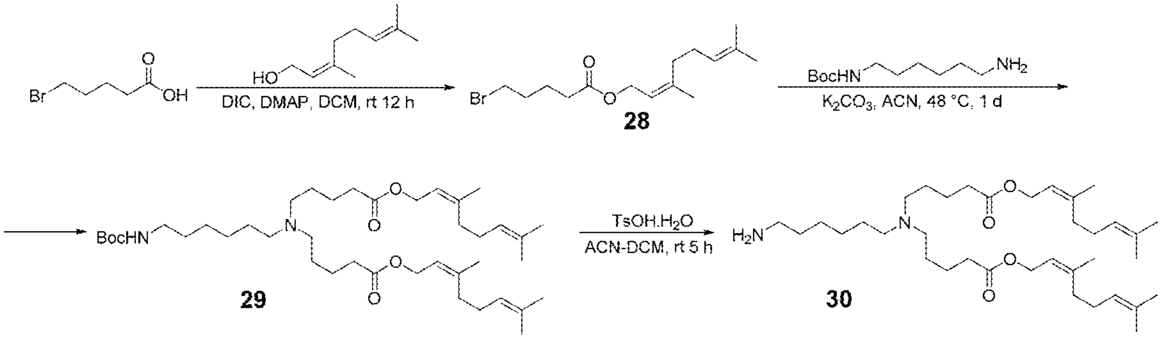
Figure 5:
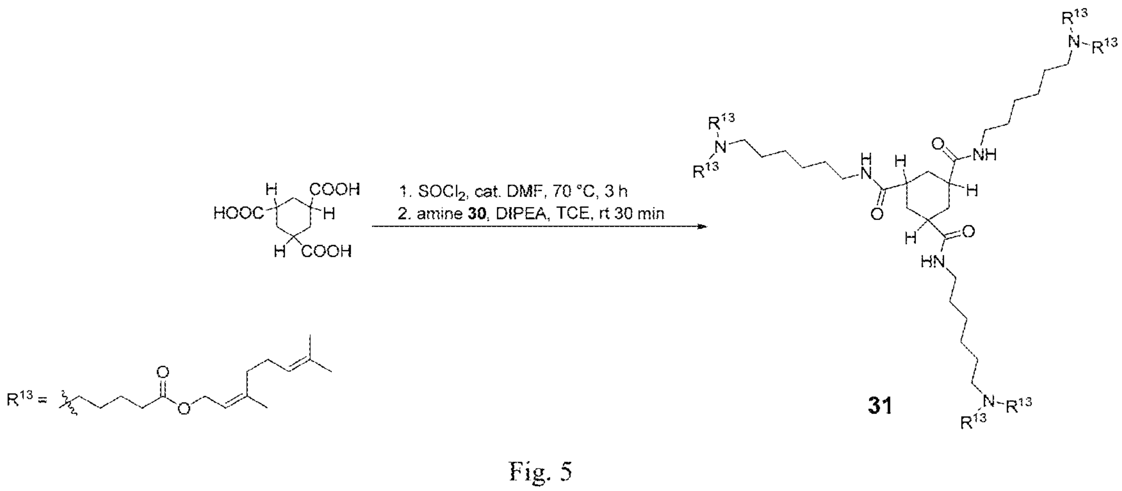
Figure 6:
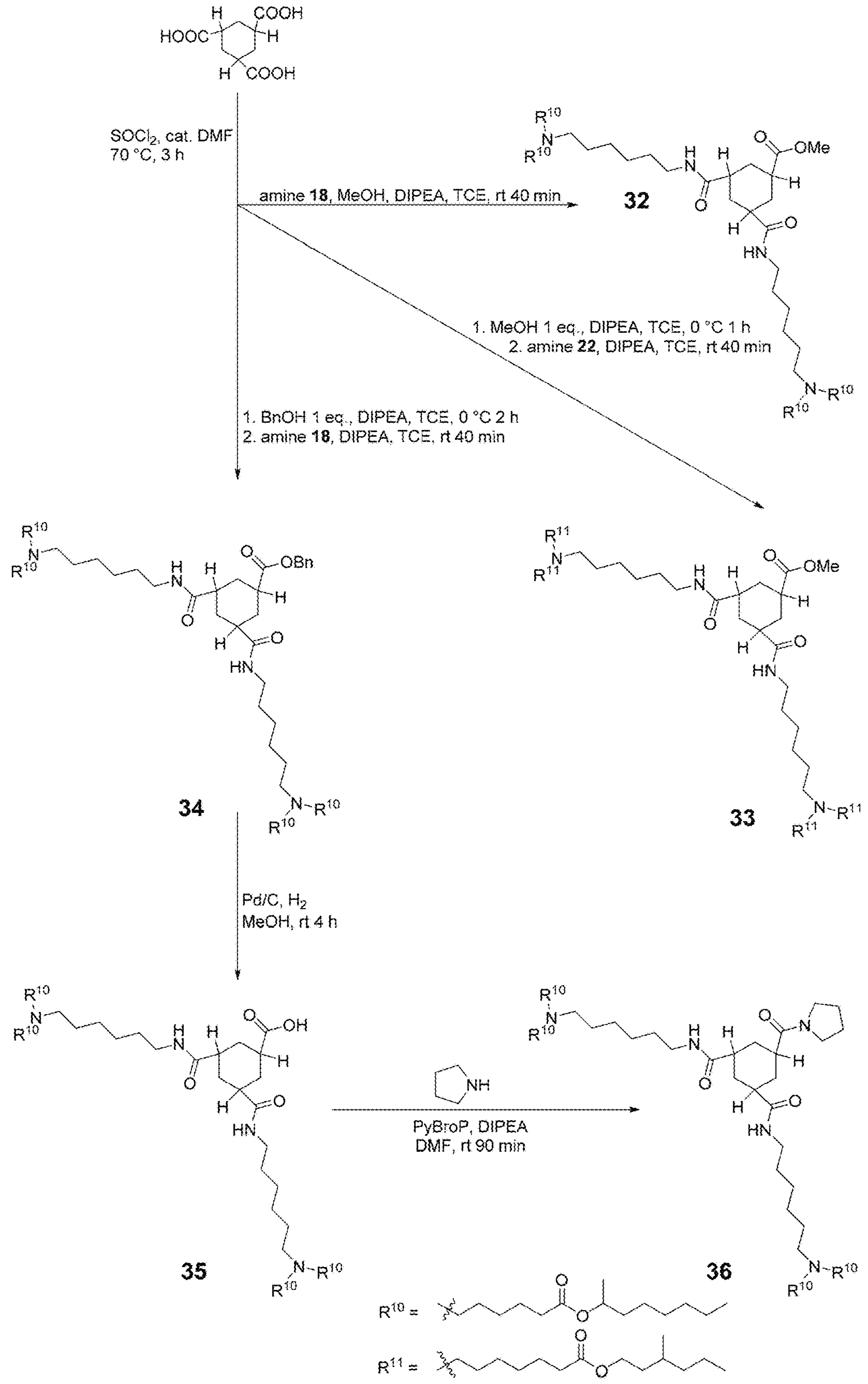
FIG. 6. Synthetic scheme of lipidoids 32, 33, 35 and 36.
Figure 7:
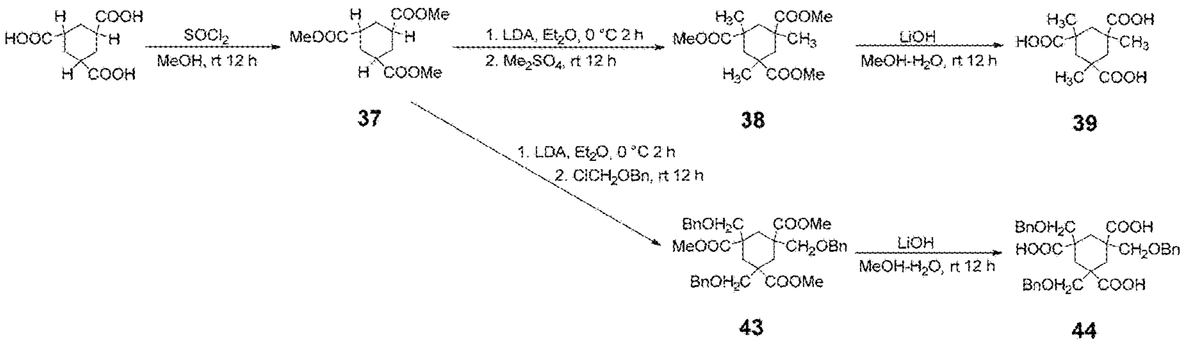
FIG. 7. Synthetic scheme of precursors 39 and 44 and lipidoids 40-42.
Figure 7:
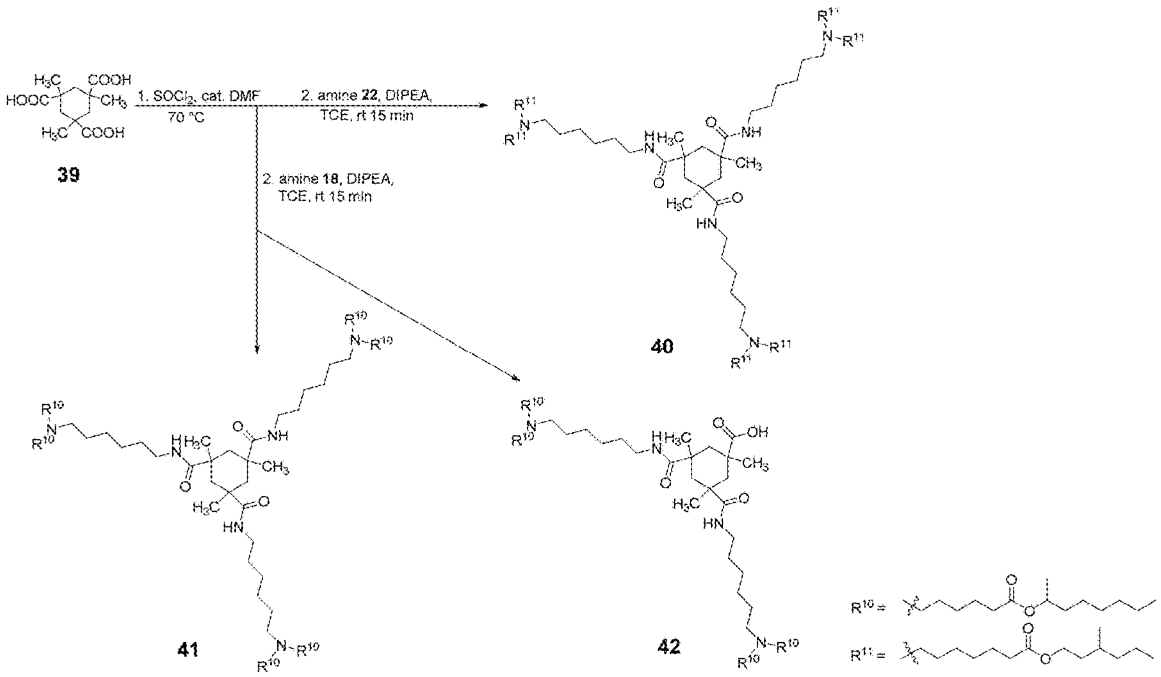
Figure 8:
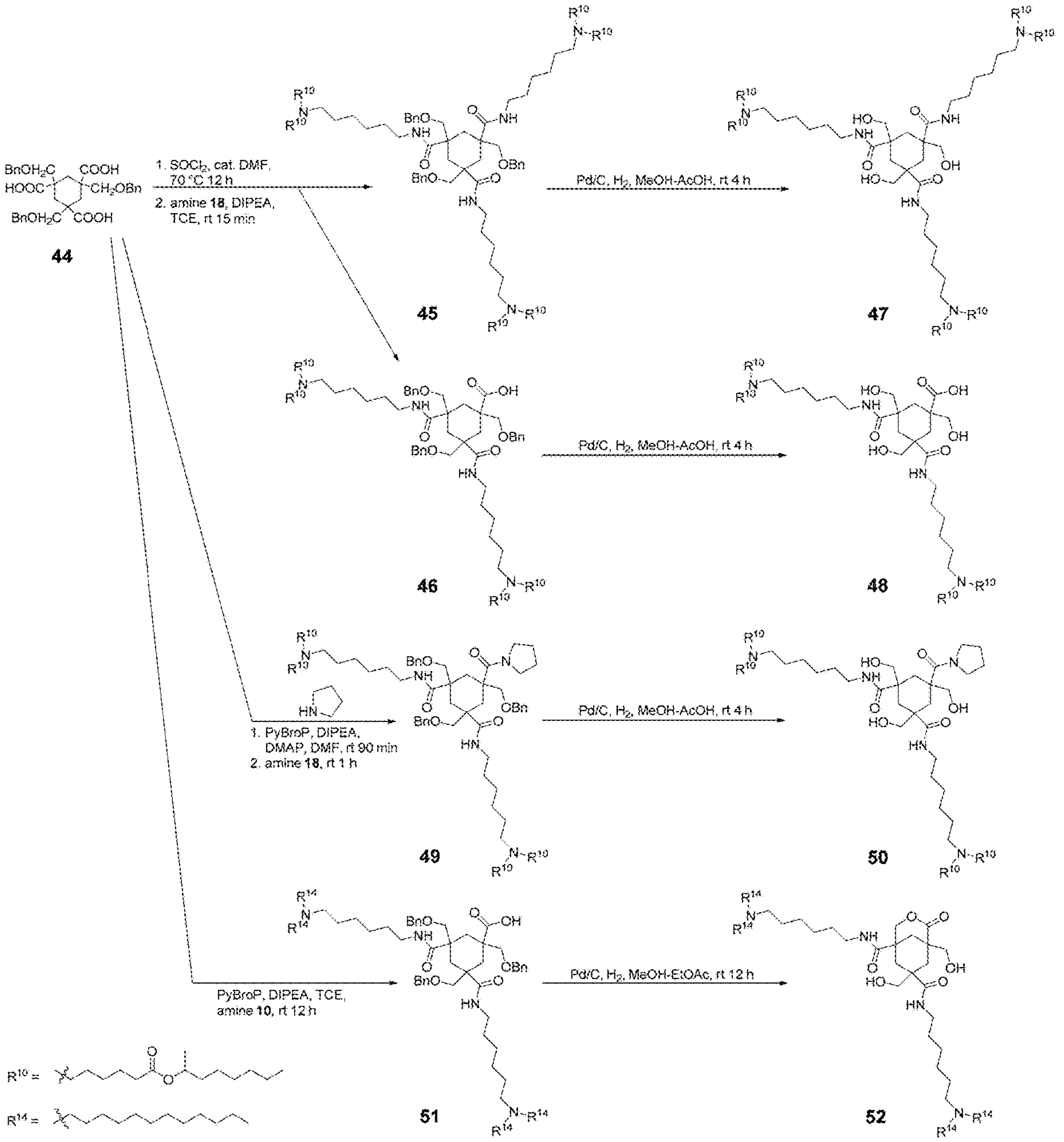
FIG. 8. Synthetic scheme of lipidoids 47, 48, 50 and 52.
Figure 9:
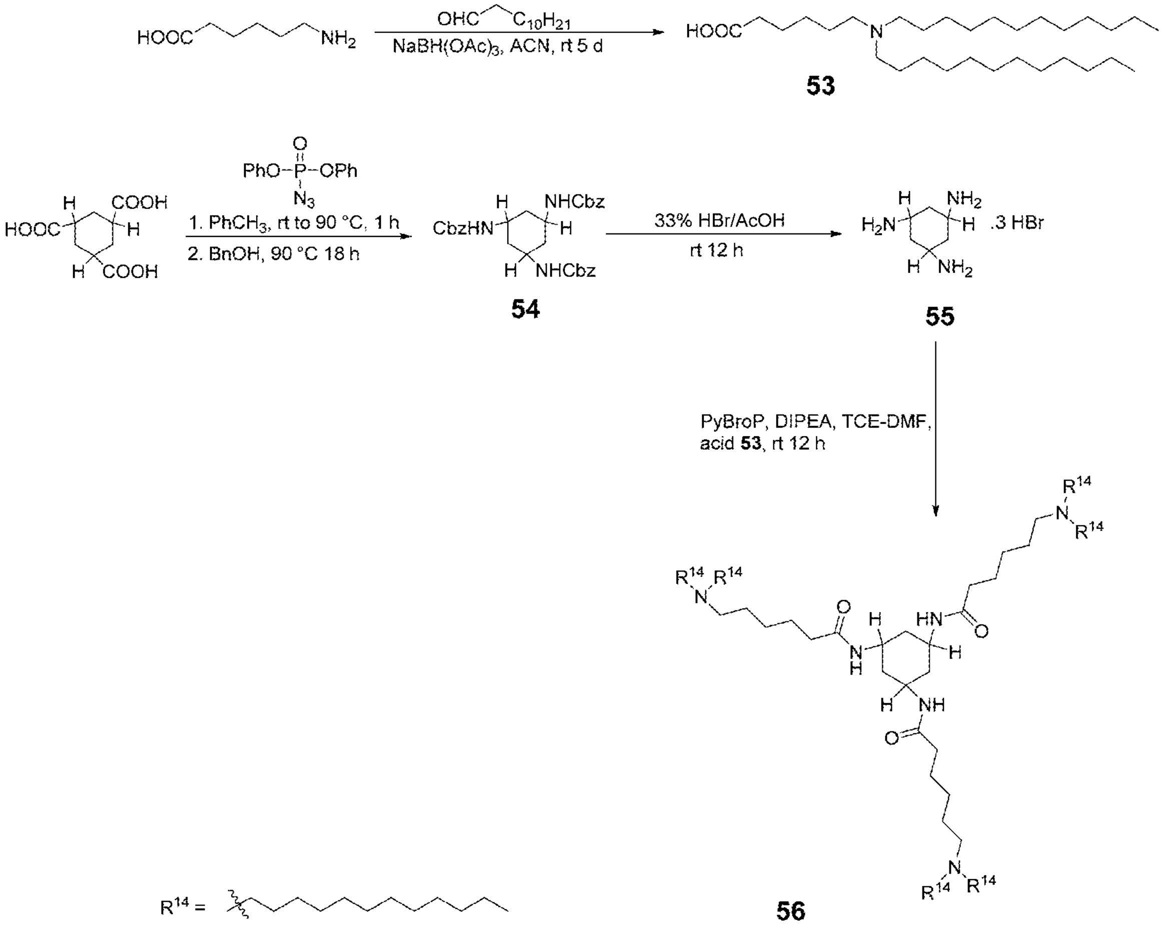
FIG. 9. Synthetic scheme of lipidoid 56.

List of Abbreviations eq. equivalent
$R_f$ retention factor
TLC thin-layer chromatography
RVE rotary vacuum evaporator
rt room temperature
v/v volume/volume
br s broad signal
s singlet
d doublet
t triplet
m multiplet
dd doublet of doublets
J interaction constant
δ chemical shift
HRMS high-resolution mass spectrometry
EI electron ionization
ESI electrospray ionization
MALDI matrix-assisted laser desorption/ionisation
GC-MS gas chromatography—mass spectrometry
IR infrared spectroscopy
NMR nuclear magnetic resonance
CE5 95:5 (v/v) cyclohexane-ethylacetate mixture
CE20 80:20 (v/v) cyclohexane-ethylacetate mixture
CE50 50:50 (v/v) cyclohexane-ethylacetate mixture
D1 75:22:3 (v/v/v) dichloromethane-methanol-25% aqueous $NH_3$ mixture
D2 175:22:3 (v/v/v) dichloromethane-methanol-25% aqueous $NH_3$ mixture
D3 275:22:3 (v/v/v) dichloromethane-methanol-25% aqueous $NH_3$ mixture
D4 375:22:3 (v/v/v) dichloromethane-methanol-25% aqueous $NH_3$ mixture
TFA trifluoroacetic acid
DIPEA N,N-diisopropylethylamine
DMF N,N-dimethylformamide
DCM dichloromethane
ACN acetonitrile
DIC diisopropylcarbodiimide
DMAP 4-dimethylaminopyridine
PyBroP bromotripyrrolidinophosphonium hexafluorophosphate
TCE 1,1,2,2-tetrachloroethane
LNP lipid nanoparticles
NA nucleic acid
DNA deoxyribonucleic acid
RNA ribonucleic acid
mRNA messenger RNA
siRNA small interfering RNA
tRNA transfer RNA
miRNA micro RNA
ssDNA/RNA single-stranded DNA/RNA
dsDNA/RNA double-stranded DNA/RNA
DMG-$PEG_{2000}$ 1,2-dimyristoyl-rac-glycero-3-methoxy-polyethyleneglycol-2000
DOPE 1,2-dioleoyl-sn-glycero-3-phosphoethanolamine
DOPC 1,2-dioleoyl-sn-glycero-3-phosphocholine
DSPC 1,2-distearoyl-sn-glycero-3-phosphocholine
DOPE-Cy5 1,2-dioleoyl-sn-glycero-3-phosphoethanolamine-N-(Cyanine 5)
Lip2000 Lipofectamine® 2000 (Invitrogen)
h hour

Example 1

$N^1$,$N^1$-Didodecylethan-1,6-diamine 2

A 500 ml round-bottom flask equipped with a calcium chloride drying tube and magnetic stirrer was filled with a solution of $N^1$-terc-butyloxycarbonyl-1,6-diaminohexane (5.0 g, 23.11 mmol) in DCM (100 ml) and cooled to 0° C. in an ice bath. With intensive stirring, n-dodecylaldehyde (15.38 ml, 69.34 mmol, 3 eq.) was added, followed by sodium triacetoxyborohydride (14.70 g, 69.34 mmol, 3 eq.) in three portions over 10 minutes. The cooling bath was removed, and the reaction mixture was stirred at room temperature for 2 h.

The progress of the reaction was monitored by TLC using an 80:20 (v/v) hexane-ethylacetate mobile phase on a TLC plate pre-saturated with ammonia (detection with ninhydrin). After completion of the reaction, aqueous NaOH solution (1 M, 200 ml) was added, the reaction mixture was stirred for 15 min, then poured into a separatory funnel and diluted with water (300 ml). The product was extracted with DCM (300 ml, 2×50 ml), the combined organic phase was washed with brine (50 ml), dried over anhydrous sodium sulphate, filtered through an S2 frit, and the solvents were evaporated in an RVE. The dark oily residue was purified by silica gel column chromatography using a linear gradient of ethyl acetate in hexane (10-30%). Amine 1 (3.67 g, 28.7%) was obtained as a yellowish oil.

Trifluoroacetic acid (10 ml) was added to a solution of compound 1 in DCM (10 ml), cooled to 0° C. with stirring in an ice bath, and the reaction mixture was left at 0° C. for 3 h. The solution was then poured into a 1 l separatory flask, diluted with 20% aqueous $Na_2CO_3$ (300 ml), and the product was extracted with DCM (250 ml, 2×50 ml). The combined organic phase was washed with brine (100 ml), dried over anhydrous sodium sulphate, filtered through an S2 frit, and the solvents were evaporated in an RVE. The crude product was purified by silica gel column chromatography using a linear gradient of D1 in DCM (0-70%). The diamine 2 (2.17 g, 72.2% yield; $R_f$ 0.31 in mobile phase D2 on a TLC plate pre-saturated with ammonia, detection with ninhydrin) was obtained in the form of a yellowish oil.

$^1$H NMR (600 MHz, $CDCl_3$): δ=2.73, 2.65, 2.57, 1.56, 1.52, 1.51, 1.36, 1.31, 1.28, 1.25-1.29, 1.24, 0.87 ppm. $^{13}$C NMR (150.9 MHz, $CDCl_3$): δ=53.51, 53.20, 41.62, 32.40, 31.89, 29.63, 29.61, 29.57, 29.44, 29.32, 27.39, 27.09, 26.53, 25.65, 25.02, 22.66, 14.10 ppm. IR (film): $v_{max}$/$cm^{-1}$=3374 w and 3294 w (v $NH_2$), 2797 m ($v_s$ N—$CH_2$), 2956 s ($v_{as}$ $CH_3$), 2924 vs ($v_{as}$ $CH_2$), 2853 s ($v_s$ $CH_2$), 1467 m and 1455 m, sh (p, $CH_2$ and $δ_{as}$ $CH_3$), 1378 w and 1367 w ($\delta_s$ $CH_3$), 721 m ($\beta_{as}$ $CH_2$). HRMS (ESI): m/z calculated for $C_{30}H_{65}N_2$ $[M+H]^+$ 453.51423; found 453.51340.

cis,cis-$N^1$,$N^3$,$N^5$-Tris(6-(didodecylamino)hexyl) cyclohexane-1,3,5-tricarboxamide 3

DMF (2 μl) andthionylchloride (300 μl) were addedto cis,cis-1,3,5-cyclohexanetricarboxylic acid (17 mg, 0.079 mmol) and the suspension was stirred for 30 min at 70° C. in a sealed vial, gradually clarifying the reaction mixture to a homogeneous colorless solution. Excess $SOCl_2$ was blown off with a stream of dry nitrogen at 70° C., the residue was dried under vacuum (10 min), and cooled to rt. A solution of $N^1$,$N^1$-didodecylhexane-1,6-diamine 2 (142 mg, 0.315 mmol, 4 eq.) and DIPEA (137 μl, 0.786 mmol, 10 eq.) in a mixture of DCM (1.5 ml) and DMF (0.5 ml), was added via septum using a syringe and the reaction mixture was stirred for 10 min. Subsequently, the reaction mixture was sorbed onto chromatographic silica gel (10 g), and the solvents were removed in an RVE. The residue was purified by silicagel column chromatography (40 g) using a linear gradient of D1 in DCM (0-55%). Lipidoid 3 was obtained (81 mg, 67.7% yield; $R_f$ 0.36 in mobile phase D2, detection with ninhydrin) in the form of a yellowish semi-solid.

$^1H$ NMR (600 MHz, $CDCl_3$): δ=7.80, 3.20, 3.02-2.96, 2.60, 2.07, 1.81-1.74, 1.37, 1.325, 1.28-1.23, 0.87 ppm. $^{13}C$ NMR (150.9 MHz, $CDCl_3$): δ=175.90, 52.85, 52.22, 42.83, 39.42, 31.87, 31.66, 29.58, 29.48, 29.43, 29.30, 29.08, 26.84, 26.18, 26.00, 23.50, 23.16, 22.65, 14.09 ppm. IR ($CCl_4$): $\nu_{max}/cm^{-1}$=3293 m (ν NH), 1640 s (amide I) and 1550 m (amide II), 2964 s, sh ($\nu_{as}$ $CH_3$), 2871 m, sh ($\nu_s$ $CH_3$), 2927 vs ($\nu_{as}$ $CH_2$), 2856 s, sh ($\nu_s$ $CH_2$), 1468 m and 1460 m, 1445 w ($\delta_s$ $CH_2$ and $\delta_{as}$ $CH_3$), 1378 w ($\delta_s$ $CH_3$), 721 w (fas $CH_2$ and $\delta_{as}$ $CH_2$); HRMS (MALDI): m/z calculated for $C_{99}H_{199}N_6O_3$ $[M+H]^+$ 1520.5598; found 1520.5598.

Example 2

$N^1$,$N^1$-Di((hexyloxycarbonyl)butyl)hexane-1,6-diamine 6

1-hexanol (2.48 ml, 19.89 mmol, 1.2 eq), DMAP (61 mg, 0.50 mmol, 0.03 eq.) and DIC (3.37 ml, 21.54 mmol, 1.3 eq.) were added to a solution of 5-bromopentanoic acid (3.00 g, 16.57 mmol) in DCM (60 ml) and the reaction mixture was stirred for 1 h at rt. Subsequently, the reaction mixture was sorbed onto chromatographic silica gel (16 g), the solvents were removed in an RVE, and the residue was purified by silicagel column chromatography (80 g) using a linear gradient of ethyl acetate in cyclohexane (0-10%).

Hexyl 5-bromopentanoate 4 (3.938 g, 89.6% yield; $R_f$ 0.31 in mobile phase CE5, detection $KMnO_4$) was obtained as a colourless liquid.

Hexyl 5-bromopentanoate 4 (1.53 g, 5.78 mmol, 2.5 eq.) and anhydrous $K_2CO_3$ (3.19 g, 23.11 mmol, 10 eq.) were added to a solution of N-tert-butyloxycarbonyl-1,6-diaminohexane (0.50 g, 2.31 mmol) in anhydrous ACN (10 ml) and the reaction mixture was stirred vigorously at 35° C. for 2 days. Subsequently, the reaction mixture was sorbed onto chromatographic silicagel (16 g), the solvents were removed in an RVE, and the residue was purified by silicagel column chromatography (40 g) using a linear gradient of ethyl acetate in cyclohexane (0-100%). Amine 5 was obtained (1.080 g, 79.9% yield; $R_f$ 0.31 in mobile phase CE50 on a TLC plate pre-saturated with ammonia, detection with ninhydrin) in the form of slightly yellowish oil.

Trifluoroacetic acid (4 ml) was added to a solution of compound 5 in DCM (4 ml) cooled to 0° C. with stirring in an ice bath, and the reaction mixture was left at 0° C. for 1 h. The solution was then poured into a 500 ml separatory flask, diluted with 20% aqueous $NaHCO_3$ (200 ml), and the product was extracted with DCM (150 ml, 2×50 ml). The combined organic phase was washed with brine (50 ml), dried over anhydrous sodium sulfate, filtered through an S2 frit, sorbed onto chromatographic silicagel (16 g), the solvents removed in an RVE, and the residue was purified by silicagel column chromatography (40 g) using a linear gradient of D1 in DCM (0-80%). Diamine 6 was obtained (0.788 g, 86.9% yield; $R_f$ 0.14 in mobile phase D2, detection with ninhydrin) as a yellowish oil. $^1H$ NMR (600 MHz, $CDCl_3$): δ=4.05, 3.63, 3.21, 3.15, 2.79, 2.68, 2.60, 2.51, 2.42, 2.32, 1.61, 1.50, 1.36-1.28, 0.88 ppm. $^{13}C$ NMR (150.9 MHz, $CDCl_3$): δ=173.62, 64.52, 53.68, 53.29, 41.22, 40.26, 34.03, 31.41, 28.58, 25.75, 25.57, 22.80, 22.51, 13.98 ppm.

HRMS (ESI): m/z calculated for $C_{28}H_{57}O_4N_2$ $[M+H]^+$ 485.43128; found 485.43052.

cis,cis-$N^1$,$N^3$,N-Tris(6-(di((hexyloxycarbonyl)butyl) amino)hexyl)cyclohexane-1,3,5-tricarboxamide 7

Lipidoid 7 was prepared from cis,cis-1,3,5-cyclohexanetricarboxylic acid (21 mg, 0.097 mmol), N',N-di((hexyloxycarbonyl) butyl)hexane-1,6-diamine 6 (188 mg, 389 mmol, 4 eq.) and DIPEA (169 μl, 0.971 mmol, 10 eq.) according to the procedure described for lipidoid 3 in Example 1. Lipidoid 7 (55 mg, 35%; $R_f$ 0.42 in mobile phase D2, detection with ninhydrin) was obtained as a yellowish semi-solid. $^1H$ NMR (600 MHz, $CDCl_3$): δ=6.23, 4.05, 3.205, 2.65, 2.34, 2.30, 2.085, 1.63-1.60, 1.49, 1.33-1.29, 0.88 ppm. $^{13}C$ NMR (150.9 MHz, $CDCl_3$): δ=174.35, 173.37, 64.60, 53.35, 52.88, 43.98, 39.12, 33.79, 31.94, 31.40, 29.21, 28.57, 26.62, 26.33, 25.56, 22.58, 22.51, 13.98 ppm. IR ($CCl_4$): $\nu_{max}/cm^{-1}$=1736 vs ($\nu_s$ C═O), 1173 m, 1075 w ($\nu_s$ C—O), 3293 m (ν NH), 1640 s (amide I) and 1551 m (amide II), 2955 s ($\nu_{as}$ $CH_3$), 2933 vs ($\nu_{as}CH_2$), 2875 m, sh ($\nu_s$ $CH_3$), 2860 m ($\nu_s$ $CH_2$), 1467 m and 1460 m (0, $CH_2$ and $\delta_{as}$ $CH_3$), 1379 w ($\delta_s$ $CH_3$), 724 w ($\beta_{as}$ $CH_2$ and $\gamma_{as}$ $CH_2$). HRMS (MALDI): m/z calculated for $C_{93}H_{175}N_6O_{15}[M+H]^+$ 1616.3110; found 1616.3095.

Example 3 cis,cis-$N^1$,$N^3$,$N^5$-Tris(6-(didodecylamino)hexyl)-1,3,5-trimethylcyclohexane-1,3,5-tricarboxamide 8

Lipidoid 8 was prepared from cis,cis-1,3,5-trimethyl-1,3,5-cyclohexanetricarboxylic acid (20 mg, 0.077 mmol), N',N-di(dodecyl)hexane-1,6-diamine 2 (140 mg, 310 mmol, 4 eq.) and DIPEA (135 μl, 0.774 mmol, 10 eq.) according to the procedure described for lipidoid 3 in Example 1. Lipidoid 8 (64 mg, 53%; $R_f$ 0.43 in mobile phase D2, detection with ninhydrin) was obtained in the form of a slightly yellowish solid oil. IR ($CCl_4$): $\nu_{max}/cm^{-1}$=3288 w, br (ν NH), 1651 m (amide I), 1585 w, br, sh and 1559 m, br (amide II), 2956 s ($\nu_{as}$ $CH_3$), 2927 vs ($\nu_{as}$ $CH_2$), 2878 m, sh (ν, $CH_3$), 2855 s (ν, $CH_2$), 1468 m, and 1459 m, sh, 1448 m, sh ($\beta_s$ $CH_2$ and $\delta_{as}$ $CH_3$), 1378 w ($\delta_s$ $CH_3$); 721 w ($\beta_{as}$ $CH_2$ and $\gamma_{as}$ $CH_2$). HRMS (MALDI): m/z calculated for $C_{102}H_{205}N_6O_3$ $[M+H]^+$ 1562.6068; found 1562.6011.

Example 4

$N^1$,$N^1$-Didodecylpropane-1,3-diamine 10

Amine 9 was prepared from $N^1$-tert-butyloxycarbonyl-1,3-diaminopropane (6.0 g, 34.43 mmol), n-dodecylaldehyde (22.91 ml, 103.30 mmol, 3 eq.) and sodium triacetoxyborohydride (21.89 g, 103.3 mmol, 3 eq.) according to the procedure described for compound 1 in Example 1. Amine 9 was obtained as a yellowish oil (7.72 g, 43.9%).

The deprotection of amine 9 was performed according to the procedure described for compound 2 in Example 1; diamine 10 (4.26 g, 68.6%; $R_f$ 0.35 in mobile phase D2 on a TLC plate pre-saturated with ammonia, detection with ninhydrin) was obtained in the form of a yellowish oil. $^1$H NMR (600 MHz, $CDCl_3$): δ=3.07, 2.70, 2.50, 1.81, 1.46, 1.28, 1.26, 1.25-1.29, 1.24, 0.87 ppm. $^{13}$C NMR (150.9 MHz, $CDCl_3$): δ=53.70, 53.30, 41.18, 31.90, 29.64, 29.62, 29.60, 29.58, 29.48, 29.33, 27.42, 25.71, 23.87, 22.67, 14.10 ppm. IR (film): $v_{max}/cm^{-1}$=3361 w and 3274 w (v $NH_2$), 2803 m ($v_s$ N—$CH_2$), 2954 s ($v_a$ $CH_3$), 2924 vs ($v_{as}$ $CH_2$), 2853 s ($v_s$ $CH_2$), 1467 m and 1456 m, sh (p, $CH_2$ and $\beta_{as}$ $CH_3$), 1378 w and 1364 w ($\delta_s$ $CH_3$), 720 m ($P_{as}$ $CH_2$). HRMS (ESI): m/z calculated for $C_{27}H_{59}N_2[M+H]^+$ 411.46728; found 411.46652.

cis,cis-N[1],N[3],N[5]-Tris(3-(didodecylamino)propyl)-1,3,5-trimethylcyclohexane-1,3,5-tricarboxamide 11

Lipidoid 11 was prepared from cis,cis-1,3,5-trimethyl-1,3,5-cyclohexanetricarboxylic acid (20 mg, 0.077 mmol), N',N'-di(dodecyl)propane-1,3-diamine 10 (127 mg, 310 mmol, 4 eq.) and DIPEA (135 μl, 0.774 mmol, 10 eq.) according to the procedure described for lipidoid 3 in Example 1. Lipidoid 11 (41 mg, 37% yield; $R_f$0.36 in mobile phase D2, detection with ninhydrin) was obtained in the form of a slightly yellowish solid oil. IR ($CCl_4$): $v_{max}/cm^{-1}$=3303 w, vbr (v NH), 1679 s, sh (amide I), 1513 w, br, sh (amide II), 2956 s ($v_{as}$ $CH_3$), 2927 vs ($v_{as}$ $CH_2$), 2878 m, sh ($v_s$ $CH_3$), 2855 s ($v_s$ $CH_2$), 1464 m, sh (p, $CH_2$ and $6_{as}$ $CH_3$), 1380 w ($\delta_s$ $CH_3$); 721 w ($\beta_{as}$ $CH_2$ and $\gamma_{as}$ $CH_2$). HRMS (MALDI): m/z calculated for $C_{93}H_{187}N_6O_3$ $[M+H]^+$ 1436.4665; found 1436.4629.

Example 5

Linoleylaldehyde 12

Dess-Martin periodinane (4.45 g, 10.49 mmol, 1.3 eq.) was added to a solution of linoleylalcohol (2.50 ml, 8.07 mmol) in DCM (120 ml) cooled to 0° C. with an ice bath and the mixture was stirred at 0° C. for 4 h. The reaction was then quenched by the addition of sodium thiosulfate solution (20 g $Na_2S_2O_3$, $5H_2O$/100 ml $H_2O$) and saturated aqueous sodium bicarbonate solution (50 ml), and stirred at rt for 1 h until the initially milky solution turned clear. The solution was poured into a 1000 ml separatory flask, diluted with water (150 ml), and the product was extracted with DCM (150 ml, 2×50 ml). The combined organic phase was washed with brine (150 ml), dried over anhydrous sodium sulfate, filtered through an S2 frit, and the solvents were evaporated on a RVE. The crude product was purified by silicagel column chromatography (isocratic conditions, 5% ethyl acetate in cyclohexane). Aldehyde 12 (1.271 g, 59.6% yield; $R_f$ 0.36 in mobile phase CE5, detection with $KMnO_4$) was obtained as a colorless oil.

N[1],N[1]-Di((9Z,12Z)-octadeca-9,12-dien-1-yl)hexane-1,6-diamine 14

Amine 13 was prepared from N[1]-tert-butyloxycarbonyl-1,6-diaminohexane (0.345 g, 1.59 mmol), aldehyde 12 (1.27 g, 4.78 mmol, 3 eq.) and sodium triacetoxyborohydride (1.01 g, 4.78 mmol, 3 eq.) according to the procedure described for compound 1 in Example 1. Amine 13 was obtained as a yellowish oil (1.08 g, 94.9% yield; $R_f$ 0.18 in CE20 mobile phase, detection with ninhydrin).

Deprotection of amine 13 was performed in a mixture of TFA (4 ml) and DCM (5 ml) according to the procedure described for compound 2 in Example 1; diamine 14 (0.594 g, 64.0%; $R_f$ 0.13 in mobile phase D2, detection with ninhydrin) was obtained as a yellowish oil. $^1$H NMR (600 MHz, $CDCl_3$): δ=5.30-5.40, 2.765, 2.73, 2.67, 2.59, 2.04, 1.51, 1.385, 1.37, 1.34, 1.295, 1.29, 1.28-1.34, 1.28, 0.88 ppm. $^{13}$C NMR (150.9 MHz, $CDCl_3$): δ=130.19, 130.06, 127.99, 127.89, 53.49, 53.45, 41.67, 32.52, 31.50, 29.62, 29.46, 29.20-29.48, 27.37, 27.20, 27.18, 26.52, 25.61, 22.56, 14.06 ppm. IR ($CCl_4$): $v_{max}/cm^{-1}$=3011 s ($v_{as}$=CH); 1646-1673 m (v C═C); 3455 w ($v_{as}$ $NH_2$); 3394 ($v_s$ $NH_2$); 1620 w (0, $NH_2$); 1087 m (v C—$NH_2$); 2957 s, sh ($v_{as}$ $CH_3$); 2928 vs ($v_{as}$ $CH_2$); 2873 s, sh ($v_s$ $CH_3$); 2856 vs ($v_s$ $CH_2$); 2801 m ($v_s$ N—$CH_2$); 1467 m and 1457 m, sh (p, $CH_2$ and $\delta_{as}$ $CH_3$); 1378 m ($\delta_s$ $CH_3$); 721 m ($\beta_{as}$ and $\gamma_{as}$ $CH_2$). HRMS: m/z calculated for $C_{42}H_{81}N_2$ $[M+H]^+$ 613.63943; found 613.63899.

cis,cis-N[1],N[3],N-Tris(6-(di((9Z,12Z)-octadeca-9,12-dien-1-yl)amino)hexyl)-1,3,5-trimethylcyclohexane-1,3,5-tricarboxamide 15

Lipidoid 15 was prepared from cis,cis-1,3,5-trimethyl-1,3,5-cyclohexanetricarboxylic acid (17 mg, 0.066 mmol), N[1],N-di((9Z,12Z)-octadeca-9,12-dien-1-yl)hexane-1,6-diamine 14 (161 mg, 273 mmol, 4 eq.) and DIPEA (115 μl, 0.658 mmol, 10 eq.) according to the procedure described for lipidoid 3 in Example 1.

Lipidoid 15 (86 mg, 64% yield; $R_f$ 0.36 in mobile phase D2, detection with ninhydrin) was obtained as a pale yellow solid. IR ($CCl_4$): $v_{max}/cm^{-1}$=3348 w, br, sh and 3302 w, br (v NH), 1656 m and 1635 m, sh (amide I+v C═C), 1565 w, sh and 1557 w, br (amide II), 3011 m ($v_{as}$=C—H), 2956 s ($v_{as}$ $CH_3$), 2929 vs ($v_a$$CH_2$), 2875 m, sh ($v_s$ $CH_3$), 2856 s ($v_s$ $CH_2$), 1467 m and 1450 m, sh, (p, $CH_2$ and $\beta_{as}$ $CH_3$), 1379 w ($\delta_s$ $CH_3$); 720 w ($\beta_{as}$ $CH_2$+$\gamma_{as}$ $CH_2$+γ=C—H). HRMS (MALDI): m/z calculated for $C_{138}H_{253}N_6O_3$ $[M+H]^+$ 2042.9829; found 2042.9861.

Example 6

Compound 18

DIC (4.41 mL, 28.7 mmol, 1.6 eq.) and DMAP (88 mg, 0.72 mmol, 0.04 eq.) were added to a solution of 6-bromohexanoic acid (3.50 g, 17.9 mmol) and octan-2-ol (3.51 g, 26.9 mmol, 1.5 eq.) in DCM (30 mL), and the mixture was stirred overnight at rt. The reaction mixture was then adsorbed onto silica (16 g), and the solvents were evaporated in vacuo. The crude product was purified by flash chromatography on silica (80 g, elution with a linear gradient of ethyl acetate in cyclohexane, 0-10%) to yield the compound 16 (4.02 g, 77%; $R_f$ 0.41 in CE5, visualization by $KMnO_4$) as a colorless oil.

Bromoester 16 (4.00 g, 13.1 mmol, 2.6 eq.) and potassium carbonate (7.23 g, 52.3 mmol, 10 eq.) were added to a solution of N-Boc-1,6-hexanediamine (1.13 g, 5.23 mmol, 1 eq.) in anhydrous ACN (10 mL), and the mixture was stirred at 40° C. for 3 days. The reaction mixture was then adsorbed onto silica (16 g), and the solvents were evaporated in vacuo. The crude product was purified by flash chromatography on silica (80 g, elution with a linear gradient of ethyl acetate in cyclohexane, 0-100%) to yield the compound 17 (2.80 g, 80%; $R_f$ 0.58 in CE50 on an $NH_3$-pretreated TLC plate, visualization by ninhydrin) as a pale-yellow oil.

Hydrochloric acid in dioxane (4 mL, 4 M) was added to a solution of compound 17 (2.75 g, 4.11 mmol) in anhydrous DCM (4 mL), and the reaction mixture was stirred at rt for 1 h. The solution was then poured into a 500 mL separatory funnel, diluted with saturated aqueous $NaHCO_3$ (100 mL), and the product was extracted with diethyl ether (100 mL, 2×50 mL). The combined organic phases were washed with brine (75 mL), dried over anhydrous sodium sulfate, filtered through an S2 sintered glass, and the solvents were evaporated in an RVE. The crude product was purified by column chromatography on silica using a linear gradient of D1 in DCM (0-70%). The amine 18 (1.74 g, 74%; $R_f$ 0.25 in D2 on an $NH_3$-pretreated TLC plate, visualization by ninhydrin) was obtained as a pale-yellow oil. $^1H$ NMR (600 MHz, $CDCl_3$): δ=4.90-4.77 (m), 2.72-2.62 (m), 2.39-2.29 (m), 2.21 (t, J=7.5 Hz), 1.64-1.44 (m), 1.47-1.32 (m), 1.30-1.17 (m), 1.15-1.08 (m), 0.86-0.78 (m) ppm. $^{13}C$ NMR (150.9 MHz, $CDCl_3$): δ=173.42, 70.83, 53.89, 41.87, 35.98, 31.77, 29.13, 27.41, 27.17, 26.84, 26.69, 25.40, 25.09, 22.60, 20.04, 14.09 ppm. HRMS (ESI): m/z calculated for $C_{34}H_{68}N_2O_4[M+H]^+$ 569.5252; found 569.5247.

Hexa(octan-2-yl) cis,cis-6,6',6",6"',6"",6""'-((((cyclohexane-1,3,5-tricar-bonyl)tris(azanediyl))tris(hexane-6,1-diyl))tris(azanetriyl))hexahexanoate 19

Thionylchloride (700 μL) and DMF (6 μL) were added to cis,cis-cyclohexane-1,3,5-tricarboxylic acid (80 mg, 370 μmol), and the suspension was stirred for 3 h at 70° C. in a closed vial; during this time the suspension turned into a clear solution. Excess $SOCl_2$ was removed at 70° C. with a stream of dry nitrogen, the residue was dried at rt in vacuo (20 min), and the obtained solid was dissolved under argon in anhydrous TCE (2.5 mL) and DIPEA (645 μL, 3.70 mmol). Then, a solution of amine 18 (1.05 g, 1.85 mmol, 5 eq.) in anhydrous TCE (2.5 mL) was added and the reaction mixture was stirred for 40 min at rt. The reaction mixture was then evaporated in vacuo, redisolved in DCM, adsorbed onto silica (10 g), and the DCM was removed in vacuo. The crude product was purified by flash chromatography on silica (elution with a linear gradient of D1 in DCM, 5-35%) to yield the target compound 19 (489 mg, 71%) as a yellow waxy semi-solid. $^1H$ NMR (600 MHz, $CDCl_3$): δ=5.75, 4.88, 3.21, 2.42, 2.27, 2.22, 2.11, 1.62, 1.58, 1.56, 1.47, 1.46, 1.30, 1.28, 1.27, 1.26, 1.19, 0.87 ppm. $^{13}C$ NMR (150.9 MHz, $CDCl_3$): 173.88, 173.39, 70.82, 53.87, 53.77, 44.10, 39.44, 35.93, 34.67, 31.86, 31.73, 29.51, 29.09, 27.08, 26.74, 25.36, 25.01, 22.56, 20.01, 14.06 ppm.

HRMS (MALDI): m/z calcd. for $C_{111}H_{211}N_6O_{15}$ $[M+H]^+$ 1868.5927; found 1868.5906.

Example 7

Compound 22

DIC (3.60 mL, 23.0 mmol, 1.6 eq.) and DMAP (70 mg, 0.58 mmol, 0.04 eq.) were added to a solution of 7-bromoheptanoic acid (3.00 g, 14.4 mmol) and 3-methylhexan-1-ol (2.50 g, 21.5 mmol, 1.5 eq.) in DCM (30 mL), and the mixture was stirred overnight at rt. The reaction mixture was then adsorbed onto silica (16 g), and the solvents were evaporated in vacuo. The crude product was purified by flash chromatography on silica (80 g, elution with a linear gradient of ethyl acetate in cyclohexane, 0-10%) to yield the compound 20 (3.64 g, 83%; $R_f$ 0.27 in CE5, visualization by $KMnO_4$) as a colorless oil.

Bromoester 20 (3.63 g, 11.8 mmol, 2.6 eq.) and potassium carbonate (6.29 g, 45.5 mmol, 10 eq.) were added to a solution of N-Boc-hexane-1,6-diamine (0.98 g, 4.55 mmol, 1 eq.) in anhydrous ACN (10 mL), and the mixture was stirred at 40° C. for 3 days. The reaction mixture was then adsorbed onto silica (16 g), and the solvents were evaporated in vacuo. The crude product was purified by flash chromatography on silica (80 g, elution with a linear gradient of ethyl acetate in cyclohexane, 0-100%) to yield the compound 21 (2.90 g, 95%; $R_f$ 0.54 in CE50 on an $NH_3$-pretreated TLC plate, visualization by ninhydrin) as a pale-yellow oil.

Hydrochloric acid in dioxane (4 mL, 4 M) was added to a solution of compound 21 (2.85 g, 4.26 mmol) in anhydrous DCM (4 mL), and the reaction mixture was stirred at rt for 1 h. The solution was then poured into a 500 mL separatory funnel, diluted with saturated aqueous $NaHCO_3$ (100 mL), and the product was extracted with diethyl ether (100 mL, 2×50 mL). The combined organic phases were washed with brine (75 mL), dried over anhydrous sodium sulfate, filtered through an S2 sintered glass, and the solvents were evaporated in an RVE. The crude product was purified by silica gel column chromatography using a linear gradient of D1 in DCM (0-70%). The amine 22 (2.38 g, 96%; $R_f$ 0.48 in D2 on an $NH_3$-pretreated TLC plate, visualization by ninhydrin) was obtained as a pale-yellow oil.

$^1H$ NMR (400 MHz, $CDCl_3$): δ=4.08-3.96 (m), 2.63-2.58 (m), 2.33-2.26 (m), 2.21 (t, J=7.5 Hz), 1.61-1.50 (m), 1.49-1.40 (m), 1.40-1.30 (m), 1.30-1.14 (m), 1.14-1.00 (m), 0.85-0.76 (m) ppm. $^{13}C$ NMR (150.9 MHz, $CDCl_3$): 173.85, 62.77, 54.13, 42.19, 38.98, 35.55, 34.35, 33.79, 29.56, 29.15, 27.49, 27.29, 26.88, 25.01, 19.95, 19.48, 14.26 ppm. HRMS (ESI): m/z calculated for $C_{34}H_{68}N_2O_4[M+H]^+$ 569.5252; found 569.5250.

Hexakis(3-methylhexyl) cis,cis-7,7',7",7"',7" ",7""'-((((cyclohexane-1,3,5-tricarbonyl) tris(azanediyl))tris(hexane-6,1-diyl))tris(azanetriyl))hexaheptanoate 23

Thionylchloride (500 μL) and DMF (4 μL) were added to cis,cis-cyclohexane-1,3,5-tricarboxylic acid (60 mg, 278 μmol), and the suspension was stirred for 3 h at 70° C. in a closed vial; during this time the suspension turned into a clear solution. Excess $SOCl_2$ was removed at 70° C. with a stream of dry nitrogen, the residue was dried at rt in vacuo (20 min), and the obtained solid was dissolved under argon in anhydrous TCE (2 mL) and DIPEA (483 μL, 2.78 mmol, 10 eq.). Then, a solution of amine 22 (632 mg, 1.11 mmol, 4 eq.) in anhydrous TCE (2 mL) was added and the reaction mixture was stirred for 40 min at rt. The reaction mixture was then evaporated in vacuo, redisolved in DCM, adsorbed onto silica (10 g), and the DCM was removed in vacuo. The crude product was purified by flash chromatography on silica (elution with a linear gradient of D1 in DCM, 0-46%) to yield the target compound 23 (346 mg, 67%; $R_f$ 0.66 in D2 on an $NH_3$-pretreated TLC plate, visualization by ninhydrin) as a yellow waxy semi-solid. $^1H$ NMR (600 MHz, $CDCl_3$): δ=5.75, 4.09, 3.21, 2.41, 2.28, 2.22, 2.11, 1.64, 1.62, 1.61, 1.58, 1.54, 1.48, 1.44, 1.42, 1.33, 1.32, 1.29, 1.28, 1.13, 0.89, 0.88 ppm. $^{13}C$ NMR (150.9 MHz, $CDCl_3$): δ=173.92, 173.87, 62.64, 53.90, 44.10, 39.45, 39.14, 35.51, 34.23, 31.86, 29.54, 29.52, 29.09, 27.22, 27.13, 26.77, 24.97, 19.94, 19.47, 14.26 ppm. HRMS (MALDI): m/z calcd. for $C_{111}H_{211}N_6O_{15}$ $[M+H]^+$ 1868.5927; found 1868.5905.

Example 8

Compound 24

N,N'-Diisopropylcarbodiimide (4.07 mL, 24.9 mmol, 1.6 eq.) was added to a solution containing 6-bromo-pentanoic acid (3.00 g, 16.6 mmol), DMAP (81 mg, 0.66 mmol, 0.04 eq.), and geraniol (4.36 mL, 24.9 mmol, 1.5 eq.) in anhydrous DCM (150 mL). The mixture was stirred overnight at rt. The reaction mixture was then adsorbed onto silica (20 g), and the solvents were evaporated in vacuo. The crude product was purified by flash chromatography on silica (120 g, elution with a linear gradient of ethyl acetate in cyclohexane, 0-10%) to yield the target compound 24 (4.80 g, 91%; $R_f$ 0.39 in CE5, visualization by $KMnO_4$) as a pale-yellow oil. $^1$H NMR (400 MHz, $CDCl_3$) δ 5.37-5.30 (m, 1H), 5.11-5.05 (m, 1H), 4.60 (d, J=7.1 Hz, 2H), 3.41 (t, J=6.6 Hz, 2H), 2.35 (t, J=7.2 Hz, 2H), 2.15-2.01 (m, 4H), 1.95-1.86 (m, 2H), 1.83-1.74 (m, 2H), 1.70 (s, 3H), 1.68 (s, 3H), 1.60 (s, 3H).

Compound 26

Bromoester 24 (4.80 g, 15.1 mmol, 2.3 eq.) and potassium carbonate (7.27 g, 52.3 mmol, 8 eq.) were added to a solution of N-Boc-1,6-hexanediamine (1.42 g, 6.58 mmol, 1 eq.) in anhydrous ACN (30 mL), and the mixture was stirred at 45° C. for 24 h. The reaction mixture was then adsorbed onto silica (20 g), and the solvents were evaporated in vacuo. The crude product was purified by flash chromatography on silica (120 g, column pretreated with gaseous $NH_3$, elution with a linear gradient of ethyl acetate in cyclohexane, 0-100%) to yield the compound 25 (2.80 g, 54%; $R_f$ 0.58 in CE50 on an $NH_3$-pretreated TLC plate, visualization by $KMnO_4$) as a pale-yellow oil.

A flask equipped with a magnetic stir bar was loaded with compound 25 (2.80 g, 4.06 mmol), closed with a rubber septum and flushed with argon. ACN (10 mL) and DCM (20 mL) were added through the septum using a needle and syringe, the stirring was turned on and a solution of 4-toluenesulfonic acid monohydrate (2.32 g, 12.2 mmol, 3 eq.) in ACN (20 mL) was added at rt through the septum over the course of 5 min using a needle and syringe. The reaction mixture was stirred at rt for 6 h and was subsequently neutralized using a stream of gaseous ammonia. The reaction mixture was then adsorbed onto silica (20 g) and the crude product was purified by silica gel column chromatography using a linear gradient of D1 in DCM (10-43%). The amine 26 (810 mg, 34%; $R_f$ 0.45 in D2 on an $NH_3$-pretreated TLC plate, visualization by ninhydrin) was obtained as a yellow oil. HRMS (ESI): m/z calcd. for $C_{36}H_{64}N_2O_4$ $[M+H]^+$ 589.4939; found 589.4936.

Hexakis((E)-3,7-dimethylocta-2,6-dien-1-yl) cis,cis-5,5',5'',5''',5'''',5'''''-((((cyclohexane-1,3,5-tricar-bonyl)tris(azanediyl))tris(hexane-6,1-diyl))tris(azanetriyl))hexapentanoate 27

Thionylchloride (700 μL) and DMF (6 μL) were added to cis,cis-cyclohexane-1,3,5-tricarboxylic acid (45 mg, 208 μmol), and the suspension was stirred for 3 h at 70° C. in a closed vial; during this time the suspension turned into a clear solution. Excess $SOCl_2$ was removed at 70° C. with a stream of dry nitrogen, the residue was dried at rt in vacuo (20 min), and the obtained solid was dissolved under argon in anhydrous TCE (1.5 mL) and DIPEA (363 μL, 2.08 mmol, 10 eq.). Then, a solution of amine 26 (490 mg, 833 μmol, 4 eq.) in anhydrous TCE (1.0 mL) was added and the reaction mixture was stirred for 40 min at rt. The reaction mixture was then evaporated in vacuo, redisolved in DCM, adsorbed onto silica (10 g), and the DCM was removed in vacuo. The crude product was purified by flash chromatography on silica (elution with a linear gradient of D1 in DCM, 0-31%) to yield the target compound 27 (262 mg, 65%; $R_f$ 0.59 in D2 on an $NH_3$-pretreated TLC plate, visualization by ninhydrin) as a yellow waxy semi-solid. $^1$H NMR (600 MHz, $CDCl_3$): δ=5.72, 5.32, 5.08, 4.58, 3.21, 2.44, 2.41, 2.32, 2.22, 2.11, 2.10, 2.09, 2.03, 1.69, 1.68, 1.61, 1.60, 1.59, 1.58, 1.47, 1.45, 1.29 ppm. $^{13}$C NMR (150.9 MHz, $CDCl_3$): δ=173.85, 173.60, 142.16, 131.80, 123.72, 118.32, 62.25, 53.79, 53.45, 44.12, 39.52, 39.42, 34.14, 31.85, 29.48, 27.03, 26.72, 26.29, 25.67, 22.90, 17.68, 16.46 ppm. HRMS (MALDI): m/z calcd. For $C_{117}H1_{99}N_6O_{15}$ $[M+H]^+$ 1928.4988; found 1928.4967.

Example 9

Compound 28

N,N'-Diisopropylcarbodiimide (4.07 mL, 24.9 mmol, 1.6 eq.) was added to a solution containing 6-bromo-pentanoic acid (3.00 g, 16.6 mmol), DMAP (81 mg, 0.66 mmol, 0.04 eq.), and nerol (4.38 mL, 24.9 mmol, 1.5 eq.) in anhydrous DCM (60 mL). The mixture was stirred overnight at rt. The reaction mixture was then adsorbed onto silica (20 g), and the solvents were evaporated in vacuo. The crude product was purified by flash chromatography on silica (120 g, elution with a linear gradient of ethyl acetate in cyclohexane, 0-10%) to yield the target compound 28 (4.75 g, 90%; $R_f$ 0.39 in CE5, visualization by $KMnO_4$) as a pale-yellow oil. $^1$H NMR (401 MHz, $CDCl_3$) δ 5.35 (t, J=6.5 Hz, 1H), 5.12-5.06 (m, 1H), 4.57 (dd, J=7.2, 1.1 Hz, 2H), 3.40 (t, J=6.6 Hz, 2H), 2.34 (t, J=7.3 Hz, 2H), 2.15-2.03 (m, 4H), 1.94-1.86 (m, 2H), 1.82-1.74 (m, 5H), 1.68 (d, J=1.4 Hz, 3H), 1.60 (s, 3H).

Compound 30

Bromoester 28 (4.75 g, 15.0 mmol, 2.3 eq.) and potassium carbonate (7.20 g, 52.1 mmol, 8 eq.) were added to a solution of N-Boc-1,6-hexanediamine (1.41 g, 6.51 mmol, 1 eq.) in anhydrous ACN (45 mL), and the mixture was stirred at 48° C. for 24 h. The reaction mixture was then adsorbed onto silica (20 g), and the solvents were evaporated in vacuo. The crude product was purified by flash chromatography on silica (120 g, column pretreated with gaseous $NH_3$, elution with a linear gradient of ethyl acetate in cyclohexane, 0-100%) to yield the compound 29 (3.62 g, 81%; $R_f$ 0.54 in CE50 on an $NH_3$-pretreated TLC plate, visualization by ninhydrin) as a pale-yellow oil.

A flask equipped with a magnetic stir bar was loaded with compound 29 (3.62 g, 5.25 mmol), closed with a rubber septum and flushed with argon. DCM (10 mL) was added through the septum using a needle and syringe, the stirring was turned on and a solution of 4-toluenesulfonic acid monohydrate (2.50 g, 13.1 mmol, 2.5 eq.) in ACN (25 mL) was added at rt through the septum over the course of 5 min using a needle and syringe. The reaction mixture was stirred at rt for 5 h and was subsequently neutralized using a stream of gaseous ammonia. The reaction mixture was then adsorbed onto silica (20 g) and the crude product was purified by silica gel column chromatography using a linear gradient of D1 in DCM (10-43%). The amine 30 (1.36 g, 44%; $R_f$ 0.46 in D2 on an $NH_3$-pretreated TLC plate, visualization by $KMnO_4$) was obtained as a yellow oil. HRMS (ESI): m/z calcd. for $C_{36}H_{64}N_2O_4$ $[M+H]^+$ 589.4939; found 589.4937.

Hexakis((Z)-3,7-dimethylocta-2,6-dien-1-yl) cis,cis-5,5',5",5'",5" ",5""'-((((cyclohexane-1,3,5-tricar-bonyl)tris(azanediyl))tris(hexane-6,1-diyl))tris(azan-etriyl))hexapentanoate 31

Thionylchloride (700 μL) and DMF (6 μL) were added to cis,cis-cyclohexane-1,3,5-tricarboxylic acid (65 mg, 301 μmol), and the suspension was stirred for 3 h at 70° C. in a closed vial; during this time the suspension turned into a clear solution. Excess $SOCl_2$ was removed at 70° C. with a stream of dry nitrogen, the residue was dried at rt in vacuo (20 min), and the obtained solid was dissolved under argon in anhydrous TCE (2 mL) and DIPEA (524 μL, 3.01 mmol, 10 eq.). Then, a solution of amine 30 (796 mg, 1.35 mmol, 4.5 eq.) in anhydrous TCE (2.0 mL) was added and the reaction mixture was stirred for 30 min at rt. The reaction mixture was then evaporated in vacuo, redisolved in DCM, adsorbed onto silica (10 g), and the DCM was removed in vacuo. The crude product was purified by flash chromatography on silica (elution with a linear gradient of D1 in DCM, 5-29%) to yield the target compound 31 (351 mg, 51%) as a yellow waxy semi-solid. $^1H$ NMR (600 MHz, $CDCl_3$): δ=5.69, 5.34, 5.08, 4.55, 3.21, 2.41, 2.38, 2.30, 2.22, 2.10, 2.06, 1.75, 1.67, 1.60, 1.59, 1.58, 1.47, 1.28 ppm. $^{13}C$ NMR (150.9 MHz, $CDCl_3$): δ=173.81, 173.58, 142.44, 132.12, 123.56, 119.22, 60.96, 53.82, 53.48, 44.12, 39.44, 34.17, 32.15, 31.85, 29.50, 27.07, 26.75, 26.63, 25.68, 23.50, 22.91, 17.65 ppm. HRMS (MALDI): m/z calcd. for $C_{117}H_{199}N_6O_{15}$ $[M+H]^+$ 1928.4988; found 1928.4963.

Example 10

Tetra(octan-2-yl) cis,cis-6,6',6",6'"-((((5-(methoxy-carbonyl)cyclohexane-1,3-dicarbonyl) bis (azanediyl))bis(hexane-6,1-diyl))bis(azanetriyl)) tetrahexanoate 32

Thionylchloride (700 μL) and DMF (6 μL) were added to cis,cis-cyclohexane-1,3,5-tricarboxylic acid (60 mg, 278 μmol), and the suspension was stirred for 3 h at 70° C. in a closed vial; during this time the suspension turned into a clear solution. Excess $SOCl_2$ was removed at 70° C. with a stream of dry nitrogen, the residue was dried at rt in vacuo (20 min), and the obtained solid was dissolved under argon in anhydrous TCE (2 mL) and DIPEA (483 μL, 2.78 mmol, 10 eq.). Then, a solution of amine 18 (632 mg, 1.11 mmol, 4 eq.) in anhydrous TCE (1.0 mL) was added and the reaction mixture was stirred for 40 min at rt. The reaction mixture was then evaporated in vacuo, redisolved in DCM, adsorbed onto silica (10 g), and the DCM was removed in vacuo. The crude product was purified by flash chromatography on silica (elution with a linear gradient of D1 in DCM, 5-29%) to yield compound 32 (242 mg, 65%; $R_f$ 0.68 in D2 on an $NH_3$-pretreated TLC plate, visualization by ninhydrin) as a yellow oil. The product 32 is a result of imperfect MeOH removal from amine 18. $^1H$ NMR (600 MHz, $CDCl_3$): δ=5.68, 5.29, 4.88, 3.67, 3.22, 2.43, 2.40, 2.27, 2.20, 2.19, 2.18, 2.09, 1.62, 1.59, 1.57, 1.56, 1.48, 1.47, 1.46, 1.30, 1.28, 1.27,1.19, 0.87 ppm. $^{13}C$ NMR (150.9 MHz, $CDCl_3$): δ=174.64, 173.75, 173.38, 70.83, 53.82, 53.76, 51.84, 43.99, 42.09, 39.43, 35.93, 34.66, 31.81, 31.73, 31.20, 29.50, 29.09, 27.06, 26.72, 25.36, 24.99, 22.56, 20.00, 14.05 ppm.

HRMS (MALDI): m/z calcd. for $C_{78}H_{146}N_4O_{12}$ $[M+H]^+$ 1332.1010; found 1332.0987.

Example 11

Tetrakis(3-methylhexyl) cis,cis-7,7',7",7'"-((((5-(methoxy-carbonyl)cyclohexane-1,3-dicarbonyl) bis(azanediyl))bis (hexane-6,1-diyl))bis(azanetriyl))tetraheptanoate 33

Thionylchloride (700 μL) and DMF (6 μL) were added to cis,cis-cyclohexane-1,3,5-tricarboxylic acid (55 mg, 254 μmol), and the suspension was stirred for 3 h at 70° C. in a closed vial; during this time the suspension turned into a clear solution. Excess $SOCl_2$ was removed at 70° C. with a stream of dry nitrogen, the residue was dried at rt in vacuo (20 min), and the obtained solid was dissolved under argon in anhydrous TCE (2 mL) and DIPEA (443 μL, 2.54 mmol, 10 eq.). Then, a solution of MeOH (10.3 μL, 254 μmol, 1.0 eq.) in TCE (0.5 mL) was added at 0° C. The reaction mixture was allowed to warm to room temperature and after stirring for 1 h, amine 22 (376 mg, 661 μmol, 2.6 eq.) in anhydrous TCE (2.0 mL) was added and the reaction mixture was stirred for 40 min at rt. The reaction mixture was then evaporated in vacuo, redisolved in DCM, adsorbed onto silica (10 g), and the DCM was removed in vacuo. The crude product was purified by flash chromatography on silica (elution with a linear gradient of D1 in DCM, 5-29%) to yield the target compound 33 (87 mg, 26%; $R_f$ 0.75 in D2 on an $NH_3$-pretreated TLC plate, visualization by ninhydrin) as a pale-yellow oil. $^1H$ NMR (600 MHz, $CDCl_3$): δ=5.68, 5.29, 4.09, 3.67, 3.22, 2.43, 2.40, 2.28, 2.20, 2.18, 2.09, 1.64, 1.61, 1.57, 1.53, 1.48, 1.45, 1.42, 1.34, 1.31, 1.28, 1.13, 0.89, 0.88 ppm. $^{13}C$ NMR (150.9 MHz, $CDCl_3$): δ=174.65, 173.91, 173.76, 62.85, 53.85, 51.85, 43.98, 42.09, 39.42, 39.15, 35.52, 34.22, 31.89, 31.19, 29.55, 29.51, 29.06, 27.20, 27.10, 26.72, 24.95, 19.94, 19.47, 14.26 ppm.

HRMS (MALDI): m/z calcd. for $C_{78}H_{147}N^4O_{12}$ $[M+H]^+$ 1332.1010; found 1332.0984.

Example 12

Compound 34

Thionylchloride (1.2 mL) and DMF (10 μL) were added to cis,cis-cyclohexane-1,3,5-tricarboxylic acid (160 mg, 740 μmol), and the suspension was stirred for 3 h at 70° C. in a closed vial; during this time the suspension turned into a clear solution. Excess $SOCl_2$ was removed at 70° C. with a stream of dry nitrogen, the residue was dried at rt in vacuo (20 min), and the obtained solid was dissolved under argon in anhydrous TCE (3 mL) and DIPEA (1.29 mL, 7.40 mmol, 10 eq.). Then, a solution of BnOH (76 μL, 740 μmol, 1.0 eq.) in TCE (0.5 mL) was added at 0° C. The reaction mixture was allowed to warm to room temperature and after stirring for 2 h, amine 18 (1.09 g, 1.92 mmol, 2.6 eq.) in anhydrous TCE (3.0 mL) was added and the reaction mixture was stirred for 40 min at rt. The reaction mixture was then evaporated in vacuo, redisolved in DCM, adsorbed onto silica (10 g), and the DCM was removed in vacuo. The crude product was purified by flash chromatography on silica (elution with a linear gradient of D1 in DCM, 5-29%) to yield the compound 34 (150 mg, 14%; $R_f$ 0.67 in D2 on an $NH_3$-pretreated TLC plate, visualization by ninhydrin) as a pale-yellow oil. HRMS (MALDI): m/z calcd. for $C_{84}H_{15}$, $N_4O_{12}$ $[M+H]^+$ 1408.1323; found 1408.1283.

cis,cis-3,5-Bis((6-(bis(6-(octan-2-yloxy)-6-oxohexyl)amino)hexyl)carbamoyl)cyclohexane-1-carboxylic acid 35

A pear-shaped flask was equipped with a magnetic stir bar and loaded with palladium on carbon (10% Pd/C, 25 mg). The flask was closed with a rubber septum, connected to a Schlenk line via a needle, and the atmosphere in the flask was exchanged for argon via 3 cycles of vac-Ar. Subsequently, a solution of compound 34 (150 mg, 107 μmol) in MeOH (3 mL) was added through the septum using a needle and syringe and the stirring was turned on. The flask was connected to a continuous stream of hydrogen using a second needle and the main argon inlet into the Schlenk line was closed (excess hydrogen continuously released from the flask through the Schlenk line bubbler). The reaction mixture was vigorously stirred for 4 h at rt. Then the flask was thoroughly flushed with argon and the palladium on carbon was removed by filtering through a PTFE syringe filter. The volatiles were then removed in vacuo yielding the product 35 (110 mg, 79%, $R_f$ 0.27 in D2 on an $NH_3$-pretreated TLC plate, visualization by ninhydrin) as a colorless oil. $^1H$ NMR (600 MHz, $CDCl_3$): δ=6.59, 4.88, 3.20, 3.15, 2.71, 2.67, 2.27, 2.24, 2.20, 2.13, 2.02, 1.64, 1.63, 1.60, 1.58, 1.57, 1.56, 1.54, 1.47, 1.45, 1.32, 1.28, 1.27, 1.26, 1.18, 0.87 ppm. $^{13}C$ NMR (150.9 MHz, $CDCl_3$): δ=180.09, 175.19, 173.10, 70.94, 53.01, 52.06, 44.36, 44.32, 39.22, 35.91, 34.43, 32.48, 32.16, 31.72, 29.15, 29.08, 26.72, 26.62, 26.30 25.36, 24.69, 24.11, 22.55, 19.99, 14.06 ppm. HRMS (MALDI): m/z calcd. for $C_{77}H_{145}N_4O_{12}$ $[M+H]^+$ 1318.0854; found 1318.0842.

Tetra(octan-2-yl) cis,cis-6,6',6",6'"-((((5-(pyrrolidine-1-carbonyl)cyclohexane-1,3-dicarbonyl) bis(azanediyl))bis(hexane-6,1-diyl))bis(azanetriyl))tetrahexanoate 36

A vial equipped with a magnetic stir bar was was loaded with compound 35 (60 mg, 45.5 μmol), $NH_4Cl$ (12.2 mg, 228 μmol, 5 eq.), and flushed with argon via piercing the septum with a needle. Subsequently, anhydrous DMF (1.5 mL) and DIPEA (48 μL, 273 μmol, 6 eq.) were added using a needle and syringe. The resulting suspension was stirred for 10 min at rt, then a solution of PyBroP (53 mg, 114 μmol, 2.5 eq.) in anhydrous DMF (0.5 mL) was added and the reaction mixture was stirred at rt for 90 min. The reaction mixture was then evaporated in vacuo, redisolved in DCM, adsorbed onto silica (10 g), and the DCM was removed in vacuo. The crude product was purified by flash chromatography on silica (elution with a linear gradient of D1 in DCM, 5-29%) to yield the compound 36 (18 mg, 29%; $R_f$ 0.42 in D2 on an $NH_3$-pretreated TLC plate, visualization by ninhydrin) as the main product in the form of a pale-yellow oil. The compound 36 is a product of pyrrolidine impurity in PyBroP resulting from PyBroP hydrolysis. $^1H$ NMR (600 MHz, $CDCl_3$): δ=6.08, 4.88, 3.48, 3.43, 3.35, 3.25, 3.26, 3.20, 3.16, 2.72, 2.50, 2.32, 2.28, 2.15, 1.98, 1.95, 1.85, 1.69, 1.68, 1.66, 1.65, 1.60, 1.57, 1.50, 1.46, 1.34, 1.28, 1.26, 1.19, 0.88 ppm. $^{13}C$ NMR (150.9 MHz, $CDCl_3$): δ=174.39, 173.14, 172.79, 70.97, 53.37, 47.44, 47.40, 47.22, 47.19, 46.43, 46.30, 46.27, 45.90, 44.03, 41.39, 39.09, 35.92, 34.44, 32.08, 31.73, 31.20, 29.10, 26.70, 26.14, 25.37, 24.69, 24.24, 22.57, 20.00, 14.06. HRMS (MALDI): m/z calcd. for $C_{81}H_{152}N_5O_{11}$ $[M+H]^+$ 1371.1483; found 1371.1467.

Example 13

Trimethyl cis,cis-1,3,5-cyclohexanetricarboxylate 37

To a solution of cis,cis-1,3,5-cyclohexanetricarboxylic acid (9.90 g, 45.8 mmol) in anhydrous methanol (150 mL) placed in a round-bottom flask equipped with a calcium chloride drying tube and magnetic stirrer was slowly added thionyl chloride (15.29 mL, 210.8 mmol, 4.6 eq.) through a rubber septum via syringe. After the violent exothermic reaction ceased, the solution was stirred at room temperature for 12 h. The solvent was then removed in vacuo, the oily residue was poured into a 500 mL separatory flask, diluted with saturated aqueous $NaHCO_3$ (250 mL), and the product was extracted with diethyl ether (2×100 mL). The combined organic phase was washed with brine (100 mL), dried over anhydrous sodium sulfate, filtered through an S2 sintered glass, and the solvents were evaporated in an RVE to give 37 as a pale-yellow oil. $^1H$ NMR (400 MHz, $CDCl_3$): δ=3.68 (s, 9H), 2.44-2.32 (m, 3H), 2.31-2.21 (m, 3H), 1.59-1.45 (m, 3H) ppm. HRMS (ESI): m/z calculated for $C_{12}H_{19}O_6[M+H]^+$ 259.11761; found 259.11766.

Trimethyl cis,cis-1,3,5-trimethylcyclohexane-1,3,5-tricarboxylate 38

Diisopropylamine was distilled from sodium hydroxide before use. A solution of diisopropylamine (2.19 mL, 15.5 mmol, 4 eq.) in anhydrous diethyl ether (10 mL) was added dropwise to the solution of 2.0 M n-butyllithium (7.74 mL, 15.5 mmol, 4 eq.) at 0° C. to generate lithium diisopropylamide in situ. A solution of 37 (1.00 g, 3.87 mmol; 1 eq.) in anhydrous diethyl ether (10 mL) was added dropwise to the reaction solution at 0° C., and the mixture was stirred for 2 h at 0° C. Dimethyl sulfate (2.20 mL, 23.2 mmol, 6 eq.) was added, and the stirring continued overnight at rt. The product was washed with water, 1 M HCl and brine, dried over sodium sulfate, filtered through an S2 sintered glass, and the solvents were evaporated in an RVE. GC-MS analysis exhibited that ratio of two isomers cis, cis/cis, trans=7:1 in the crude product. The fractional crystallization in the mixture of diethyl ether and pentane afforded cis, cis isomer 38 (225 mg, 19%) as white crystals. $^1H$ NMR (400 MHz, $CDCl_3$): δ=3.65 (s, 9H), 2.74 (d, J=13.4 Hz, 3H), 1.21 (s, 9H), 0.97 (d, J=14.8 Hz, 3H) ppm. HRMS (EI): m/z calcd. for $C_{15}H_{24}O_6[M]^+$300.1567; found 300.1565.

cis,cis-1,3,5-Trimethylcyclohexane-1,3,5-tricarboxylic acid 39

Trimethyl cis,cis-1,3,5-trimethylcyclohexane-1,3,5-tricarboxylate 38 (220 mg, 0.73 mmol, 1 eq.) was dissolved in methanol (3.0 mL). A solution of lithium hydroxide monohydrate (369 mg, 6.59 mmol, 9 eq.) in water (2.0 mL) was added, and the reaction mixture was stirred at rt overnight. Methanol was removed by evaporation in an RVE. The solution was cooled in an ice bath, and the pH was adjusted to 1 with concentrated HCl. A white precipitate formed immediately and was collected by suction filtration to yield 39 (60 mg, 32%). $^1H$ NMR (400 MHz, DMSO-d6): δ=11.96 (br s, 3H), 2.52 (d, 3H, partial overlap with solvent signal), 1.20 (d, J=14.7 Hz, 3H), 1.19 (s, 9H) ppm.

Hexakis(3-methylhexyl) cis,cis-7,7',7",7'",7" ",7""'-((((1,3,5-trimethylcyclohexane-1,3,5-tricar-bonyl)tris(azanediyl))tris(hexane-6,1-diyl))tris(azanetriyl))hexaheptanoate 40

Thionylchloride (0.50 mL) and DMF (2 μL) was added to cis,cis-1,3,5-trimethylcyclohexane-1,3,5-tricarboxylic acid 39 (34 mg, 0.13 mmol), and the suspension was stirred overnight at 70° C. in a closed vial. Excessive $SOCl_2$ was blown out with a stream of dry nitrogen, the residue was dried in vacuo (10 min), and after cooling down to rt the residue was dissolved in anhydrous TCE (0.5 mL). Then, a solution of amine 22 (337 mg, 0.59 mmol, 4.5 eq.) and DIPEA (229 μL, 1.32 mmol, 10 eq.) in anhydrous TCE (1.00 mL) was added, and the reaction mixture was stirred for 15 min at rt. The reaction mixture was then adsorbed onto silica (4 g), and the solvents were evaporated in vacuo. The crude product was purified by flash chromatography on silica (40 g, elution with a linear gradient of D1 in DCM, 0-30%) to yield the target compound 40 (6 mg, 5%; $R_f$ 0.26 in D4, visualization by ninhydrin) as a viscous pale-yellow oil. HRMS (MALDI): m/z calcd. for $C_{114}H_{216}N_6O_{15}$ $[M+H]^+$ 1910.6396; found 1910.6368.

Example 14

Hexa(octan-2-yl) cis,cis-6,6',6",6"',6"",6""'-((((1,3,5-trimethylcyclohexane-1,3,5-tricarbonyl) tris (azanediyl))tris(hexane-6,1-diyl))tris(azanetriyl)) hexahexanoate 41 and cis,cis-3,5-Bis((6-(bis(6-(octan-2-yloxy)-6-oxohexyl)amino)hexyl) carbamoyl)-1,3,5-trimethylcyclohexane-1-carboxylic acid 42

Thionylchloride (0.50 mL) and DMF (2 μL) was added to 39 (28 mg, 0.11 mmol), and the suspension was stirred for 2 h at 70° C. in a closed vial. Excessive $SOCl_2$ was blown out with a stream of dry nitrogen, the residue was dried in vacuo (10 min), and after cooling down to rt the residue was dissolved in anhydrous TCE (0.25 mL). Then, a solution of amine 18 (278 mg, 0.49 mmol, 4.5 eq.) and DIPEA (180 μL, 1.08 mmol, 10 eq.) in anhydrous TCE (0.75 mL) was added, and the reaction mixture was stirred for 15 min at rt. The reaction mixture was then adsorbed onto silica (4 g), and the solvents were evaporated in vacuo. The crude product was purified by flash chromatography on silica (40 g, elution with a linear gradient of D1 in DCM, 0-30%) to yield the target compound 41 (49 mg, 24%; $R_f$ 0.30 in D4, visualization by ninhydrin) as a viscous pale-yellow oil and compound 42 (52 mg, 45%; $R_f$ 0.28 in D4, visualization by ninhydrin) as a pale-yellow oil.

41 $^1$H NMR (600 MHz, $CDCl_3$): δ=7.98, 4.88, 3.12, 2.88, 2.75, 2.68, 2.27, 1.64, 1.56, 1.46, 1.45, 1.28, 1.27, 1.26, 1.23, 1.19, 1.12, 0.87 ppm. $^{13}$C NMR (150.9 MHz, $CDCl_3$): δ=184.26, 177.45, 173.06, 70.96, 52.45, 51.68, 43.03, 43.00, 42.38, 38.83, 35.92, 34.43, 34.17, 33.21, 31.72, 29.08, 28.95, 22.56, 19.99, 14.05 ppm. HRMS (MALDI): m/z calcd. for $C_{114}H_{216}N_6O_{151}$ $[M+H]^+$ 1910.6396; found 1910.6364. 42 HRMS (MALDI): m/z calcd. for $C_{80}H_{150}N_4O_{12}$ $[M+H]^+$ 1360.1323; found 1360.1875.

Example 15

Trimethyl cis,cis-1,3,5-tris((benzyloxy)methyl)cyclohexane-1,3,5-tricarboxylate 43

Diisopropylamine was distilled from sodium hydroxide before use. A solution of diisopropylamine (6.56 mL, 46.5 mmol, 4 eq.) in anhydrous diethyl ether (30 mL) was added dropwise to the solution of 2.0 M n-butyllithium (23.2 mL, 46.5 mmol, 4 eq.) at 0° C. to generate lithium diisopropylamide in situ. A solution of trimethyl cyclohexane-1,3,5-tricarboxylate 37 (3.00 g, 11.6 mmol; 1 equiv.) in anhydrous diethyl ether (30 mL) was added dropwise to the reaction solution at 0° C., and the mixture was stirred for 2 h at 0° C. Benzyl chloromethyl ether (9.69 mL, 69.7 mmol, 6 eq.) was added, and the stirring continued over-night at rt. The product was washed with water, 1 M HCl and brine, dried over sodium sulphate, filtered through an S2 sintered glass, and the solvent was evaporated in an RVE. The crude product was purified by flash chromatography on silica (200 g, elution with a linear gradient of ethyl acetate in cyclohexane, 0-20%). The fractional crystallization in the mixture of diethyl ether (3.0 mL) and pentane (18.0 mL) afforded cis, cis isomer 43 (1.52 mg, 22%) as white crystals. $^1$H NMR (400 MHz, $CDCl_3$): δ=7.36-7.22 (m, 15H, partial overlap with solvent signal), 4.46 (s, 6H), 3.69 (s, 9H), 3.39 (s, 6H), 2.68 (d, J=14.2 Hz, 3H), 1.18 (d, J=14.9 Hz, 3H) ppm. HRMS (ESI): m/z calcd. for $C_{36}H_{42}O_9[M+Na]^+$ 641.2721; found 641.2719.

cis,cis-1,3,5-Tris((benzyloxy)methyl)cyclohexane-1,3,5-tricarboxylic acid 44

Compound 43 (250 mg, 0.40 mmol, 1 eq.) was dissolved in methanol (4.0 mL). A solution of lithium hydroxide monohydrate (152 mg, 3.64 mmol, 9 eq.) in water (2.0 mL) was added, and the reaction mixture was stirred at rt overnight. Methanol was removed by evaporation in an RVE. The solution was cooled in an ice bath, and the pH was adjusted to 1 with concentrated HCl. A white precipitate formed immediately and was collected by suction filtration to yield 44 (200 mg, 86%). $^1$H NMR (400 MHz, DMSO-d6): δ=12.12 (br s, 3H), 7.37-7.18 (m, 15H), 4.39 (s, 6H), 3.39 (s, 6H), 2.36 (d, J=14.9 Hz, 3H), ppm.

Tetra(octan-2-yl) cis,cis-6,6',6",6"'-((((1,3,5-tris ((benzyloxy)methyl)-5-(bis(6-(octan-2-yloxy)-6-oxohexyl)carbamoyl)cyclohexane-1,3-dicarbonyl)bis (azanediyl))bis(hexane-6,1-diyl)) bis(azanetriyl)) tetrahexanoate 45 and cis,cis-1,3,5-Tris((benzyloxy) methyl)-3,5-bis((6-(bis(6-(octan-2-yloxy)-6-oxohexyl)amino)hexyl)carbamoyl)cyclohexane-1-carboxylic acid 46

Thionylchloride (0.50 mL) and DMF (2 μL) was added to 44 (100 mg, 0.17 mmol, 1 eq.), and the suspension was stirred overnight at 70° C. in a closed vial. Excessive $SOCl_2$ was blown out with a stream of dry nitrogen, the residue was dried in vacuo (10 min), and after cooling down to rt the residue was dissolved in anhydrous TCE (0.5 mL). Then, a solution of amine 18 (444 mg, 0.78 mmol, 4.5 eq.) and DIPEA (302 μL, 1.73 mmol, 10 eq.) in anhydrous TCE (1.50 mL) was added, and the reaction mixture was stirred for 15 min at rt. The reaction mixture was then adsorbed onto silica (4 g), and the solvent was evaporated in vacuo. The crude product was purified by flash chromatography on silica (80 g, elution with a linear gradient of D1 in DCM, 0-20%) to yield the target compound 45 (46 mg, 12%; $R_f$ 0.46 in D4, visualization by ninhydrin) as a viscous pale-yellow oil and compound 46 (37 mg, 13%; $R_f$ 0.39 in D4, visualization by ninhy-drin) as a pale-yellow oil.

45 HRMS (MALDI): m/z calcd. for $C_{135}H_{234}N_6O_{18}$ $[M+H]^+$ 2228.7652; found 2228.7702.

46 HRMS (MALDI): m/z calcd. for $C_{101}H_{168}N_4O_{15}$ $[M]^+$1677.2506; found 1677.2479.

Hexa(octan-2-yl) cis,cis-6,6',6",6"',6"",6""'-((((1,3,5-tris(hydroxymethyl)cyclohexane-1,3,5-tricar-bonyl) tris(azanediyl))tris(hexane-6,1-diyl))tris(azanetriyl)) hexahexanoate 47

Following the procedure outlined for 35, the target compound 47 was prepared from lipidoid 45 (20 mg, 0.008 mmol, 1 eq.), palladium on carbon (10% Pd/C, 19 mg, 0.018 mmol, 2 eq.) and acetic acid (80 μL, 1.73 mmol) to yield lipidoid 47 (5 mg, 30%) as a thick pale-yellow oil. HRMS (MALDI): m/z calcd. for $C_{114}H_{216}N_6O_{18}$ $[M+H]^+$ 1958.6244; found 1958.6314.

cis,cis-3,5-Bis((6-(bis(6-(octan-2-yloxy)-6-oxo-hexyl)amino)hexyl)carbamoyl)-1,3,5-tris(hy-droxyme-thyl)cyclohexane-1-carboxylic acid 48

Following the procedure outlined for 35, the target compound 48 was prepared from lipidoid 46 (15 mg, 0.009 mmol, 1 eq.), palladium on carbon (19 mg, 0.018 mmol, 2 eq.) and acetic acid (80 μL, 1.73 mmol) to yield lipidoid 48 (7 mg, 59%) as athick pale-yellow oil. HRMS (MALDI): m/z calcd. for $C_{80}H_{150}N_4O_{15}$ $[M]^+$1407.1098; found 1407.1042.

Example 16

Tetra(octan-2-yl) cis,cis-6,6',6",6'"-((((1,3,5-tris ((benzyloxy)methyl)-5-(pyrrolidine-1-carbonyl) cy-clohexane-1,3-dicarbonyl)bis(azanediyl))bis (hexane-6,1-diyl))bis(azanetriyl))tetrahexanoate 49

Compound 44 (100 mg, 0.17 mmol, 1 eq.) was dissolved in anhydrous DMF (1.0 mL) and DMAP (3 mg, 0.02 mmol, 0.15 eq.) and DIPEA (450 μL, 2.60 mmol, 10 eq.) were added. A solution of PyBroP (363 mg, 0.78 mmol, 4.5 eq.) in anhydrous DMF (1.0 mL) was added dropwise, and the reaction mixture was stirred for 1.5 h at rt under argon atmosphere. Then, a solution of amine 18 (444 mg, 0.78 mmol, 4.5 eq.) in anhydrous DMF (1.0 mL) was added, and the reaction mixture was stirred for 1 h at rt under argon atmosphere. The reaction mixture was then adsorbed onto silica (4 g), and the solvent was evaporated in vacuo. The crude product was purified by flash chromatography on silica (80 g, elution with a linear gradient of D1 in DCM, 0-30%) to yield the target compound 49 (146 mg, 51%; $R_f$ 0.58 in D3, visualization by ninhydrin) as a pale-yellow oil. HRMS (MALDI): m/z calcd. for $C_{105}H_{175}N_5O_{14}$ $[M+Na]^+$ 1753.3028; found 1753.3044.

Tetra(octan-2-yl) cis,cis-6,6',6",6'"-((((1,3,5-tris(hy-droxymethyl)-5-(pyrrolidine-1-carbonyl)cyclo-hexane-1,3-dicarbonyl)bis(azanediyl))bis(hexane-6, 1-diyl))bis(azanetriyl))tetrahexanoate 50

Following the procedure outlined for 35, the target compound 50 was prepared from lipidoid 49 (70 mg, 0.04 mmol, 1 eq.), palladium on carbon (86 mg, 0.40 mmol, 2 eq.) and acetic acid (80 μL, 1.73 mmol) to yield lipidoid 50 (57 mg, 96%) as a thick pale-yellow oil. HRMS (MALDI): m/z calcd. for $C_{84}H_{157}N_5O_{14}$ $[M+Na]^+$1483.1619; found 1483.1656.

Example 17 cis,cis-$N^1$,$N^7$-Bis(6-(didodecylamino)hexyl)-5,7-bis (hydroxymethyl)-4-oxo-3-oxabicyclo [3.3.1]nonane-1,7-dicarboxamide 52

PyBroP (0.323 g, 0.694 mmol, 5 eq.), N,N-diisopropyl-ethylamine (DIPEA, 0.483 mL, 2.77 mmol, 20 eq.) and amine 10 (0.314 g, 0.694 mmol, 5 eq.) were added to a solution of triacid 44 (80 mg, 0.139 mmol) in anhydrous TCE (4 mL), and the reaction mixture was stirred at rt for 12 h. The reaction mixture was then adsorbed onto silica (10 g), and the solvents were evaporated in vacuo. The crude product was purified by silica gel column chromatography using a linear gradient of D1 in DCM (20-80%). Diamide 51 (16 mg, 8.0%; $R_f$0.56 in mobile phase D3, detection with ninhydrin) was obtained in the form of a viscous yellowish oil.

Palladium on charcoal (10%) was added to a solution of diamide 51 in a methanol-ethyl acetate mixture (10+10 mL) under argon atmosphere. The reaction mixture was then stirred under hydrogen atmosphere at rt for 12 h. The suspension was filtered through a pad of celite and evaporated to yield lipidoid 52 as a colorless oil (5.5 mg, 42.9%, $R_f$0.61 in mobile phase D3, detection with ninhydrin) HRMS (MALDI): m/z calcd. for $C_{72}H_{141}N^4O_6$ $[M+H]^+$ 1158.0846; found 1158.0822.

Example 18

6-(Didodecylamino)hexanoic acid 53

A 500 mL round-bottom flask equipped with a calcium chloride drying tube and magnetic stirrer was filled with a solution of 6-aminohexanoic acid (2.00 g, 15.2 mmol) in ACN (150 mL), and sodium triacetoxyborohydride (12.93 g, 61.0 mmol, 4 eq.) was added. With intensive stirring, n-dodecylaldehyde (10.16 mL, 45.7 mmol, 3 eq.) was slowly added through a rubber septum via syringe, and the resulting white suspension was stirred at room temperature for 5 d. The reaction mixture was then adsorbed onto silica (25 g), and the solvents were evaporated in vacuo. The crude product was purified by silica gel column chromatography using a linear gradient of D1 in DCM (0-100%). Amino acid 53 (3.203 g, 44.9%) was obtained as a colourless oil. $^1H$ NMR (400 MHz, $CDCl_3$): δ=2.88-2.84 (m, 6H), 2.24 (t, 2H), 1.62-1.72 (m, 2H), 1.42-1.26 (m, 44H) 0.89 (t, 6H) ppm. $^{13}C$ NMR (150.9 MHz, $CDCl_3$): δ=178.65, 51.37, 36.22, 31.90, 29.61-29.20, 27.07, 26.74, 25.45, 23.78, 23.31, 22.67, 14.10 ppm. HRMS (ESI): m/z calculated for $C_{30}H_{60}O_2N$ $[M-H]^-$ 466.46295; found 466.46286.

cis,cis-1,3,5-Triaminocyclohexane trihydrobromide 55

The synthesis was carried out according to Bowen, T. et al., Bioorganic & Medicinal Chemistry Letters, Vol. 6, No. 7, 1996, 807-810 and slightly modified. cis,cis-1,3,5-Cyclohexanetricarboxylic acid (2.0 g, 9.25 mmol) was suspended in toluene (75 mL), and DIPEA (4.83 mL, 27.75 mmol, 3 eq.) was added followed by diphenyl phosphoryl azide (5.97 mL, 27.75 mmol, 3 eq.). The mixture was stirred for 0.5 h at rt and then heated to 90° C. for 0.5 h. Benzyl alcohol (3.20 mL, 30.81 mmol, 3.33 eq.) was added and the solution was heated to 90° C. for 18 h. After cooling to rt, the product was collected by vacuum filtration, washed with minimal cold toluene, and dried under vacuum to yield 0.386 g (7.85%) of cis,cis-1,3,5-tri(N-benzyloxycarbonyl)cyclohexane 54.

Compound 54 (0.386 g, 0.726 mmol) was suspended in a 33% solution of HBr in acetic acid (5 mL), and stirred for 12 h at rt. The yellow suspension was then diluted with diethyl ether (20 mL), and filtered through an S2 sintered glass to give trihydrobromide 55 as a yellow solid (0.248 g, 91.8%).

cis,cis-N,N',N"-(Cyclohexane-1,3,5-triyl)tris(6-(di-dodecylamino)hexanamide) 56

PyBroP (0.752 g, 1.61 mmol, 6 eq.), DIPEA (0.937 mL, 5.38 mmol, 20 eq.) and acid 53 (0.755 g, 1.61 mmol, 6 eq.)

were added to a solution of triamine salt 55 (0.100 g, 0.269 mmol) in a mixture of anhydrous TCE (3 mL) and anhydrous DMF (3 mL), and the reaction mixture was stirred at rt for 12 h. The reaction mixture was then adsorbed onto silica (10 g), and the solvents were evaporated in vacuo. The crude product was purified by silica gel column chromatography using a linear gradient of D1 in DCM (20-30%). Lipidoid 56 (113 mg, 28.4%; $R_f$ 0.65 in mobile phase D2, detection with ninhydrin) was obtained in the form of a viscous yellowish oil. HRMS (ESI): m/z calculated for $C_{96}H_{193}O_6N_3$ $[M+H]^+$ 1478.5134; found 1478.5162.

Example 19

Preparation of Transfection Reagents

Reagents were generated by mixing the individual components listed in Table 1 up to Table 4. All tables contain the final molar concentrations in the transfection reagent. Stock 5 mM solutions of the individual components in 99.7% ethanol (v/v) were used for the preparation of A01 to A16, A21, A22, A24, A28, and A29. Stock 5 mM solutions of lipidoids, DOPE and DMG-PEG2000, and stock 10 mM solution of cholesterol, all in 99.7% ethanol (v/v) were used for the preparation of A17 to A20, A23, and A25 to A27. The DOPE-Cy5 stock solution had a concentration of 0.79 mM and was prepared in chloroform. TT3 is a lipid according to WO 2016/187531, used herein for comparison. Benchmark D-Lin-MC3-DMA lipid (Med-ChemExpress Europe) was also used for comparison.

TABLE 1

Composition of transfection reagents A01-A06.

| Compound | Concentration of individual components in Transfection reagents (mM) | | | | | |
|---|---|---|---|---|---|---|
| | A01 | A02 | A03 | A04 | A05 | A06 |
| 3 | 1.1 | — | — | — | — | — |
| 7 | — | 1.1 | — | — | — | — |
| 8 | — | — | 1.1 | — | — | — |
| 11 | — | — | — | 1.1 | — | — |
| 15 | — | — | — | — | 1.1 | — |
| TT3 | — | — | — | — | — | 1.1 |
| cholesterol | 2.18 | 2.18 | 2.18 | 2.18 | 2.18 | 2.18 |
| DOPE | 1.64 | 1.64 | 1.64 | 1.64 | 1.64 | 1.64 |
| $DMG-PEG_{2000}$ | 0.075 | 0.075 | 0.075 | 0.075 | 0.075 | 0.075 |

TABLE 2

Composition of transfection reagents A07-A12.

| Compound | Concentration of individual components in transfection reagents (mM) | | | | | |
|---|---|---|---|---|---|---|
| | A07 | A08 | A09 | A10 | A11 | A12 |
| 3 | 1.1 | — | — | — | — | — |
| 7 | — | 1.1 | — | — | — | — |
| 8 | — | — | 1.1 | — | — | — |
| 11 | — | — | — | 1.1 | — | — |
| 15 | — | — | — | — | 1.1 | — |
| TT3 | — | — | — | — | — | 1.1 |
| cholesterol | 2.18 | 2.18 | 2.18 | 2.18 | 2.18 | 2.18 |
| DOPE | 1.64 | 1.64 | 1.64 | 1.64 | 1.64 | 1.64 |
| $DMG-PEG_{2000}$ | 0.075 | 0.075 | 0.075 | 0.075 | 0.075 | 0.075 |
| DOPE-Cy5 | $1.19 \times 10^{-3}$ | $1.19 \times 10^{-3}$ | $1.19 \times 10^{-3}$ | $1.19 \times 10^{-3}$ | $1.19 \times 10^{-3}$ | $1.19 \times 10^{-3}$ |

TABLE 3

Composition of transfection reagents A13-A22.

| Compound | Concentration of individual components in transfection reagents (mM) | | | | | | | | | |
|---|---|---|---|---|---|---|---|---|---|---|
| | A13 | A14 | A15 | A16 | A17 | A18 | A19 | A20 | A21 | A22 |
| 19 | 1.1 | — | — | — | — | — | — | — | — | — |
| 23 | — | 1.1 | — | — | — | — | — | — | — | — |
| 27 | — | — | 1.1 | — | — | — | — | — | — | — |
| 31 | — | — | — | 1.1 | — | — | — | — | — | — |
| 32 | — | — | — | — | 1.64 | — | — | — | — | — |
| 33 | — | — | — | — | — | 1.64 | — | — | — | — |
| 35 | — | — | — | — | — | — | 1.64 | — | — | — |
| 36 | — | — | — | — | — | — | — | 1.64 | — | — |
| 40 | — | — | — | — | — | — | — | — | 1.1 | — |
| 41 | — | — | — | — | — | — | — | — | — | 1.1 |
| cholesterol | 2.18 | 2.18 | 2.18 | 2.18 | 2.18 | 2.18 | 2.18 | 2.18 | 2.18 | 2.18 |
| DOPE | 1.64 | 1.64 | 1.64 | 1.64 | 1.64 | 1.64 | 1.64 | 1.64 | 1.64 | 1.64 |
| $DMG-PEG_{2000}$ | 0.075 | 0.075 | 0.075 | 0.075 | 0.075 | 0.075 | 0.075 | 0.075 | 0.075 | 0.075 |

TABLE 4

| Composition of transfection reagents A23-A29. | | | | | | | |
|---|---|---|---|---|---|---|---|
| | Concentration of individual components in transfection reagents (mM) | | | | | | |
| Compound | A23 | A24 | A25 | A26 | A27 | A28 | A29 |
| 42 | 1.64 | — | — | — | — | — | — |
| 47 | — | 1.1 | — | — | — | — | — |
| 48 | — | — | 1.64 | — | — | — | — |
| 50 | — | — | — | 1.64 | — | — | — |
| 52 | — | — | — | — | 1.64 | — | — |
| 56 | — | — | — | — | — | 1.1 | — |
| D-Lin-MC3-DMA | — | — | — | — | — | — | 2.5 |
| cholesterol | 2.18 | 2.18 | 2.18 | 2.18 | 2.18 | 2.18 | 1.93 |
| DOPE | 1.64 | 1.64 | 1.64 | 1.64 | 1.64 | 1.64 | — |
| DSPC | — | — | — | — | — | — | 0.5 |
| DMG-$PEG_{2000}$ | 0.075 | 0.075 | 0.075 | 0.075 | 0.075 | 0.075 | 0.075 |

Example 20

Preparation of Lipid Nanoparticles (LNP) Containing Nucleic Acids

The siRNA-containing LNPs (siRNA-LNPs) were prepared as follows: 300 μl of a solution of each of the A01-A06 transfection reagents prepared in Example 19 was mixed with a solution of 1.2 nmol siRNA (catalog number 4392420, Ambion) in 300 1d 10 mM citrate buffer (pH 3.0) using a "Y" microfluidic device with two inputs and one output for sampling. The lipid mixture and the siRNA solution were injected sep-arately into each inlet by a linear pump at a constant flow rate of 300 l/min. The resulting 600 1d nanoparticle solution was collected and immediately diluted by the addition of 600 μl PBS; the corresponding nanoparticle samples designated B01-B06 were thus formed from the transfection reagents A01-A06. DNA encoding the fluorescent protein mKate2 was amplified from the plasmid pmKate2-C(Evrogen) using the primers (5'-ATCAA-CATATGGTGAGCGAGCTG-3' (SEQ ID NO. 1); 5'-AAGAATTCCTATCATCTGTGCCCCAG-3' (SEQ ID NO. 2)) and cloned into the pET24a vector (Invitrogen) under the T7 promoter. Messenger RNA (mRNA) encoding mKate2 was transcribed in vitro using the Ampliscribe T7-Flash transcription kit (Lucigen) according to the manufacturer's protocol. The RNA cap analog ARCA (Jena Bioscience) was added to the in vitro transcription reaction, and the poly(A) terminus was synthesized using poly(A) polymerase (New England Biolabs) according to the standard protocol.

The mRNA-containing LNPs (mRNA-LNPs) were prepared as follows: 300 μl of a solution of each of the A07-A29 transfection reagents prepared in Example 19 were mixed with a solution of 120 μg of mRNA in 300 1d of 10 mM citrate buffer (pH 3.0), the preparation was then analogous to siRNA-LNP. Thus, the corresponding nanoparticle samples designated B07-B29 were generated from the transfection reagents A07-A29. Nanoparticle samples designated B08a and B11a were generated from the transfection reagents A02 and A05, respectively.

Each of the LNP samples (B01-B29) was prepared in triplicate. The hydrodynamic diameter of freshly formed LNPs was measured using dynamic light scattering (NanoZS Zetasizer, Malvern, Worcestershire, UK) at a scattering angle of 1730 at 25° C. The hydrodynamic diameter of siRNA-LNPs ranged from 67 to 110 nm, and the hydrodynamic diameter of mRNA-LNPs ranged from 82 to 288 nm (Tab. 5). In this form, the particles were used for subsequent biological tests.

TABLE 5

| Hydrodynamic diameter of LNPs including standard deviation measured by dynamic light scattering. | |
|---|---|
| LNP | Diameter (nm) |
| B01 | 83.3 ± 4.0 |
| B02 | 109.9 ± 12.7 |
| B03 | 100.1 ± 6.3 |
| B04 | 81.7 ± 8.8 |
| B05 | 72.3 ± 13.2 |
| B06 | 67.1 ± 3.5 |
| B07 | 90.4 ± 1.3 |
| B08 | 153.5 ± 11.9 |
| B09 | 117.0 ± 7.6 |
| B10 | 90.5 ± 3.9 |
| B11 | 157.7 ± 3.5 |
| B12 | 81.5 ± 5.4 |
| B13 | 174.3 ± 7.8 |
| B14 | 144.6 ± 17.8 |
| B15 | 124.5 ± 14.3 |
| B16 | 143.2 ± 6.2 |
| B17 | 190.8 ± 2.5 |
| B18 | 190.4 ± 2.1 |
| B19 | 194.8 ± 5.2 |
| B20 | 194.4 ± 6.2 |
| B21 | 179.4 ± 10.5 |
| B22 | 261.0 ± 11.4 |
| B23 | 221.0 ± 12.7 |
| B24 | 217.1 ± 13.8 |
| B25 | 287.8 ± 10.5 |
| B26 | 165.1 ± 11.9 |
| B27 | 242.1 ± 3.9 |
| B28 | 227.9 ± 10.5 |
| B29 | 119.1 ± 4.5 |

Example 21

Efficiency of siRNA and mRNA Incorporation into Lipid Nanoparticles

The efficiency of packaging ofthe siRNA prepared in Example 20 (which caused the degradation of mRNA encoding tyrosyl-DNA phosphodiesterase (TDP2)) into siRNA-LNP B01-B06 was determined using a Qubit microRNA Assay Kit (Life Technologies) according to the manufacturer's protocol. The efficiency of the packaging of the mRNA (encoding the fluorescence protein mKate2) into mRNA-LNP B07-B29 prepared in Example 20 was determined using a Qubit RNA HS Assay Kit (Life Technologies) according to the manufacturer's protocol. The efficiency of incorporation was determined by comparing the concentration of siRNA and mRNA freely available in the nanoparticle solution and the concentration of siRNA and mRNA released from the nanoparticles after their decomposition. LNPs were decomposed with buffer containing Triton X-100 (10 mM Tris-HCl, pH 8.0; 0.1 mM EDTA, 2% Triton X-100). High packaging efficiency of siRNA was demonstrated, ranging from 76 to 91%. The packaging efficiency of mRNA ranged from 60 to 96% (Tab. 6).

TABLE 6

Efficiency of packaging siRNA against tyrosyl-DNA phosphodiesterase 2 (TDP2) and efficiency of packaging mRNA encoding fluorescent protein mKate2 into LNPs, including standard deviations from triplicates.

| LNP | siRNA packaging (%) |
|---|---|
| B01 | 76.1 ± 4.9 |
| B02 | 91.1 ± 1.3 |
| B03 | 77.4 ± 4.6 |
| B04 | 85.0 ± 6.9 |
| B05 | 75.6 ± 2.21 |
| B06 | 89.9 ± 0.1 |
| **LNP** | **mRNA packaging (%)** |
| B07 | 88.3 ± 1.6 |
| B08 | 86.2 ± 0.9 |
| B09 | 70.4 ± 6.8 |
| B10 | 86.9 ± 0.6 |
| B11 | 64.3 ± 3.4 |
| B12 | 83.2 ± 3.2 |
| B13 | 85.5 ± 0.5 |
| B14 | 94.0 ± 0.1 |
| B15 | 96.0 ± 1.0 |
| B16 | 86.5 ± 6.5 |
| B17 | 75.0 ± 11.0 |
| B18 | 65.1 ± 0.1 |
| B19 | 67.0 ± 2.8 |
| B20 | 64.2 ± 0.2 |
| B21 | 65.0 ± 0.1 |
| B22 | 60.8 ± 3.2 |
| B23 | 63.7 ± 0.4 |
| B24 | 68.7 ± 3.3 |
| B25 | 78.8 ± 1.3 |
| B26 | 61.1 ± 1.1 |
| B27 | 75.0 ± 0.1 |
| B28 | 70.0 ± 0.1 |
| B29 | 77.0 ± 2.0 |

Example 22

Cellular Toxicity of LNPs

A human cell line derived from embryonic kidney cells expressing SV40 large T antigen (HEK293T), and human hepatocyte carcinoma cell line (HepG2) were cultured in 96-well plates ($5\times10^4$ cells in 100 1d of culture medium per well) in Dulbecco's modified medium (DMEM) supplemented with 10% foetal bovine serum (FBS) at 37° C. in 5% $CO_2$. Cells were transfected with 2 μl of LNPs B07-B12 generated in triplicates in Example 20 (the final total concentration of all lipid components in the well was 20 μM) or 10 μl of LNPs (the final total concentration of all lipid components in the well was 100 μM) and subsequently incubated for 24 hours. The cytotoxicity of LNPs was analyzed in a CellTiterGlo 2.0 cell viability assay (Promega, USA). Cell viability was normalized to non-transfected cells (control). The results are summarized in Tables 7 and 8.

For both cell lines used, none of the new LNPs exhibited significant toxicity compared to the 100 μM mixture with TT3 lipid, with which the viability of HEK293T and HepG2 cells is reduced to only 27 and 15% (Tab. 8).

TABLE 7

Cytotoxicity of LNPs expressed as cell viability (%) after the addition of 20 μM transfection mixture B07-B12 for individual cell line types.

| LNP | HEK293T | HepG2 |
|---|---|---|
| Control | 100.00 ± 4.29 | 100.00 ± 3.44 |
| B07 | 91.85 ± 4.34 | 93.49 ± 4.25 |
| B08 | 95.90 ± 6.14 | 100.85 ± 6.35 |
| B09 | 102.19 ± 5.75 | 103.10 ± 7.13 |
| B10 | 100.49 ± 3.12 | 100.93 ± 5.87 |
| B11 | 103.51 ± 5.79 | 101.74 ± 6.09 |
| B12 | 102.55 ± 5.67 | 104.55 ± 4.98 |

TABLE 8

Cytotoxicity of LNPs expressed as cell viability (%) after the addition of 100 μM transfection mixture B07-B12 for individual cell line types.

| LNP | HEK293T | HepG2 |
|---|---|---|
| Control | 100.00 ± 4.29 | 100.00 ± 3.44 |
| B07 | 99.86 ± 3.95 | 107.75 ± 7.27 |
| B08 | 103.07 ± 2.05 | 117.75 ± 3.71 |
| B09 | 106.79 ± 2.32 | 113.40 ± 5.38 |
| B10 | 70.88 ± 3.77 | 95.77 ± 3.37 |
| B11 | 108.84 ± 3.31 | 110.43 ± 1.19 |
| B12 | 27.29 ± 2.38 | 14.92 ± 4.19 |

Example 23

Transfection of siRNA Using New LNPs In Vitro

The siRNA-LNP particles containing small interfering RNA (siRNA, catalog number 4392420, Ambion) that causes degradation of mRNA encoding tyrosyl-DNA phosphodiesterase 2 (TDP2) were prepared according to Example 20. Lipofectamine RNAiMax (Invitrogen) was used as a control transfection reagent specifically for siRNA transfection. The human cell line HEK293T and the cell line derived from human multiple myeloma, which is very difficult to transfect with available transfection reagents, were used for siRNA-LNP knock-down (Brito J. L. R., Brown N., Morgan G. J. (2010) The transfection of siRNAs in Multiple Myeloma Cell Lines. In. Min WP., Ichim T. (eds) RNA Interference. Methods in Molecular Biology (Methods and Protocols), vol 623. Humana Press). Cells were cultured in 96-well plates ($5\times10^4$ cells in 100 1d culture medium per well) in DMEM medium supplemented with 10% FBS at 37° C. in 5% $CO_2$. Cells were transfected with 2 1d siRNA-LNP (with a final total concentration of all lipid components of 20 μM and a final siRNA concentration of 16 nM) and subsequently incubated for 24 hours. Transfections were performed in biological triplicates. RNA was isolated using an RNAeasy Plus Micro Kit (Qiagen). cDNA was prepared using TATAA GrandScript cDNA Supermix (TATAAbiocenter) according to the manufacturer's recommendations. Quantitative RT-PCR was performed using a LightCycler 480 (Roche Life Science). The primers for amplifying mRNA encoding TDP2 were as follows: 5'-CGAGAGGAGGGTCTCAAAGAG-3' (SEQ ID NO. 3)

and 5'-ATTTCGGGAAGGCTGCTGTC-3' (SEQ ID NO. 4). mRNA encoding GAPDH was used to normalize the data (Primers: 5'-AATCCCATCACCATCTTCCA-3' (SEQ ID NO. 5) and 5'-TGGACTCCACGACGTACTCA-3' (SEQ ID NO. 6)).

In all these cases, the new siRNA-LNPs significantly reduced the level of TDP2 mRNA in the cells compared to the commercial transfection reagent RNAiMax. In the HEK293T cell line, the new LNPs B02-B05 have almost 3-fold higher efficiency than RNAiMax. In the OPM-2 myeloma line, B03 reduces mRNA expression 13-fold better than a commercial siRNA transfection reagent (Tab. 9).

TABLE 9

Reduction of endogenously expressed TDP2 mRNA in cells by new siRNA-LNPs (B01-B06) compared to commercial transfection reagent RNAiMax in the HEK293T and OPM-2 cell lines.

| LNP | HEK293T | p | OPM-2 | p |
|---|---|---|---|---|
| Control | 1.00 ± 0.10 | | 1.00 ± 0.10 | |
| B01 | 0.24 ± 0.17 | | 0.52 ± 0.05 | |
| B02 | 0.04 ± 0.02 | c | 0.11 ± 0.01 | a |
| B03 | 0.05 ± 0.03 | c | 0.04 ± 0.01 | a |
| B04 | 0.06 ± 0.02 | c | 0.08 ± 0.02 | a |
| B05 | 0.05 ± 0.01 | c | 0.05 ± 0.01 | a |
| B06 | 0.05 ± 0.01 | c | 0.07 ± 0.02 | a |
| RNAiMax | 0.15 ± 0.06 | — | 0.52 ± 0.02 | — |

Statistics were evaluated by Student's unpaired t-test.

P values are based on the Lipofectamine RNAiMax control transfection mixture; p values <0.001 are marked with the letter "a", p values <0.05 are marked with the letter "c".

Example 24

Transfection of mRNA Using New LNPs In Vitro

A human cell line derived from embryonic kidney cells expressing the large SV40 T antigen (HEK293T), liver carcinoma cells (HepG2) and a human osteosarcoma-derived cell line (U2OS) were cultured in 96-well plates ($5\times10^4$ cells in 100 1d culture medium per well) in Dulbecco's modified medium (DMEM) supplemented with 10% fetal bovine serum (FBS) at 37° C. in 5% $CO_2$ Cells were transfected with 2 1d of the mRNA-LNP B07 to B12, prepared in Example 20 and subsequently incubated for 24 hours. The final total concentration of the lipid components in the well was 20 μM and the amount of mRNA that encodes the fluorescent protein mKate2 was 100 ng. Lipofectamine® 2000 was used as a control transfection reagent. Transfections were performed in three biological replicates, with each biological replicate having three technical replicates. The Cy5 and mKate2 fluorescence was detected using the BD LSR Fortessa cytometer, and the percentage of cells positive for Cy5 fluorescence, indicating LNP entry into cells (Tab. 10), percentage of cells expressing the fluorescent protein mKate2 and the fluorescence intensity of the mKate2 (Tab. 11) were calculated. For fluorescence intensity, the data were normalized to the commercial transfection reagent Lipofectamine® 2000. According to Cy5 fluorescence, it is evident that all LNPs enter cells with an efficiency exceeding 90% (Tab. 10). Furthermore, the new LNPs B11 produce 2.13-fold more fluorescent mKate2 protein from transfected mRNA than cells transfected with Lipofectamine® 2000 transfection control (Tab. 11).

TABLE 10

Transfection efficiency of new mRNA-LNPs (B07-B12) expressed as a percentage of cells positive for Cy5 for cell lines HEK293T and HepG2. The transfection mixtures contain a lipid labeled with the fluorescent dye Cy5, which makes it possible to observe the entry of LNPs into the cells.

| LNP | HEK293T | HepG2 |
|---|---|---|
| B07 | 99.28 ± 0.10 | 98.59 ± 0.15 |
| B08 | 99.19 ± 0.09 | 94.73 ± 0.88 |
| B09 | 97.83 ± 0.63 | 90.52 ± 2.39 |
| B10 | 97.79 ± 0.36 | 92.93 ± 0.77 |
| B11 | 98.59 ± 0.47 | 96.49 ± 1.70 |
| B12 | 97.94 ± 0.94 | 95.19 ± 0.98 |

TABLE 11

Transfection efficiency of new mRNA-LNPs expressed as a percentage of cells expressing fluorescent mKate2 protein and fluorescence inensity of mKate2 from mRNA transfected with particles for U2OS cell line.

| LNP | % of cells Expressing mKate2 | p | Fluorescence of mKate2 | p |
|---|---|---|---|---|
| B07 | 28.76 ± 1.51 | | 0.10 ± 0.00 | |
| B08 | 88.62 ± 0.60 | a | 1.08 ± 0.07 | |
| B09 | 88.38 ± 1.00 | a | 1.79 ± 0.23 | a |
| B10 | 84.46 ± 1.06 | a | 0.69 ± 0.08 | |
| B11 | 92.32 ± 2.18 | a | 2.13 ± 0.19 | a |
| B12 | 90.63 ± 0.92 | a | 1.86 ± 0.31 | a |
| Lip2000 | 47.67 ± 1.25 | — | 1.00 ± 0.05 | — |

Statistics were evaluated by Student's unpaired t-test.

The p values are related to the control transfection mixture Lipofectamine2000; p values < 0.001 are indicated with the letter "a".

Example 25

Transfection of mRNA Using New LNPs In Vitro

A human cell line derived from embryonic kidney cells expressing the large SV40T antigen (HEK293T) was cultured in 96-well plates ($2.5\times10^4$ cells in 100 μl culture medium per well) in Dulbecco's modified medium (DMEM) supplemented with 10% fetal bovine serum (FBS) at 37° C. in 5% $CO_2$. Cells were transfected with mRNA-LNPs B08a, B11a, B13 to B18, B20 to B25 and B29 prepared in Example 20 and then incubated for 24 hours. The final total concentration of all lipid components in the well was 20 μM and the amount of mRNA encoding the fluorescent protein mKate2 was 100 ng. B29 LNPs containing benchmark D-Lin-MC3-DMA lipid were used as a control. Transfections were performed in triplicate. The percentage of cells expressing the fluorescent protein mKate2 and the fluorescence intensity of the mKate2 (Tab. 12) were analyzed in a BD LSR Fortessa cytometer at a a wavelength of 561-610/20 nm. For fluorescence intensity, data were normalized to the benchmark D-Lin-MC3-DMA containing LNPs (B29). It is evident that all new LNPs transfected the HEK293T cells more efficiently, as documented by significantly higher % of transfected cells as well as by significantly increased fluorescence intensity compared to the benchmark D-Lin-MC3-DMA LNPs. In particular, the new LNPs B22 produce 13.66-fold more fluorescent mKate2 protein from transfected mRNA than cells transfected with B29 LNPs containing the benchmark D-Lin-MC3-DMA lipid (Tab. 12).

TABLE 12

Transfection efficiency of new mRNA-LNPs for HEK293T cell line shown as a percentage of cells expressing fluorescent mKate2 protein from mRNA delivered by LNPs.

| LNP | % of cells transfected | p (D-Lin-MC3-DMA) | Normalized fluorescence of mKate2 | p (D-Lin-MC3-DMA) |
|---|---|---|---|---|
| B08a | 86.2 ± 2.1 | a | 3.72 ± 0.11 | a |
| B11a | 76.0 ± 3.8 | b | 3.10 ± 0.16 | b |
| B13 | 94.0 ± 0.7 | a | 5.27 ± 0.25 | a |
| B14 | 77.1 ± 5.3 | b | 1.70 ± 0.12 | b |
| B15 | 83.5 ± 3.8 | b | 1.98 ± 0.31 | c |
| B16 | 69.5 ± 1.3 | b | 1.37 ± 0.05 | b |
| B17 | 85.4 ± 3.2 | b | 3.79 ± 0.67 | c |
| B18 | 82.8 ± 1.5 | a | 3.99 ± 0.39 | b |
| B20 | 86.6 ± 9.1 | c | 7.78 ± 1.63 | c |
| B21 | 56.5 ± 2.3 | c | 2.41 ± 0.21 | b |
| B22 | 93.3 ± 1.5 | a | 13.66 ± 1.46 | a |
| B23 | 89.7 ± 5.7 | b | 7.89 ± 1.35 | b |
| B24 | 72.4 ± 1.3 | b | 1.88 ± 0.09 | a |
| B25 | 62.2 ± 4.2 | c | 1.58 ± 0.13 | c |
| B29 | 29.9 ± 4.2 | — | 1.00 ± 0.02 | — |

Statistics were evaluated by Student's unpaired t-test.
The p values are related to the control D-Lin-MC3-DMA (B29) LNPs; p values <0.0001 are indicated with the letter "a", p <0.001 as "b", p <0.01 as "c", respectively.

Example 26

Transfection Efficacy of New mRNA-LNPs Monitored by Cre-Based Recombination

Mouse embryonic fibroblast cells (MEFs), derived from the mouse model with a global dual Cre reporter (Mazumdar, M. D.: *Genesis* 2007, 45:593-605), were seeded (2.5× $10^4$ cells in 100 1d culture medium per well) on a 96-well plate and cultured in DMEM supplemented with 10% FBS at 37° C. in 5% CO, for 24 hours. Messenger RNA (mRNA) encoding Cre recombinase was prepared in vitro analogously to Example 20 from a linearized plasmid and packaged into LNP as follows: A 300 1d sample of transfection reagents A13 to A25, A02 and A27 and the control transfection reagent A29 including the benchmark D-Lin-MC3-DMA lipid, and 120 μg of mRNA in 300 μl of 10 mM citrate buffer (pH 3.0) were assembled into LNP using a microfluidic device analogously to Example 20. The resulting mRNA-LNPs were immediately diluted in 600 μl PBS; the corresponding nanoparticles labeled B31 to B43 (formed from transfection reagent A13 to A25), nanoparticles B30 (formed from transfection reagent A02), nanoparticles B44 (formed from transfection reagent A27) and analogously, the benchmark nanoparticles labeled B45 were thus formed from transfection reagent A29.

Cells were transfected with the respective mRNA-LNPs (the final total concentration of all lipid components in the well was 20 μM) carrying 100 ng of mRNA encoding the Cre recombinase and subsequently incubated for 48 hours. B45 LNPs containing benchmark D-Lin-MC3-DMA lipid were used as a control. Transfections were performed in quadruplicates. The percentage of cells expressing GFP was analyzed using a BD LSR Fortessa cytometer (at a wavelength of 488-530/30 nm). It is again evident that all new LNPs transfected the mT/mG cells more efficiently, as documented by a significantly higher percentage of cells expressing GFP compared to cells transfected with the benchmark D-Lin-MC3-DMA LNPs (B45). Interestingly, the percentage of cells expressing GFP was always higher than 95% for all new LNPs tested (except B44), whereas LNPs containing the benchmark D-Lin-MC3-DMA lipid showed only 21% of recombined cells (Tab. 13).

TABLE 13

Comparison of the efficacy of new Cre mRNA-LNPs to convert td Tomato into GFP in MEFs derived from the mT/mG reporter mouse embryos.

| LNP | % cells expressing GFP | p (D-Lin-MC3-DMA) |
|---|---|---|
| B30 | 99.05 ± 0.10 | a |
| B31 | 99.83 ± 0.07 | a |
| B32 | 99.60 ± 0.01 | a |
| B33 | 95.50 ± 0.04 | a |
| B34 | 99.75 ± 0.13 | a |
| B35 | 99.13 ± 0.32 | a |
| B36 | 99.00 ± 0.17 | a |
| B37 | 98.85 ± 0.45 | a |
| B38 | 99.48 ± 0.10 | a |
| B39 | 95.50 ± 1.25 | a |
| B40 | 99.13 ± 0.22 | a |
| B41 | 98.00 ± 0.43 | a |
| B42 | 99.80 ± 0.06 | a |
| B43 | 99.73 ± 0.04 | a |
| B44 | 69.05 ± 2.00 | a |
| B45 | 21.25 ± 2.35 | — |
| untreated | 0.325 ± 0.248 | a |

Statistics were evaluated using Student's unpaired t-test.
The p values are related to the control D-Lin-MC3-DMA (B45) LNPs; p values <0.0001 are indicated with the letter "a".

Example 27

Biodistribution of New mRNA-LNPs In Vivo

Figure 10:
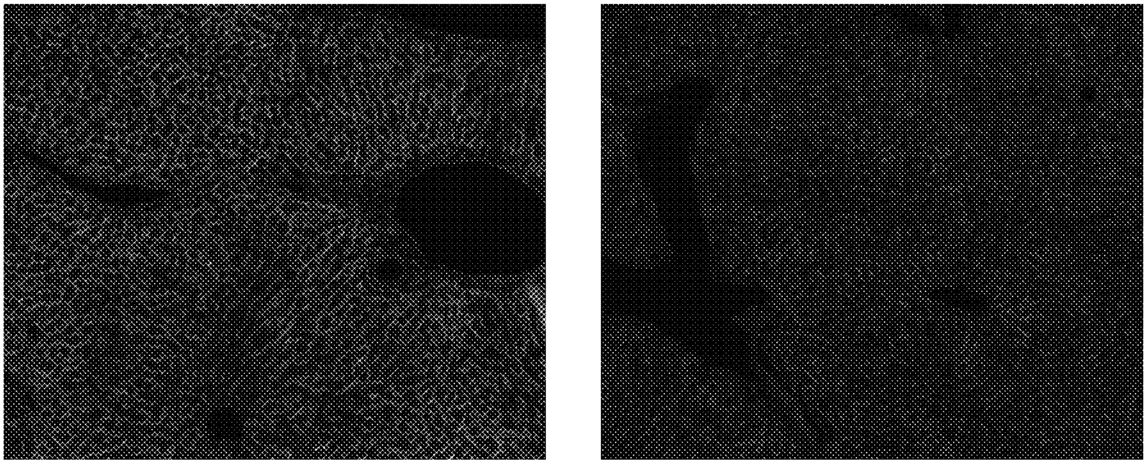
FIG. 10. Functional delivery of mRNA-LNP (B40) in murine liver in comparison to benchmark LNP (B45) analyzed by histology.

The Messenger RNA (mRNA) encoding Cre recombinase was prepared in vitro analogously to Example 20 from a linearized plasmid and packaged into LNP as follows: A 300 μl sample of transfection reagent A22 and the control transfection reagent A29 that includes the benchmark lipid D-Lin-MC3-DMA and 120 g of mRNA in 300 1d of 10 mM citrate buffer (pH 3.0) were assembled into LNP using a microfluidic device analogously to Example 20. The resulting mRNA-LNPs were immediately diluted in 600 μl PBS; the corresponding B40 labeled nanoparticles were formed from the transfection reagent A22. Analogously, the benchmark nanoparticles labeled B45 were thus formed from the transfection reagent A29. The mRNA-LNPs were dialyzed in PBS and filtered. Endotoxin levels were <2 EU/ml. The mRNA-LNPs (B40 and B45) were administered intravenously at a concentration of 2.0 mg mRNA/kg in each case to 4 mice with a global dual Cre reporter (Mazumdar, M. D.: *Genesis* 2007, 45:593-605) (breeding BIOCEV, Vestec) enabling the analysis of successful recombination. In cells to which mRNA-LNPs carrying Cre recombinase mRNA were successfully delivered, chromosomal recombination and subsequent excision of the membrane red protein gene (the so-called red tomato) and "turning on" the transcription of membrane green protein (GFP) gene occurred. Mice, including non-particulate control mice, were sacrificed 5 days after particulate application, and specific organs (liver, heart, kidney, lungs, and spleen) were subjected to histological analysis according to a standardized protocol. Analysis of histological images revealed a complete distribution of the B40 nanoparticles in the liver, leading to a 50-80% conversion of cells expressing the red membrane protein to cells expressing the green membrane protein 5 days after application. In the case of the D-Lin-MC3-DMA lipid containing LNPs B45, the conversion was about 20% (FIG. 10).

Figure 11:
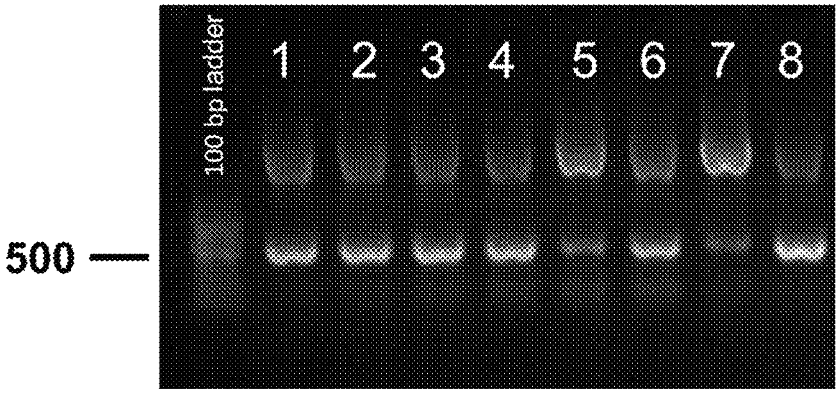
FIG. 11. Functional delivery of mRNA-LNP (B40) in murine liver in comparison to benchmark LNP (B45) analyzed by PCR amplification ofthe genomic DNA. Lanes marked from 1 to 4 relate to B40. Lanes marked from 5 to 8 relate to B45.

Histological analysis was further complemented by the evaluation of tdTomato/GFP conversion in the liver of the mT/mG mice by genomic DNA (gDNA) PCR analysis. Briefly, 50 ng of the gDNA template isolated from the respective liver samples was used in the PCR reaction with subsequent primers: (5'-AACGTGCTGGTTATTGTGCTG-'3 (SEQ ID NO. 7); 5'-AAGTCGTGCTGCTTCATGTG-'3 (SEQ ID NO. 8)). In FIG. 11, electrophoretic analysis of the resulting gDNA PCR amplification of the liver samples shows the PCR product of 530 bp in the case of the active Cre recombination at the tdTomato/tGFP locus, while the PCR product of 2943 bp (upper band) in the case no Cre recombination occurred. The designated B40 mRNA-LNPs showed complete Cre recombination in all 4 mice tested, while in the case of the benchark LNPs (B45) the recombination was complete only in 50% of the tested mice.

Example 28

Efficacy of New mRNA-LNPs In Vivo

Messenger RNA (mRNA) encoding hEPO (human erythropoetin) was prepared in vitro analogously to Example 20 from a linearized plasmid and packaged in LNP as follows: A 300 1d sample of transfection reagent A23 or the control transfection reagent A29 that includes the benchmark lipid D-Lin-MC3-DMA and 120 μg of mRNA in 300 μl of 10 mM citrate buffer (pH 3.0) were assembled into LNP using a microfluidic device analogously to Example 20. The resulting mRNA-LNPs were immediately diluted in 600 μl PBS; the corresponding B46 labeled nanoparticles were thus formed from the transfection reagent A23. Analogously, the benchmark nanoparticles labeled B47 were thus formed from the transfection reagent A29. The mRNA-LNPs were dialyzed in PBS and filtered. Endotoxin levels were <0.3 EU/ml. The mRNA-LNPs (B46 and B47) were administered intravenously at a concentration of 0.5 mg mRNA/kg in each case to 3 C57Bl/6 mice (BIOCEV, Vestec), wherein three control C57Bl/6 mice were administered with PBS. Six hours after administration, blood was collected from mice via the tail vein and allowed to clot at room temperature in serum separator tubes. The tubes were then centrifuged at 7000 rpm for 7 min and the sera samples were aliquoted and stored at −80° C. until analysis. hEPO concentrations were determined using an hEPO ELISA assay (Catalog #DEP00; R&D Systems, Minneapolis, MN, USA) according to the manufacturer's instructions. Hematology profiles were determined using a standardized protocol. Nanoparticles designated as B46 showed higher, yet statistically not significant, production of the human EPO protein 6 hours after administration compared to control B47 LNPs. Importantly, LNPs containing new lipidoid (B46) did not alter hematology profile as opposed to control B47 LNPs. The blood test after the new LNP administration remained comparable to PBS control (Tab. 14).

TABLE 14

Comparison of the in vivo efficacy of new human EPO mRNA-LNPs in protein production six hours after administration.

| LNP | hEPO [mIU/ml] | WBS# [*$10^9$/L] | Neu# [*$10^9$/L] | Lym# [*$10^9$/L] |
|---|---|---|---|---|
| B46 | 750 ± 514 | 4.91 ± 0.57 | 0.90 ± 0.19 | 3.58 ± 0.73 |
| B47 | 465 ± 154 | 10.06 ± 2.59 | 4.89 ± 2.66 | 4.23 ± 0.43 |
| PBS | | 4.40 ± 1.12 | 1.02 ± 0.84 | 3.09 ± 0.33 |

Example 29

Efficacy of New siRNA-LNPs In Vivo

Transfection reagents A02, A14, A16, A17, A22, A23 and A29 from Example 19 was used to form siRNA-LNPs designated as B48 to B54, respectively, with siRNA targeting mouse apolipoprotein B (ApoB) gene, a hepatocyte-expressed gene involved in cholesterol transport (catalogue number 238055 Apob mouse siPOOL-40 kit, siTOOLs Biotech GmbH) and alternatively siRNA-LNPs (B55 to B60) with control non-targeted siRNA-LNPs (enclosed in 238055 Apob mouse siPOOL-40 kit, siTOOLs Biotech GmbH), assembled as described in Example 20. The hydrodynamic diameter measured by dynamic light scattering ranged from 103 nm to 154 nm and the efficiency of packaging of the siRNA pool ranged from 59% to 99%. The siRNA-LNPs were dialyzed to PBS. Endotoxin levels were <2 EU/ml. Mice were fasted for 4 hours before plasma collection by retroorbital bleed. The siRNA-LNPs targeting ApoB were administered intravenously to 3 C57Bl/6 mice (BIOCEV, Czech Center of Phenogenomics, Vestec) at a concentration of 16 μg of siRNA, wherein the control 3 mice were administered with 16 μg of non-targeting siRNA-LNPs and another 3 mice were administered PBS control. All mice were sacrificed 2 days after LNP application. Plasma levels of cholesterol, triglycerides and LDL-C were measured by using automated systems at the Czech Center of Phenogenomics according to standardized protocol.

Clinical biochemistry of plasma markers such as total cholesterol, triglycerides and LDL-C, affected by ApoB knock down, were significantly decreased compared to control animals, demonstrating thus the efficient delivery of ApoB siRNA by novel LNPs into the liver (Tab. 15).

TABLE 15

Clinical biochemistry of plasma markers indicating efficient ApoB knockdown in the liver.

| LNP | Total cholesterol, mmol/L | p1 | p2 | Triglycerides, mmol/L | p1 | p2 | LDL-C, mmol/L | p1 | p2 |
|---|---|---|---|---|---|---|---|---|---|
| PBS control | 2.27 ± 0.20 | | | 0.60 ± 0.12 | | | 0.45 ± 0.05 | | |
| B48 | 0.82 ± 0.02 | a | a | 0.71 ± 0.07 | | | 0.21 ± 0.02 | b | |
| B49 | 0.52 ± 0.06 | a | a | 0.19 ± 0.01 | b | b | 0.15 ± 0.03 | b | d |
| B50 | 0.85 ± 0.45 | c | d | 0.42 ± 0.13 | | c | 0.33 ± 0.20 | | d |
| B51 | 0.51 ± 0.10 | a | b | 0.25 ± 0.01 | c | a | 0.22 ± 0.05 | c | d |
| B52 | 0.50 ± 0.21 | a | b | 0.27 ± 0.01 | c | a | 0.19 ± 0.08 | c | d |
| B53 | 0.62 ± 0.15 | a | b | 0.3 ± 0.01 | c | a | 0.29 ± 0.02 | c | |
| B55 | 2.36 ± 0.61 | | n.e. | 0.52 ± 0.01 | | n.e. | 0.64 ± 0.14 | | n.e. |
| B56 | 2.47 ± 0.20 | | n.e. | 0.65 ± 0.10 | | n.e. | 0.63 ± 0.10 | d | n.e. |
| B57 | 2.41 ± 0.50 | | n.e. | 0.80 ± 0.20 | | n.e. | 0.8 ± 0.22 | d | n.e. |
| B58 | 2.46 ± 0.76 | | n.e. | 0.92 ± 0.14 | d | n.e. | 0.78 ± 0.24 | d | n.e. |
| B59 | 2.50 ± 0.77 | | n.e. | 0.79 ± 0.08 | | n.e. | 0.77 ± 0.32 | | n.e. |
| B60 | 2.56 ± 0.76 | | n.e. | 1.00 + 0.07 | c | n.e. | 0.73 ± 0.19 | d | n.e. |

Statistics were evaluated by Student's unpaired t-test.
The p1 values are always relative to the control mice injected with PBS;
the p2 values are always relative to the mice injected with respective (B55 to B60) LNPs with control non-targeted siRNA;
values of $p < 0.0001$ are marked as "a", $p < 0.001$ are marked as "b",
$p < 0.01$ are marked as "c", and
$p < 0.05$ are marked as "d".
Those cases that were not evaluated are marked with "n.e.".

The toxicity of new siRNA-LNPs was further evaluated by analyzing the clinical biochemistry of plasma markers that indicate organ failure and the hematology profile compared to saline-injected controls (PBS) and control LNPs (B54) containing the lipid D-Lin-MC3-DMA. In particular, new siRNA-LNPs designated as B49 showed a better toxicology profile when compared to the control B54 LNPs (Tab. 16).

TABLE 16

Clinical biochemistry of plasma markers and hematology profile of new siRNA-LNPs designated as B49 compared to control siRNA-LNPs containing the benchmark lipid D-Lin-MC3-DMA (B54).

| LNP | B49 | p1 | p2 | B54 | p1 | PBS |
|---|---|---|---|---|---|---|
| Total bilirubin, μmol/L | 2.8 ± 1.06 | | | 2.5 ± 0.34 | | 2.14 ± 0.43 |
| AST, U/L | 66 ± 12.06 | | | 150 ± 76.14 | | 74.6 ± 7.78 |
| ALT, U/L | 25 ± 3.79 | | | 75 ± 47.52 | | 23.8 ± 1.6 |
| HBDH, U/L | 81.03 ± 18.8 | | d | 148.7 ± 15.2 | c | 63.2 ± 8.24 |
| LDH, U/L | 310.1 ± 73.82 | | | 567 ± 61.8 | c | 231.2 ± 30.45 |
| WBC, $*10^9$/L | 3.17 ± 0.91 | | | 6.58 ± 1.43 | | 4.35 ± 0.44 |
| Neutrophils, % | 34 ± 7 | d | | 51 ± 11 | c | 18 ± 2 |
| Neutrophils, $*10^9$/L | 1.18 ± 0.55 | | | 3.65 ± 1.37 | d | 0.79 ± 0.09 |
| Lymphocytes, % | 64 ± 6 | d | | 45 ± 1 | c | 77 ± 2 |
| Lymphocytes, $*10^9$/L | 1.93 ± 0.41 | | | 2.69 ± 0.36 | | 3.35 ± 0.38 |

Statistics were evaluated by Student's unpaired t-test.
The p1 values are always relative to the control mice injected with PBS;
the p2 values are always relative to the mice injected with control B54 LNPs;
values of $p < 0.01$ are marked as "c" and
$p < 0.05$ are marked as "d".

INDUSTRIAL APPLICABILITY

The transfection particles containing lipidoids of the present invention are useful for a variety of biological applications in basic research, particularly cell culture or animal transfections to deliver active NA and subsequently silence or activate the chromosomal gene or genes, edit the genome or transcriptome, or allow the expression of protein encoded in the NA inserted using a transfection particle.

In veterinary and human medicine, the transfection particles containing lipidoids of general formula I can preferably be used for therapeutic or prophylactic purposes. Therapeutic NA-containing particles can be administered to an animal or human to silence or activate chromosomal gene (s), silence or activate immunogens, inhibit or activate signaling pathways, edit the genome or transcriptome, or allow expression of the NA-encoded protein(s).

The lipidoids of the formula I or transfection agents or transfection particles can also be used as medicaments, in particular for gene therapy, and are suitable for use in the treatment of malignancies and/or genetic disorders. They can also be formulated for cosmetic or biotechnological use.

The invention claimed is:

1. Lipidoids of general formula (I)

(I)

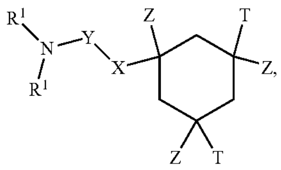

wherein

X is selected from the group comprising —C(═O)NH—, —C(═O)O—, —C(═S)O—, —C(═O)S—, —C(═S)S—, —C(═O)NHNH—, $—CH_2—$, —O—, —OC(═O)—, —S—, —SC(═O)—, —NH—, —NHNH—, —NHC(═O)—, —NHNHC(═O)—, —C≡C—, —CH═CH—, a five-membered heterocycle containing at least 2 nitrogen atoms, $—CH_2C(═O)NH—$, $—CH_2C(═O)O—$, $—CH_2C(═S)O—$, $—CH_2C(═S)S—$, $—CH_2C(═O)NHNH—$, —N═CH—, —CH═N—, —NH—N═CH—, and —CH═N—NH—;

Y is selected from the group consisting of $C_2$-$C_{10}$ alkylene chains, wherein the alkylene chain, one or more $—CH_2—$ groups may optionally be replaced with one or more O and/or S atoms;

$R^1$ are the same or different from each other, each $R^1$ being independently selected from the group consisting of $C_1$-$C_{46}$ alkyl, $C_2$-$C_{46}$ alkenyl, $C_2$-$C_{46}$ alkynyl, wherein the alkyl, alkenyl or alkynyl may be linear or branched, and wherein in the alkyl, alkenyl or alkynyl, one or more $—CH_2—$ groups may be replaced with CH(OH), —OC(═O)—, —C(═O)O—, —S—S—, —C(═O)NH—, —NHC(═O)—, —O—, and —S—;

wherein if $R^1$ is $C_1$-$C_4$ alkyl, then one hydrogen from the terminal $—CH_3$ group may be substituted with Z;

with the proviso that at least one $R^1$ contains at least 8 carbon atoms;

Z are the same or different from each other, each Z being independently selected from the group comprising hydrogen, —OH, $—CH_3$, $—CH_2OH$, $—NH_2$, $—C(═O)NH_2$, $—CONH(CH_2)_2OH$, $—CON[(CH_2)_2OH]_2$, $—CONHCH(CH_2OH)_2$, $—CONHCH_2CH(—OH)CH_2OH$, $—CONH(CH_2)_2C(═O)NH_2$, $—CON[CH_2C(═O)NH_2]_2$, $—CONHCH[C(═O)NH_2]_2$, $—CONH(CH_2)_2NHC(═O)NH_2$, $—CONH(CH_2)_3—N^+(CH_3)_2—(CH_2)_2—SO_3^-$, $—CONH(CH_2)_3—N^+(CH_3)_2—(CH_2)_3—SO_3^-$, $—CONH(CH_2)_3—N^+(CH_3)_2—(CH_2)_2—COO^-$, $—COO(CH_2)_2—O—P(═O)(O^-)—O(CH_2)_2—N^+(CH_3)_3$, $—N^+(CH_3)_2—(CH_2)_3—SO_3^-$, $—N^+(CH_3)_2—(CH_2)_2—COO^-$,

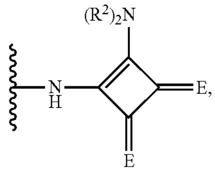

and

-continued

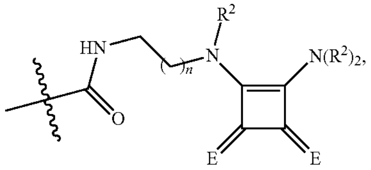

wherein $R^2$ is independently selected from hydrogen and $—CH_3$;

E is independently selected from O and S atoms;

n is an integer within the range of from 1 to 5;

and T are the same or different from each other, each T being independently selected from the group comprising —X—Y—$N(R^1)_2$, —C(═O)O($C_1$-$C_3$ alkyl), $—C(═O)OCH_2CH_2OH$, $—C(═O)NH_2$,

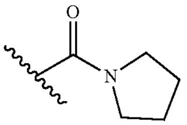

$—C(═O)OH$, $—CONH(CH_2)_2OH$, $—CON[(CH_2)_2OH]_2$, $—CONHCH(CH_2OH)_2$, $—CONHCH_2CH(—OH)CH_2OH$, $—CONH(CH_2)_2C(═O)NH_2$, $—CON[CH_2C(═O)NH_2]_2$, $—CONHCH[C(═O)NH_2]_2$, $—CONH(CH_2)_2NHC(═O)NH_2$, $—CONH(CH_2)_3—N^+(CH_3)_2—(CH_2)_2—SO_3^-$, $—CONH(CH_2)_3—N^+(CH_3)_2—(CH_2)_3—SO_3^-$, $—CONH(CH_2)_3—N^+(CH_3)_2—(CH_2)_2—COO^-$, $—COO(CH_2)_2—O—P(═O)(O—)—O(CH_2)_2—N^+(CH_3)_3$,

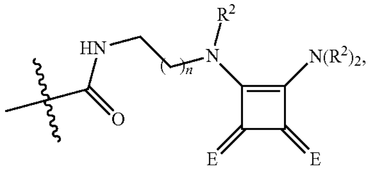

—OH, —O($C_1$-$C_3$ alkyl), $—NH_2$, $—NHC(═O)CH_3$, $—NHS(═O)_2CH_3$, $—NHC(═O)N(CH_3)_2$, $—NHC(═O)NH(CH_3)$, $—NHC(═S)N(CH_3)_2$, $—NHC(═S)NH(CH_3)$, $—NHC(═N—CN)NH_2$, $—NHC(═N—CN)NH(CH_3)$, $—NHC(═N—CN)N(CH_3)_2$, $—NHC[═N—S(═O)_2NH_2]NH_2$, $—N^+(CH_3)_2—(CH_2)_3—SO_3^-$, $—N^+(CH_3)_2—(CH_2)_2—COO^-$, and

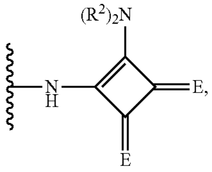

wherein $R^2$, E and n are as defined above;

and/or if Z is —OH or $—CH_2OH$, and T is —C(═O)OH, then Z together with T and three carbon atoms between them may form a cyclic lactone containing 4 to 5 carbon atoms;

and pharmaceutically acceptable salts, addition salts and solvates thereof.

2. The lipidoid according to claim 1, wherein X is selected from the group consisting of —C(═O)NH—, —C(═O)O—, —C(═O)NHNH—, —OC(═O)—, —O—, —NHC(═O)—, —NHNHC(═O)—, and a five-membered heterocycle containing at least 2 nitrogen atoms.

3. The lipidoid according to claim 1, wherein $R^1$ are independently selected from the group consisting of $C_1$-$C_{46}$ alkyl, and $C_2$-$C_{46}$ alkenyl, wherein in the said alkyl or alkenyl, one or more —$CH_2$— groups may optionally be replaced with —C(═O)O—.

4. The compound according to claim 1, wherein all $R^1$ in the compound are the same.

5. The compound according to claim 1, wherein Z is selected from the group consisting of hydrogen, —OH, —$CH_3$, —$CH_2OH$, —$NH_2$, —C(═O)$NH_2$, —CONH$(CH_2)_2$OH, —CON$[(CH_2)_2OH]_2$, —CONHCH$(CH_2OH)_2$, —CONH$CH_2$CH(—OH)$CH_2$OH, —CONH$(CH_2)_2$C(═O)$NH_2$, —CON[$CH_2$C(═O)$NH_2]_2$, —CONHCH[C(═O)$NH_2]_2$, —CONH$(CH_2)_2$NHC(═O)$NH_2$, —$N^+(CH_3)_2$—$(CH_2)_3$—$SO_3^-$, —$N^+(CH_3)_2$—$(CH_2)_2$—$COO^-$,

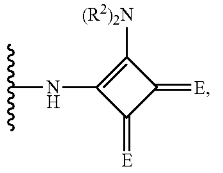

and

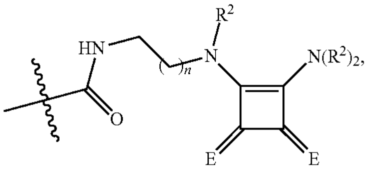

wherein $R^2$, E and n are as defined in claim 1.

6. The lipidoid according to claim 1, wherein T is selected from the group consisting of —X—Y—N$(R^1)_2$, —C(═O)O($C_1$-$C_3$ alkyl), —C(═O)O$CH_2CH_2$OH, —C(═O)$NH_2$,

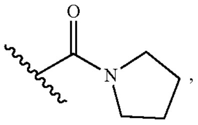 [SMILES: *C(=O)N1CCCC1]

—C(═O)OH, —CONH$(CH_2)_2$OH, —CON$[(CH_2)_2OH]_2$, —CONHCH$(CH_2OH)_2$, —CONH$CH_2$CH(—OH)$CH_2$OH, —CONH$(CH_2)_2$C(═O)$NH_2$, —CON[$CH_2$C(═O)$NH_2]_2$, —CONHCH[C(═O)$NH_2]_2$, —CONH$(CH_2)_2$NHC(═O)$NH_2$, —CONH$(CH_2)_3$—$N^+(CH_3)_2$—$(CH_2)_2$—$SO_3^-$, —CONH$(CH_2)_3$—$N^+(CH_3)_2$—$(CH_2)_3$—$SO_3^-$, —CONH$(CH_2)_3$—$N^+(CH_3)_2$—$(CH_2)_2$—$COO^-$, —COO$(CH_2)_2$—O—P(═O)(O—)—O$(CH_2)_2$—$N^+(CH_3)_3$, and

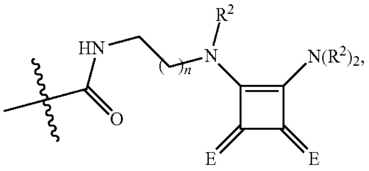

wherein $R^2$, E and n are as defined in claim 1.

7. The compound according to claim 1, wherein at least one T is —X—Y—N$(R^1)_2$.

8. The compound according to claim 1, wherein Z is selected from the group consisting of hydrogen, —OH, —$CH_3$, and —$CH_2$OH;

and T is selected from the group consisting of —X—Y—N$(R^1)_2$, —C(═O)O($C_1$-$C_3$ alkyl),

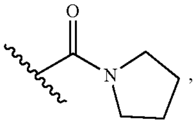 [SMILES: *C(=O)N1CCCC1]

and —C(═O)OH;

and/or if Z is —OH or —$CH_2$OH, and T is —C(═O)OH, then Z together with T and three carbon atoms between them may form a cyclic lactone containing 4 to 5 carbon atoms.

9. The lipidoid according to claim 1, wherein:

X is —C(═O)NH— or —NHC(═O)—;

Y is selected from —$(CH_2)_3$—, —$(CH_2)_4$—, —$(CH_2)_5$—, and —$(CH_2)_6$—;

$R^1$ is selected from the group comprising linear or branched $C_{10}$-$C_{15}$alkyl; and linear or branched $C_{12}$-$C_{18}$alkenyl;

wherein in the alkyl or alkenyl, one or more —$CH_2$— groups may be replaced with —C(═O)O—;

T is selected from —X—Y—N$(R^1)_2$, —C(═O)O$CH_3$,

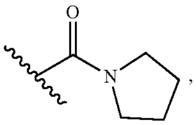 [SMILES: *C(=O)N1CCCC1]

and —C(═O)OH;

Z is selected from H, —$CH_3$, and —$CH_2$OH.

10. The compound according to claim 1, wherein the compund of general formula (I) contains at least two $R^1$ substituents, each of them containing at least 8 carbon atoms.

11. A transfection agent comprising at least one compound of general formula (I) according to claim 1, and at least one helper lipid; wherein the helper lipid is selected from the group comprising cholesterol, β-sitosterol, stigmastanol, campesterol, fucosterol, avenasterol, fecosterol, brassicasterol, ergosterol, 9,11-dehydroergosterol, 1,2-dioleoyl-sn-glycero-3-phosphoethanolamine (DOPE), 1,2-dioleoyl-sn-glycero-3-phosphocholine (DOPC), 1,2-distearoyl-sn-glycero-3-phosphocholine (DSPC), 1,2-dipalmitoyl-sn-glycero-3-phosphocholine (DPPC), 1,2-dimyristoyl-sn-glycero-3-phosphocholine (DMPC), 1,2-dimyristoyl-rac-glycero-3-methoxy poly (ethyleneglycol)-2000, 1,2-dimyristoyl-sn-glycero-3-phosphoethanolamine-poly (ethyleneglycol)-2000, 1,2-distearoyl-sn-glycero-3-phosphoethanolamine poly (ethyleneglycol)-2000, and 1,2-dipalmitoyl-sn-glycero-3-phosphoethanolamine poly (ethyleneglycol)-2000.

12. The transfection agent according to claim 11, comprising at least one compound of general formula (I) in an amount of from 10 to 50 mol. %, and at least one helper lipid in an amount of from 50 to 90 mol. %.

13. The transfection agent according to claim 11, comprising at least one compound of general formula (I) in an amount of from 15 to 40 mol. %, cholesterol in an amount of from 30 to 55 mol. %, and at least one other helper lipid in an amount of from 20 to 50 mol. %; wherein the helper lipid is selected from the group comprising β-sitosterol, stigmastanol, campesterol, fucosterol, avenasterol, fecosterol, brassicasterol, ergosterol, 9,11-dehydroergosterol, 1,2-dioleoyl-sn-glycero-3-phosphoethanolamine (DOPE), 1,2-dioleoyl-sn-glycero-3-phosphocholine (DOPC), 1,2-distearoyl-sn-glycero-3-phosphocholine (DSPC), 1,2-dipalmitoyl-sn-glycero-3-phosphocholine (DPPC), 1,2-dimyristoyl-sn-glycero-3-phosphocholine (DMPC), 1,2-dimyristoyl-rac-glycero-3-methoxy poly (ethyleneglycol)-2000, 1,2-dimyristoyl-sn-glycero-3-phosphoethanolamine-poly (ethyleneglycol)-2000, 1,2-distearoyl-sn-glycero-3-phosphoethanolamine poly (ethyleneglycol)-2000, and 1,2-dipalmitoyl-sn-glycero-3-phosphoethanolamine poly (ethyleneglycol)-2000.

14. A transfection particle comprising at least one compound of general formula (I) according to claim 1, at least one nucleic acid and/or a part thereof and/or nucleic acid derivative; and also at least one helper lipid.

15. A method of administering a medicament comprising the compound of general formula (I) according to claim 1 for in vitro transfection of cells or tissues with nucleic acid and/or a part thereof and/or nucleic acid derivative.

16. A method of administering a medicament comprising the compound of general formula (I) according to claim 1 for silencing or activating chromosomal gene(s), silencing or activating immunogenes, inhibiting or activating signaling pathways, editing genome or transcriptome, or enabling the expression of the protein(s) encoded by a nucleic acid.

17. A method of administering a medicament comprising the compound of general formula (I) according to claim 1 for transfection of cells or tissues with nucleic acid and/or a part thereof and/or nucleic acid derivative in vivo, excluding the transfection of human embryos for industrial or commercial purposes and excluding the modification of a human germ line.

18. A method of administering a medicament comprising the compound of general formula (I) according to claim 1 for silencing or activating chromosomal gene(s), silencing or activating immunogenes, inhibiting or activating signaling pathways, editing genome or transcriptome, or enabling the expression of the protein(s) encoded by a nucleic acid or for a prophylactic vaccine or for cosmetic preparations in delivering an active ingredient to a site of action.

19. A method of administering a medicament comprising the compound of general formula (I) according to claim 1 for gene therapy.

20. The compound of general formula (I), according to claim 1 wherein all $R^1$ in the compound are different.

21. The compound of general formula (I), according to claim 1 wherein the compound of general formula (I) is selected from the group consisting of:

(3)

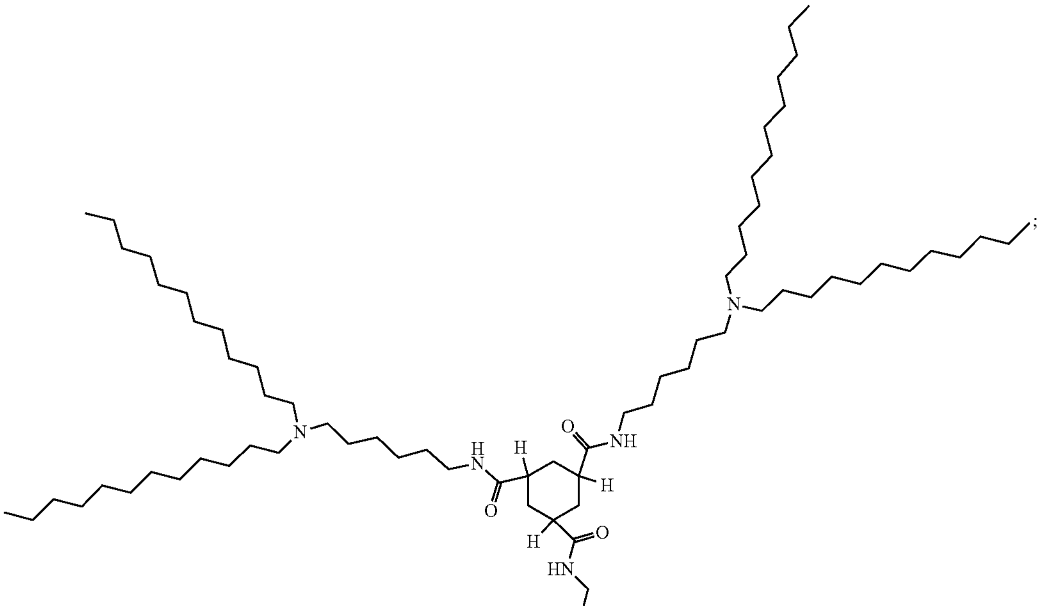

;

-continued
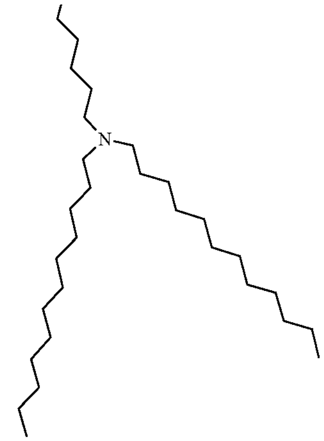
(7)
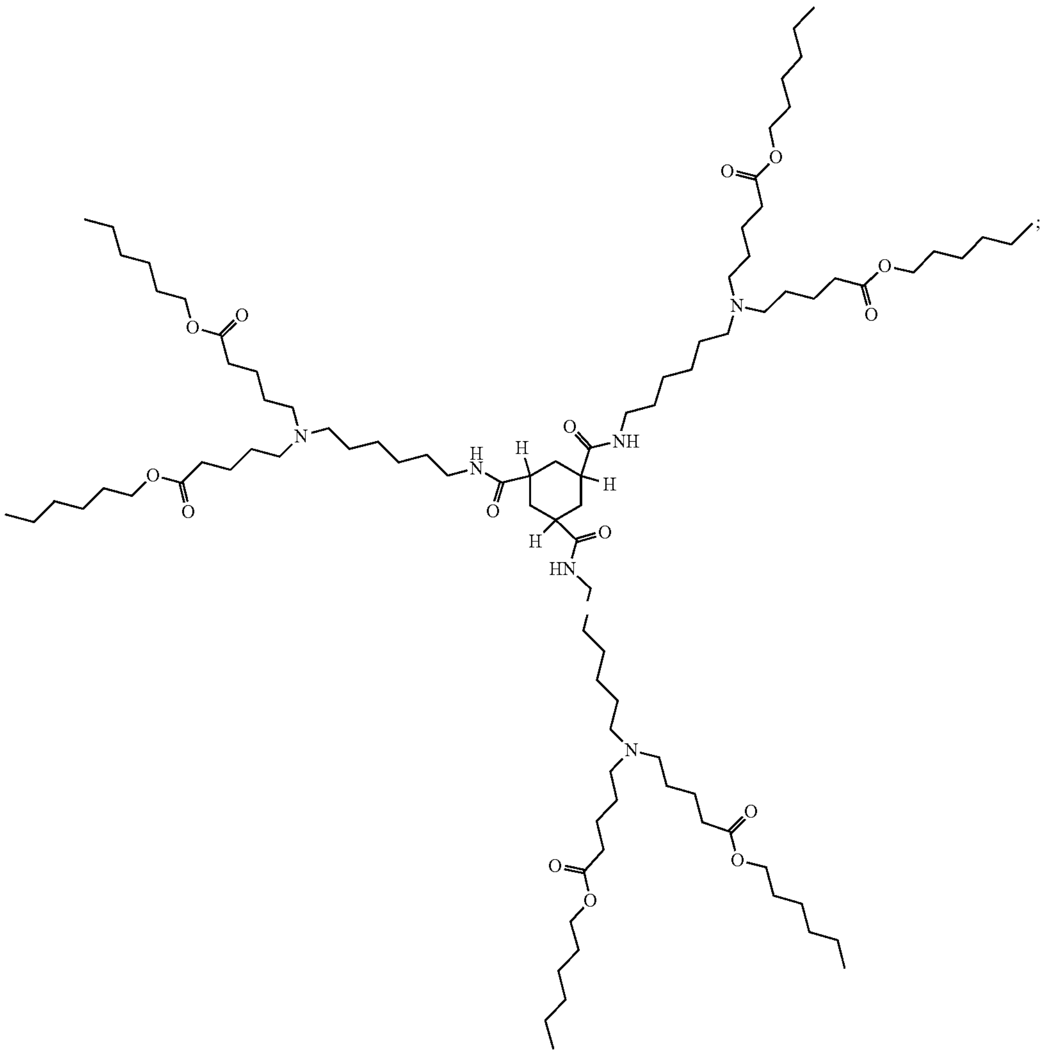
;

-continued
(8)
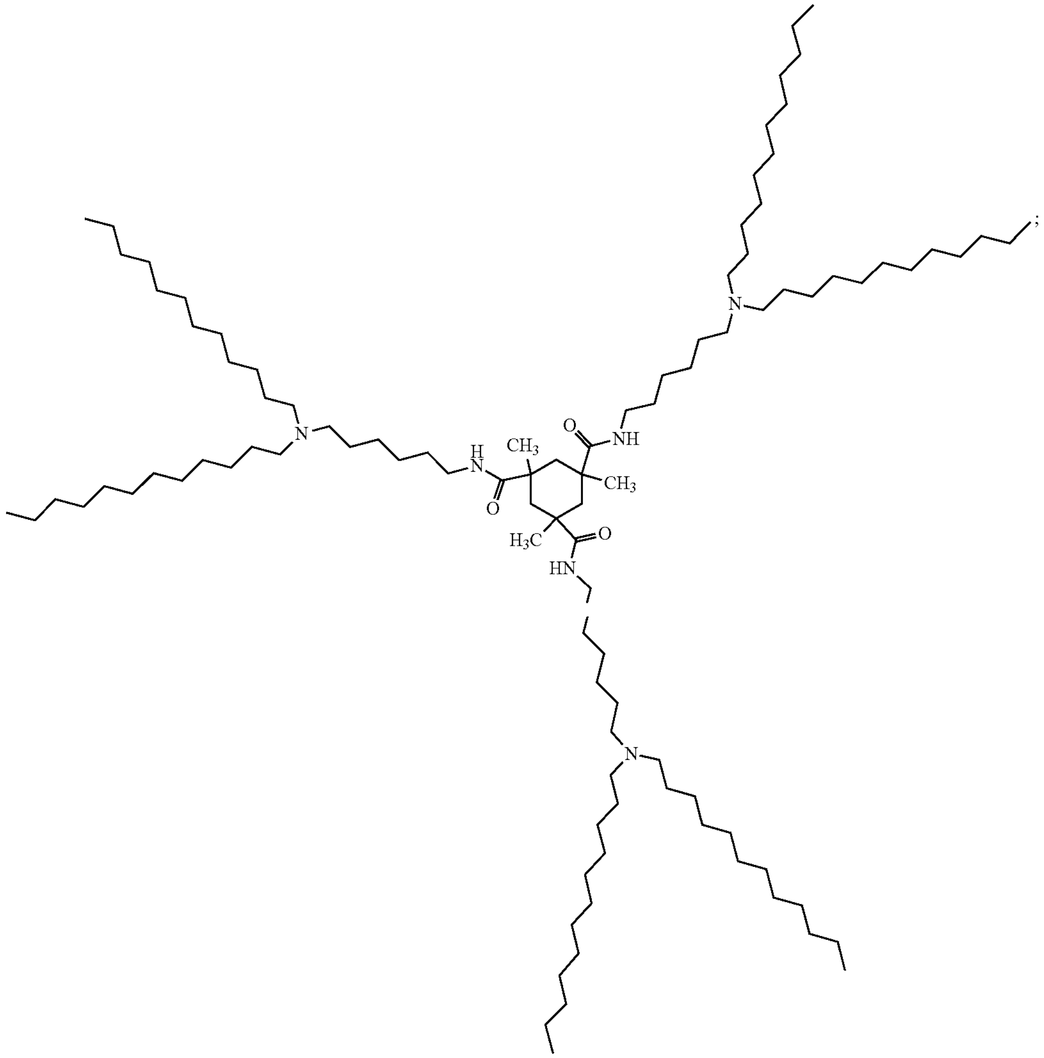
(11)
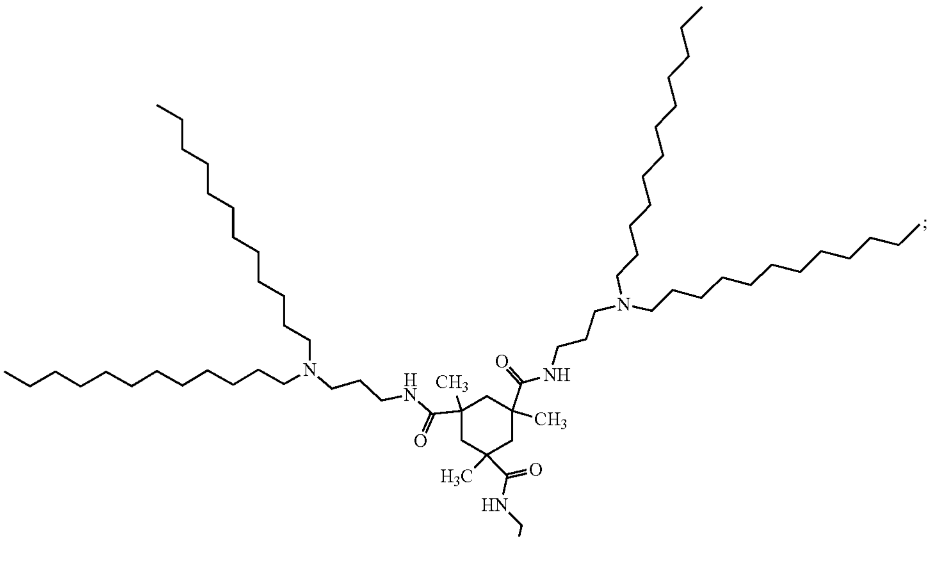

-continued
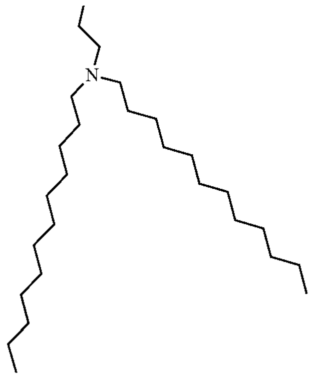
(15)
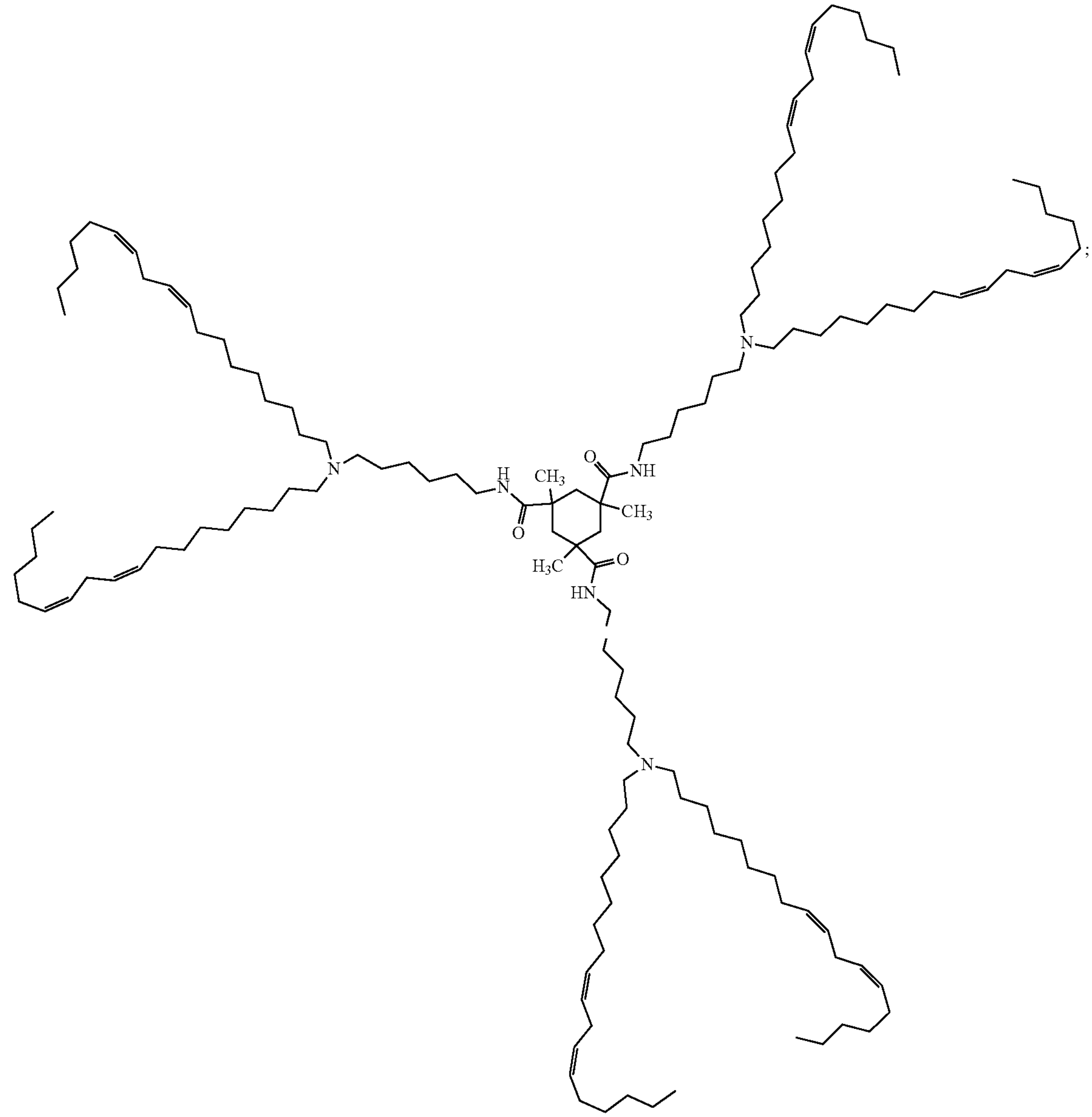
;

-continued
(19)
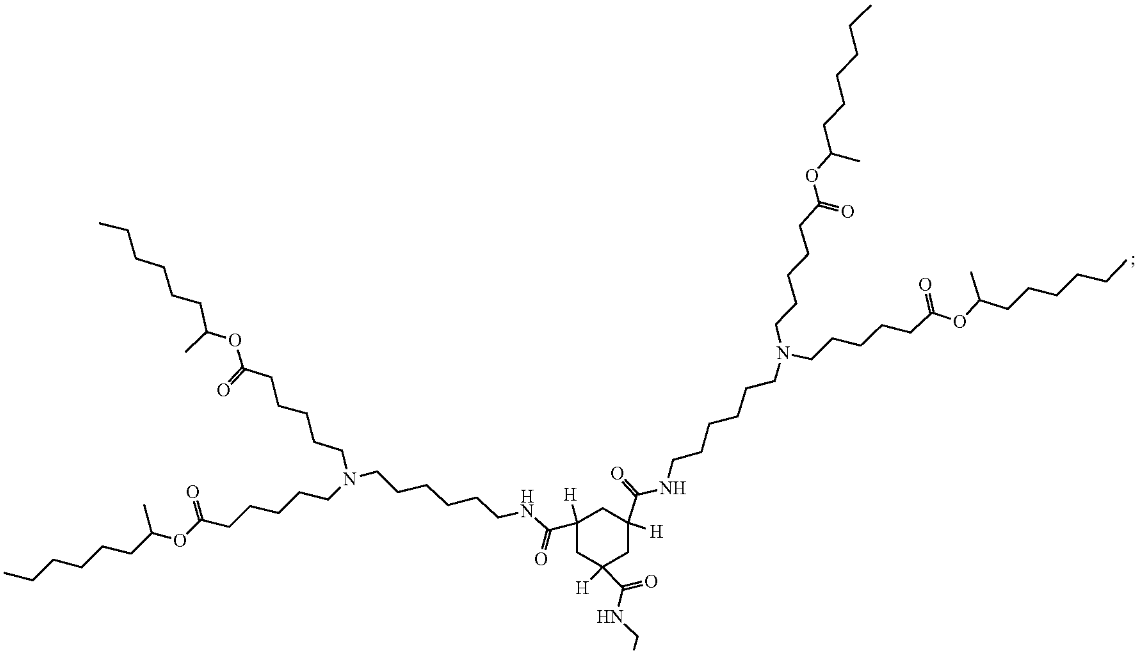
;
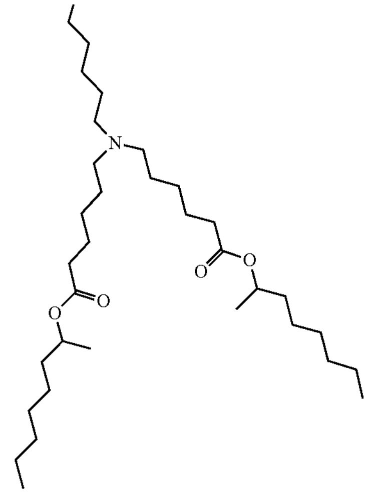

-continued
(23)
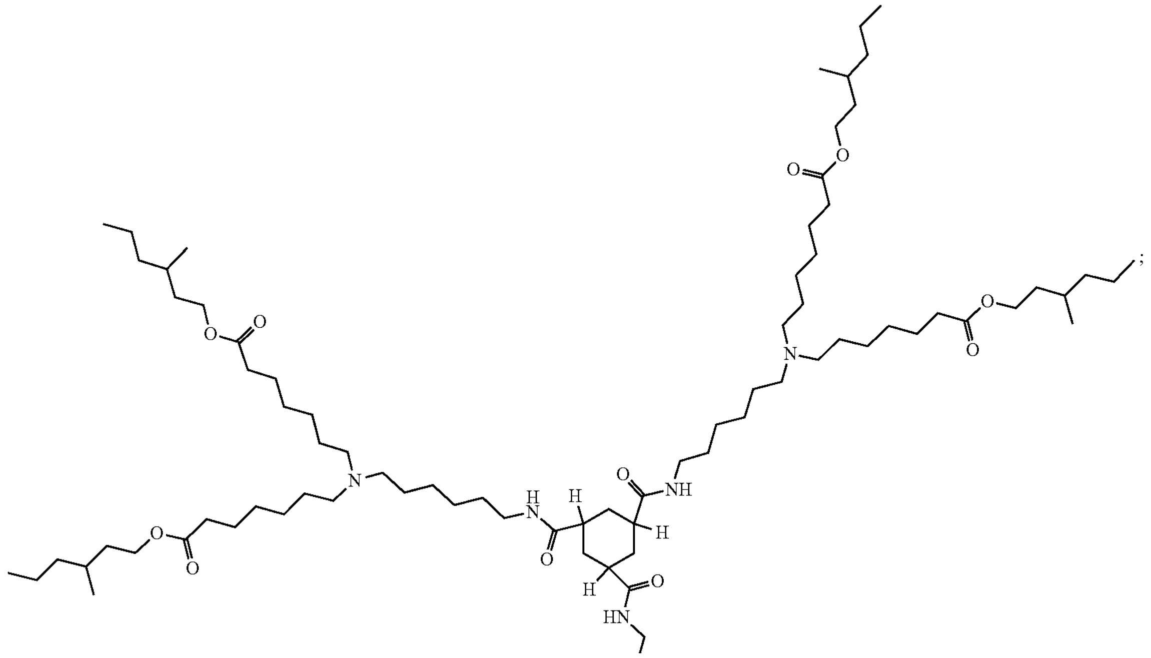
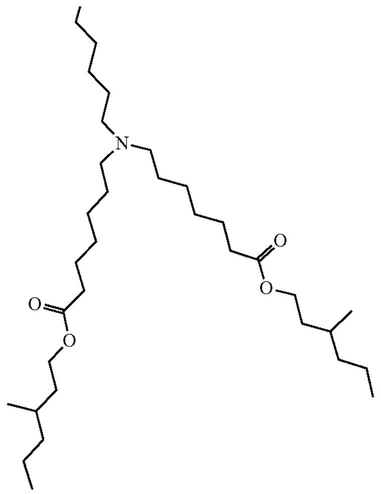

-continued
(27)
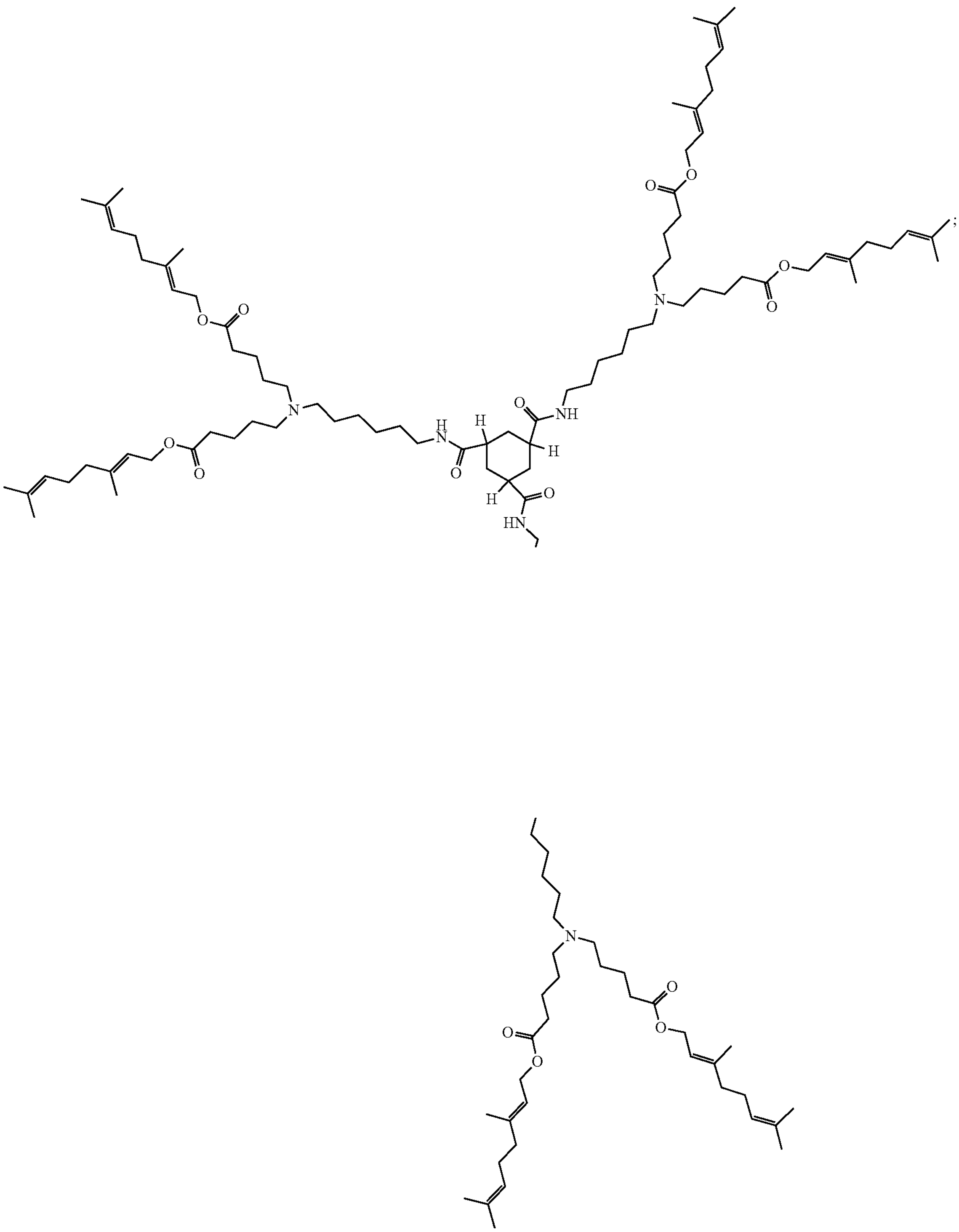
;

-continued
(31)
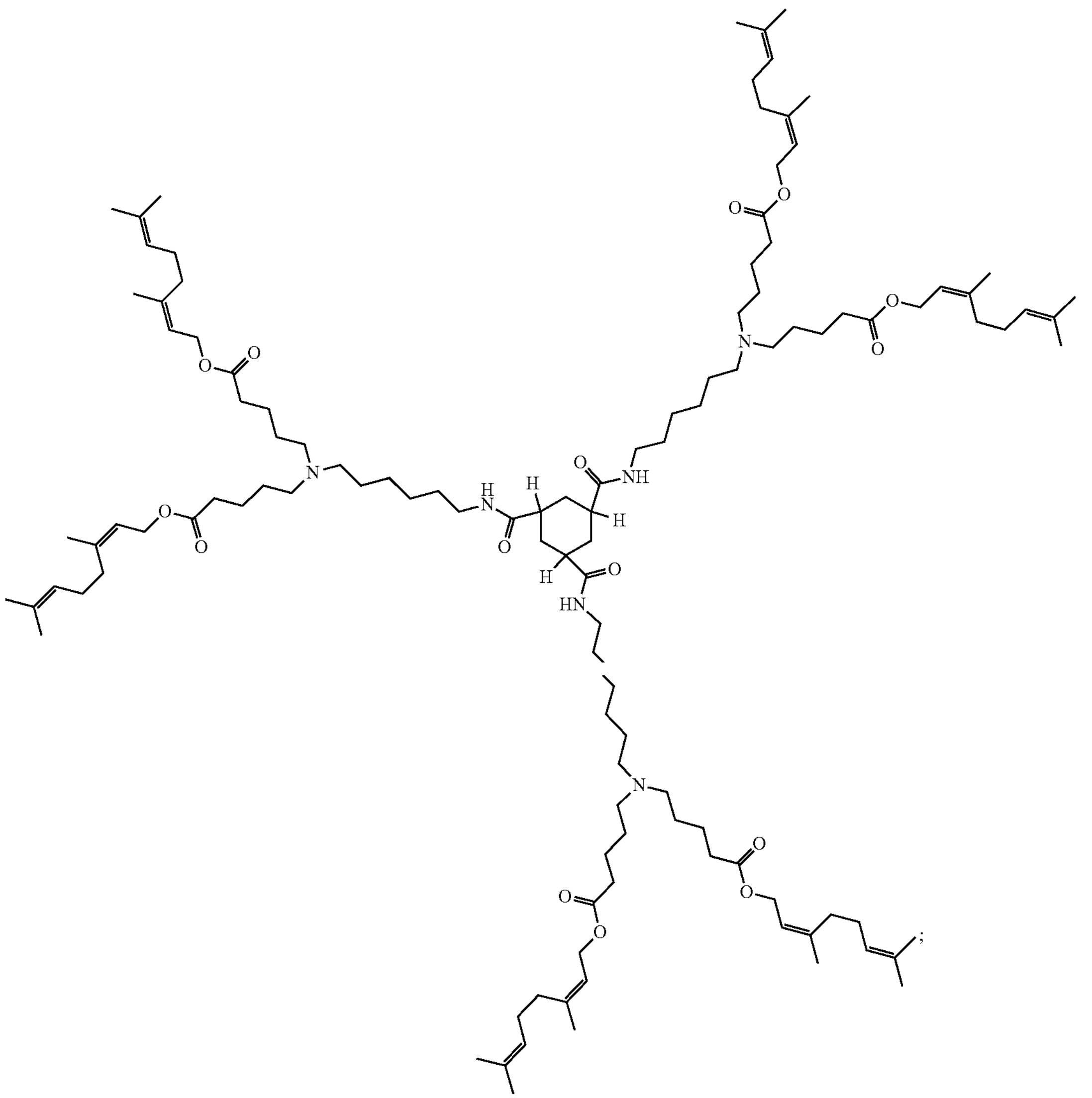
(32)
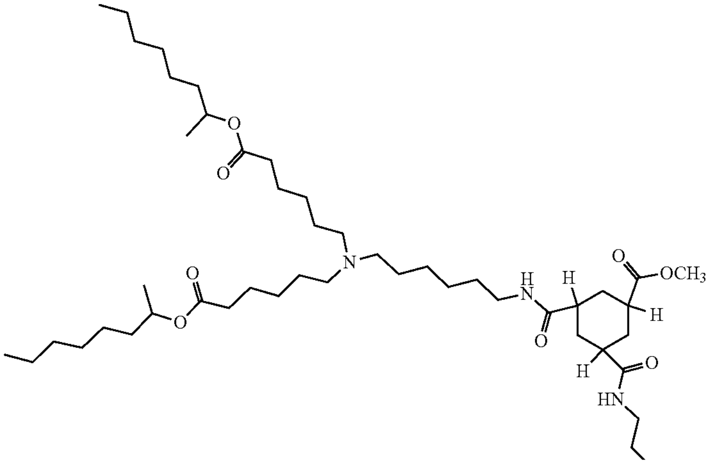

-continued
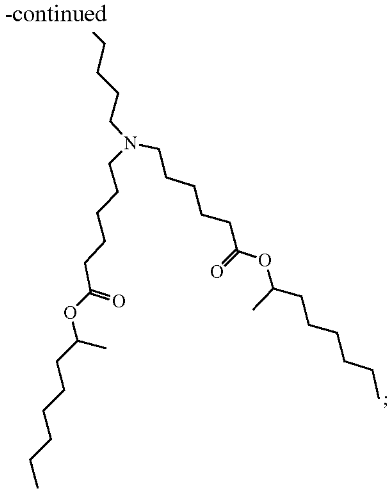
;
(33)
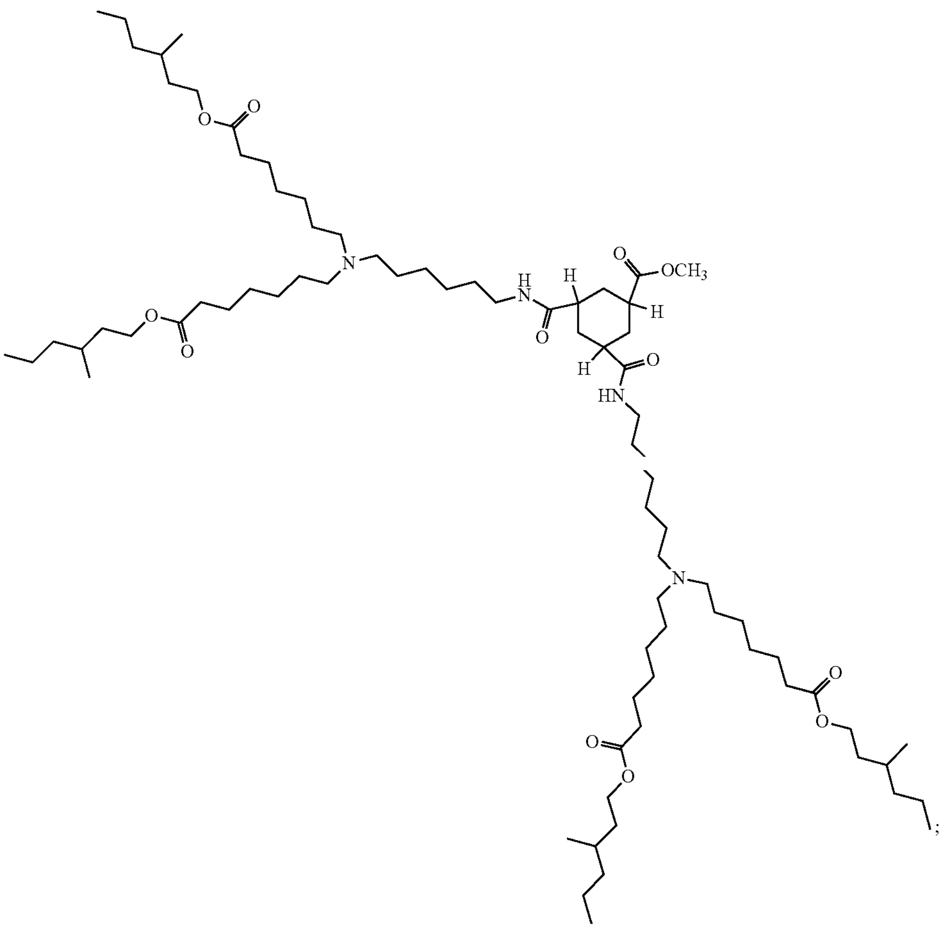
;

-continued
(35)
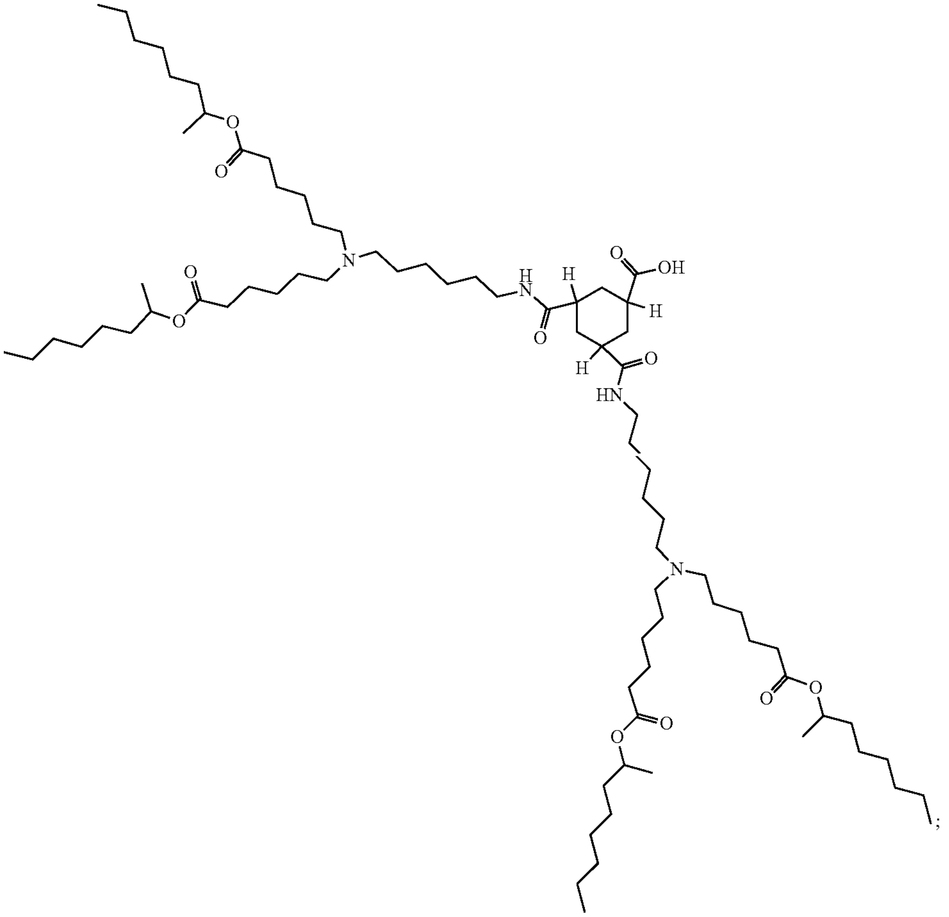
(36)
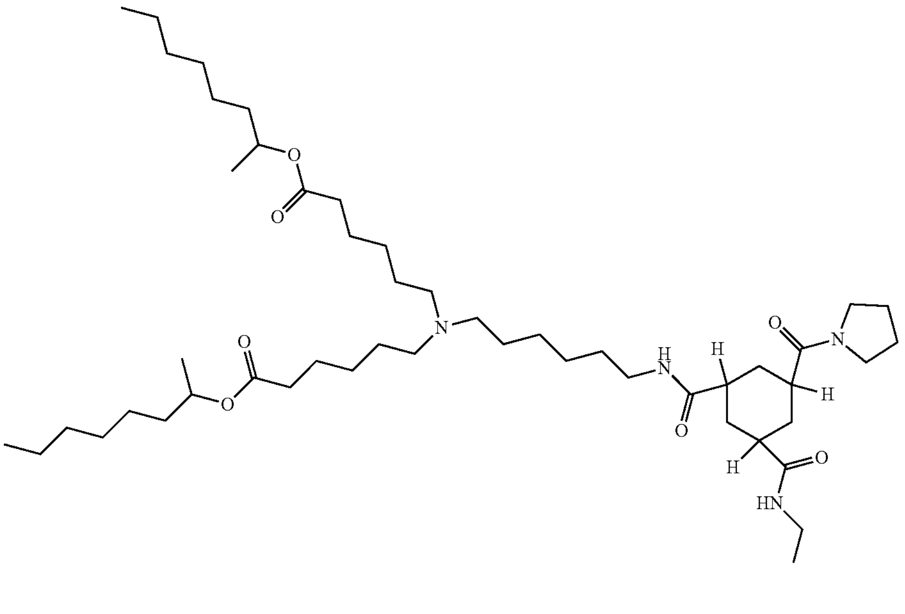

-continued
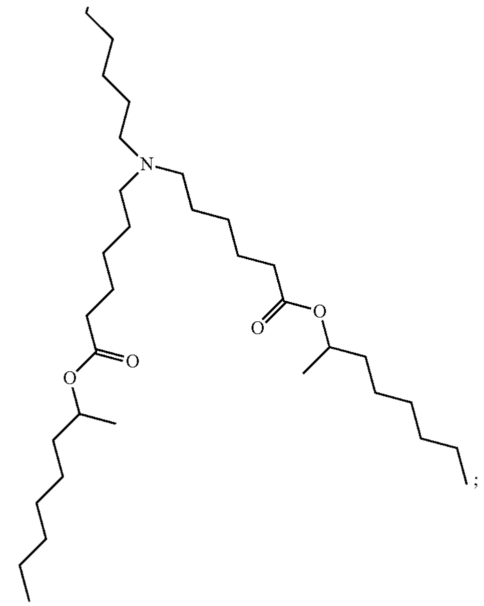
(40)
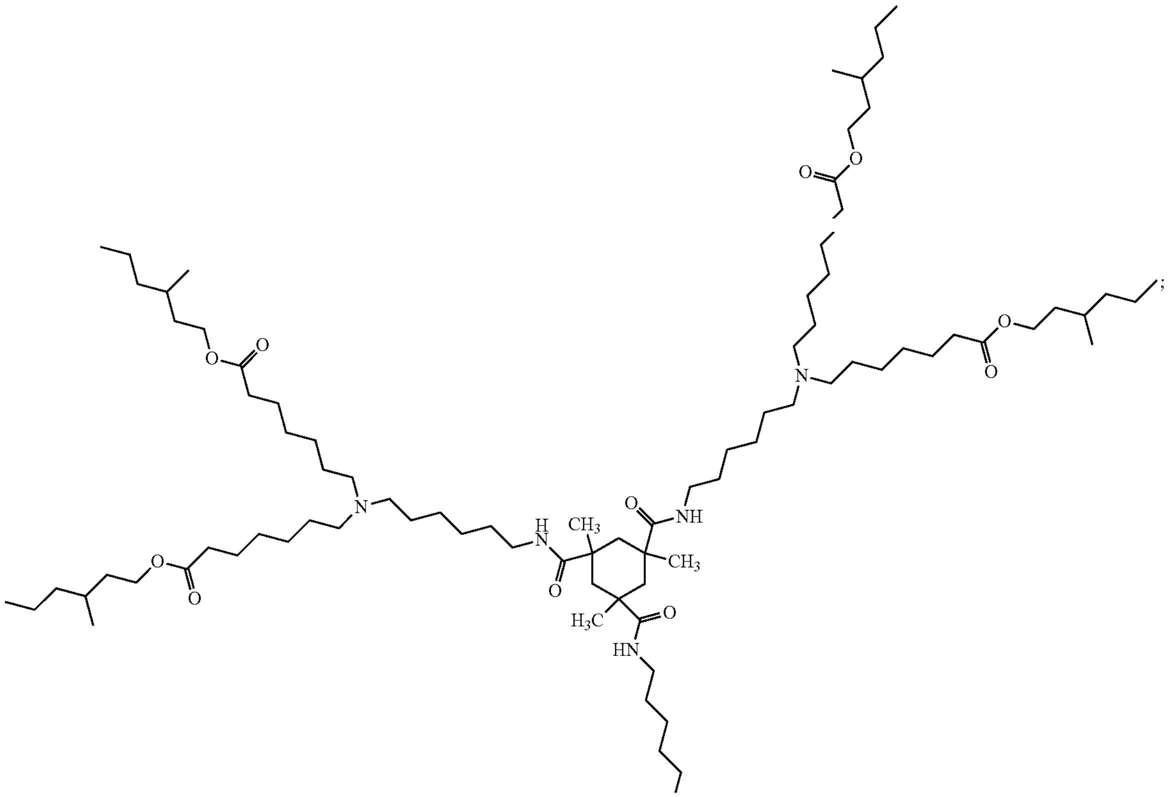

-continued
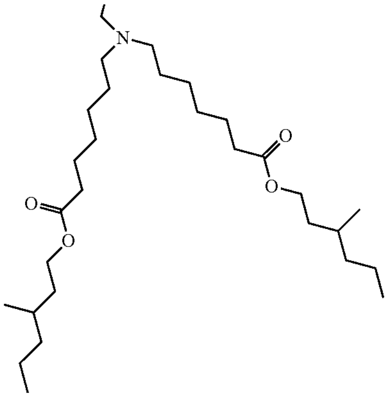
(41)
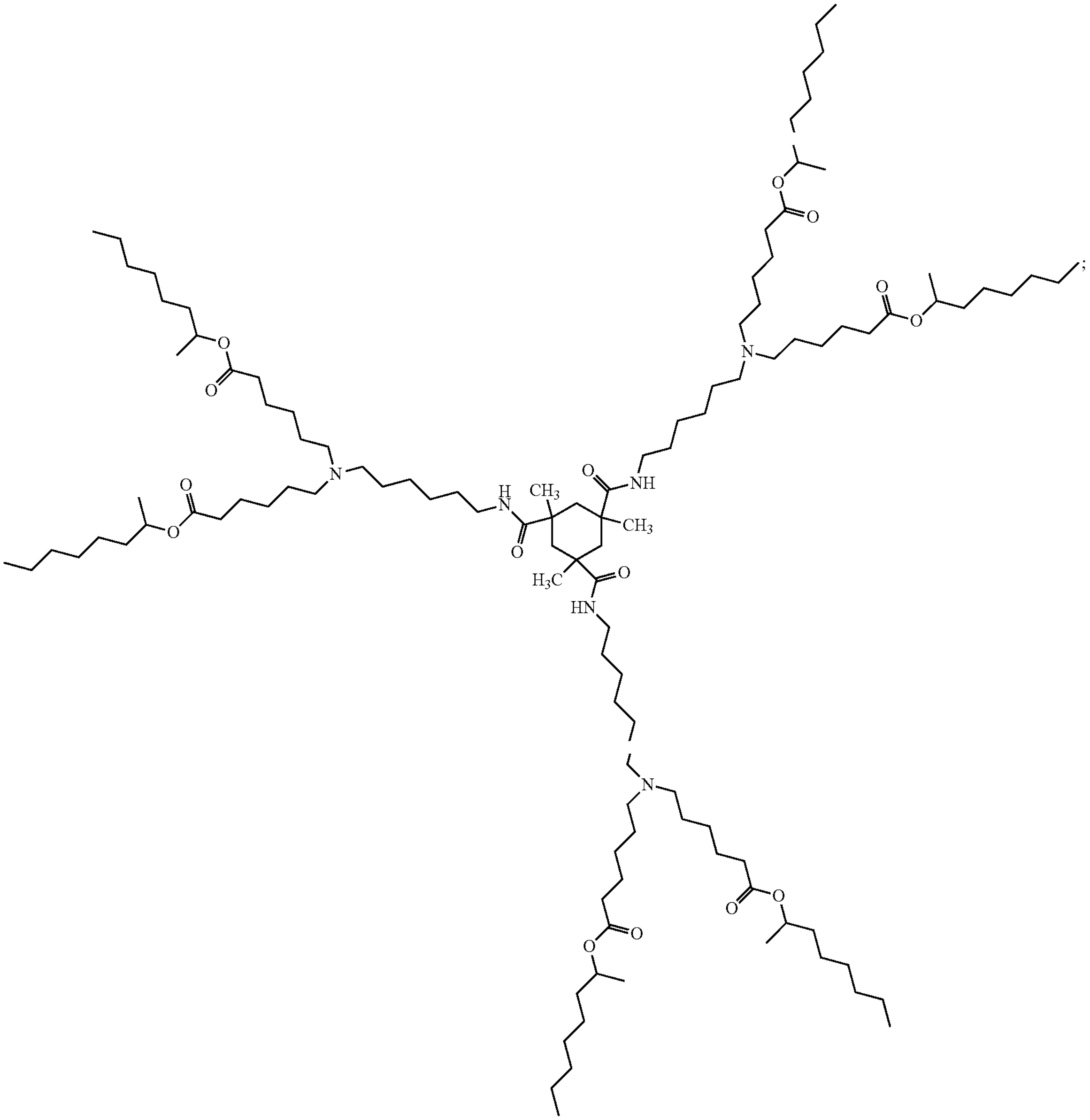

-continued
(42)
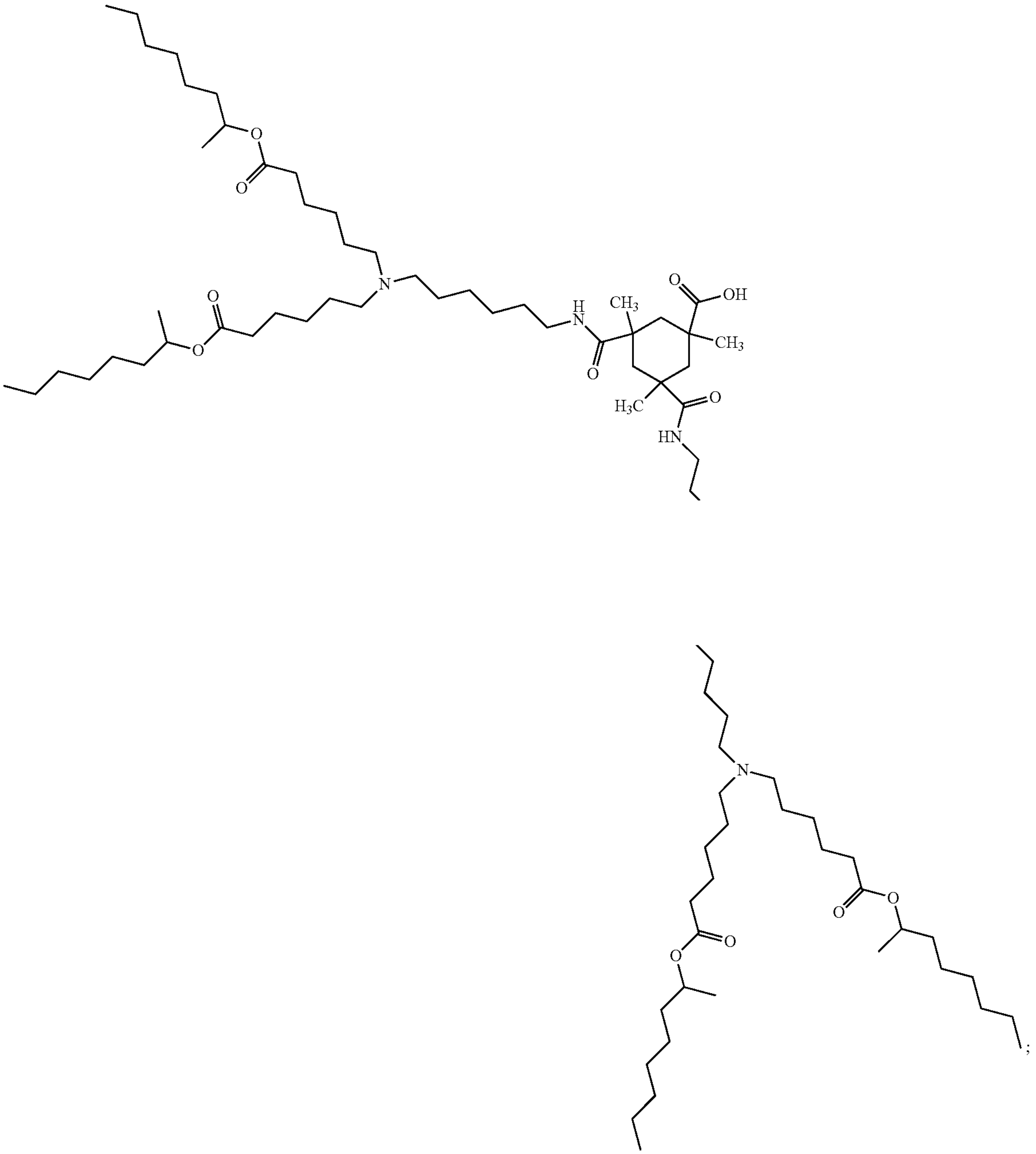
(47)
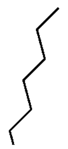

-continued
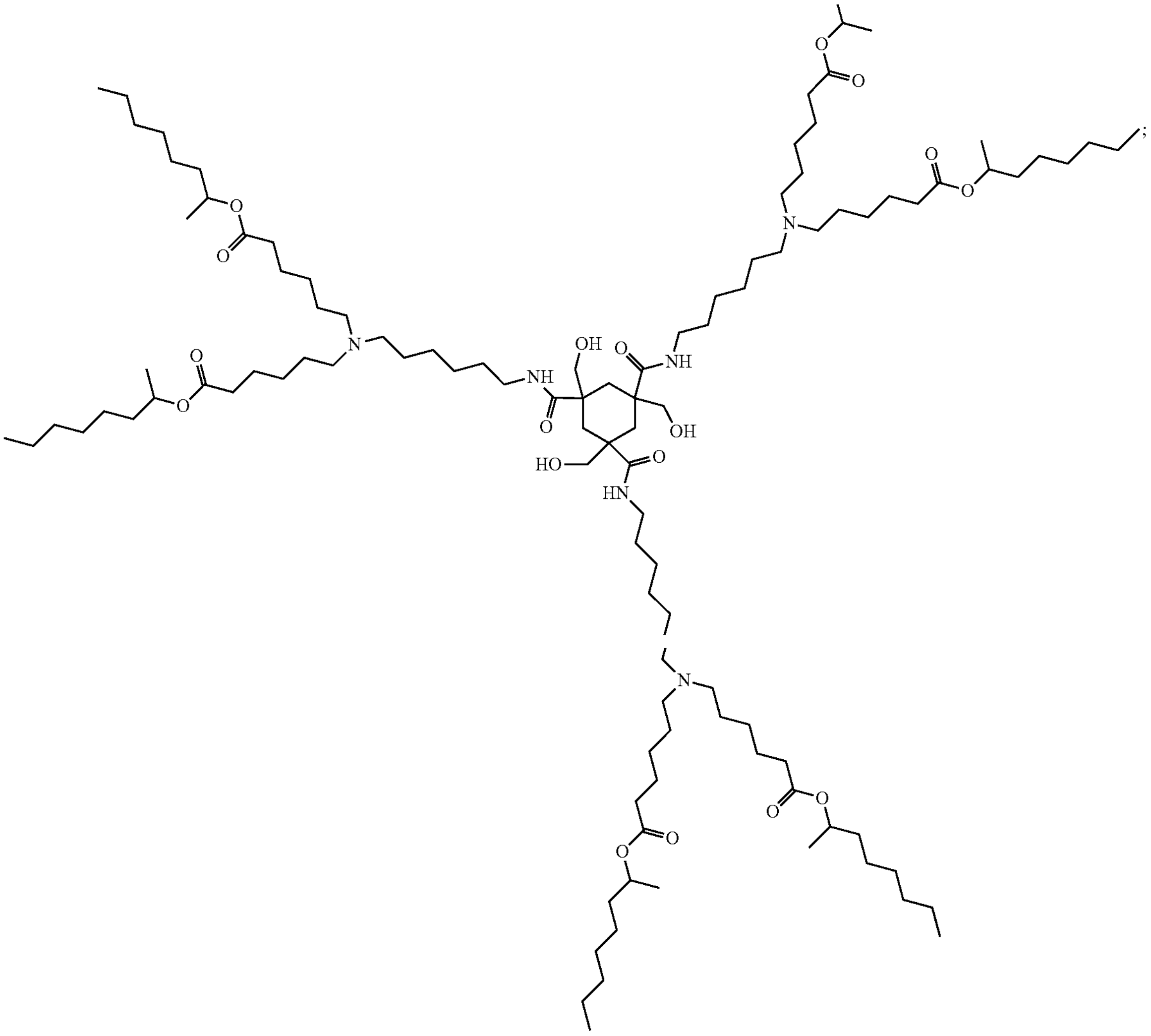
(48)
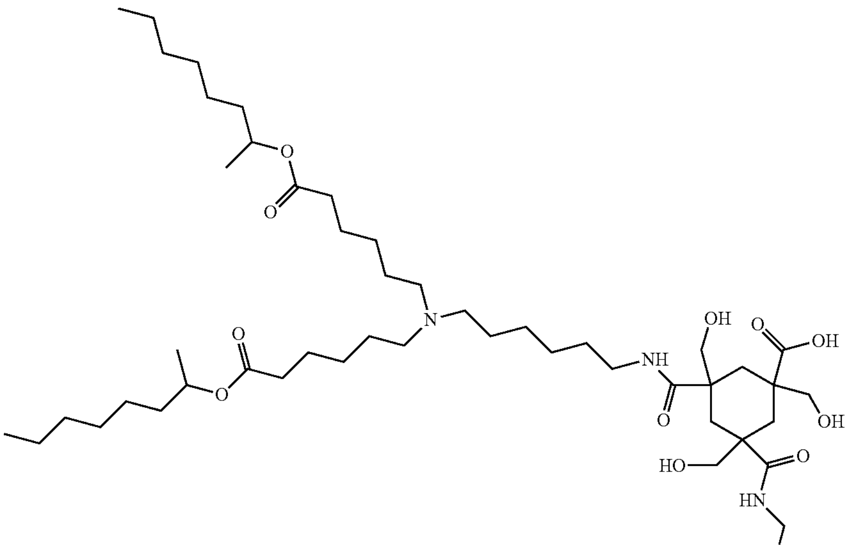

-continued
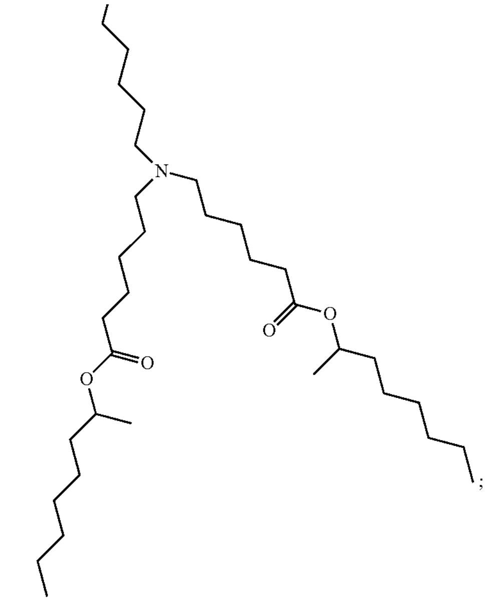
;
(50)
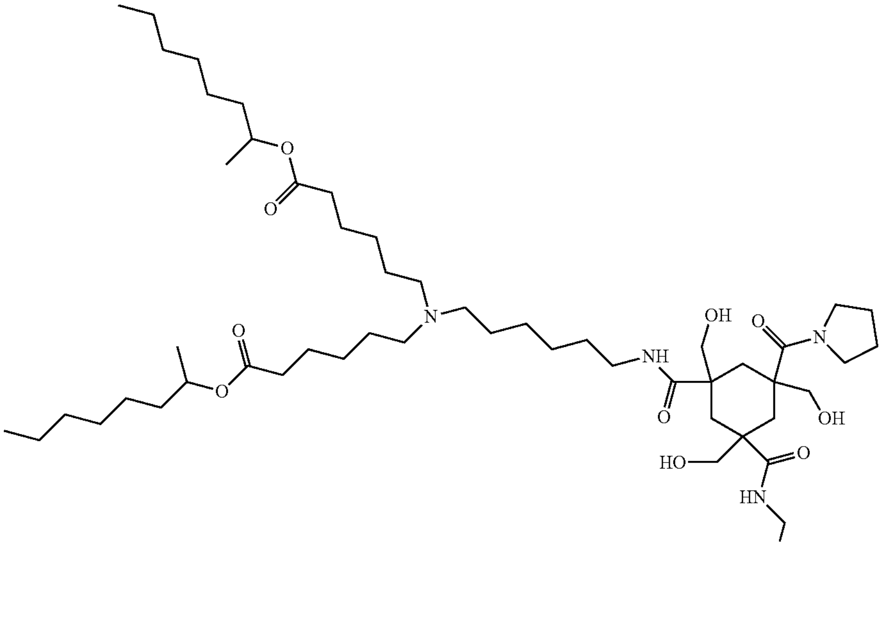

-continued
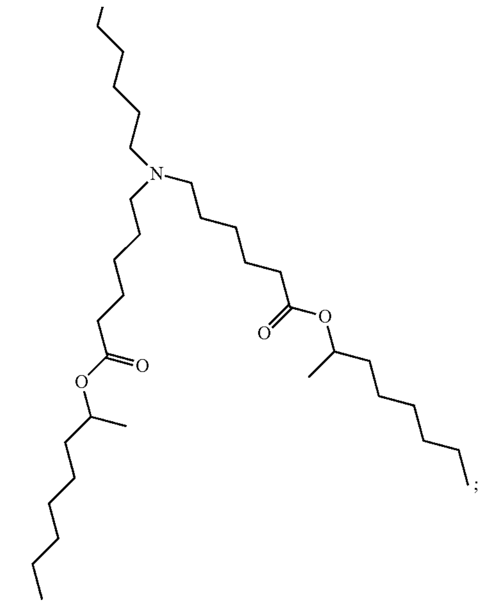
;
(52)
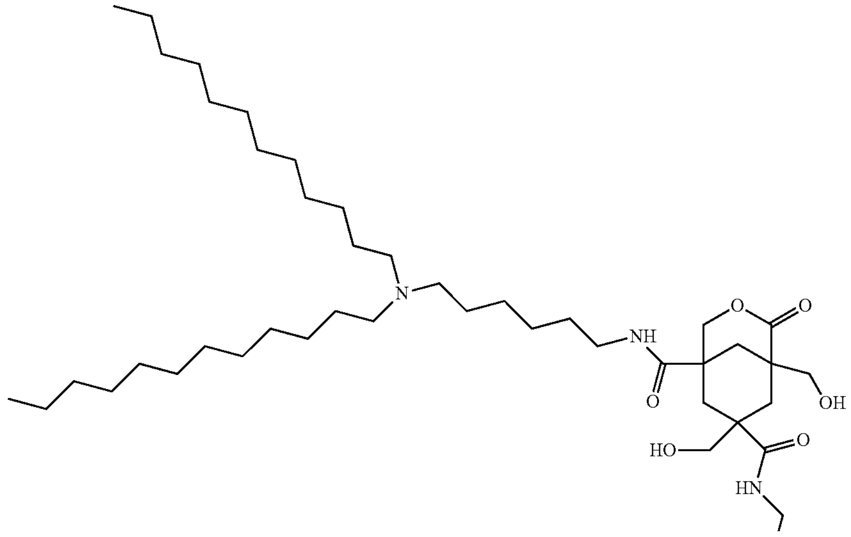

-continued
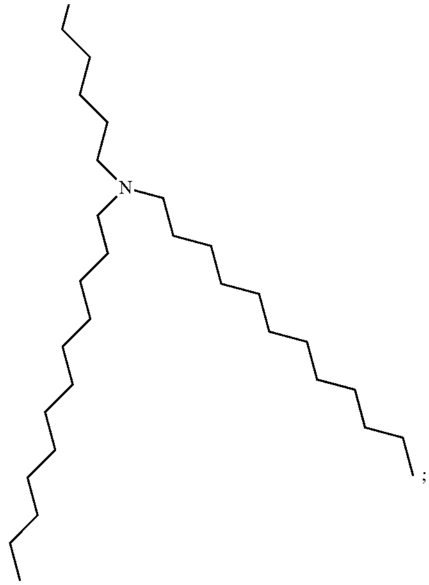
; and
(56)
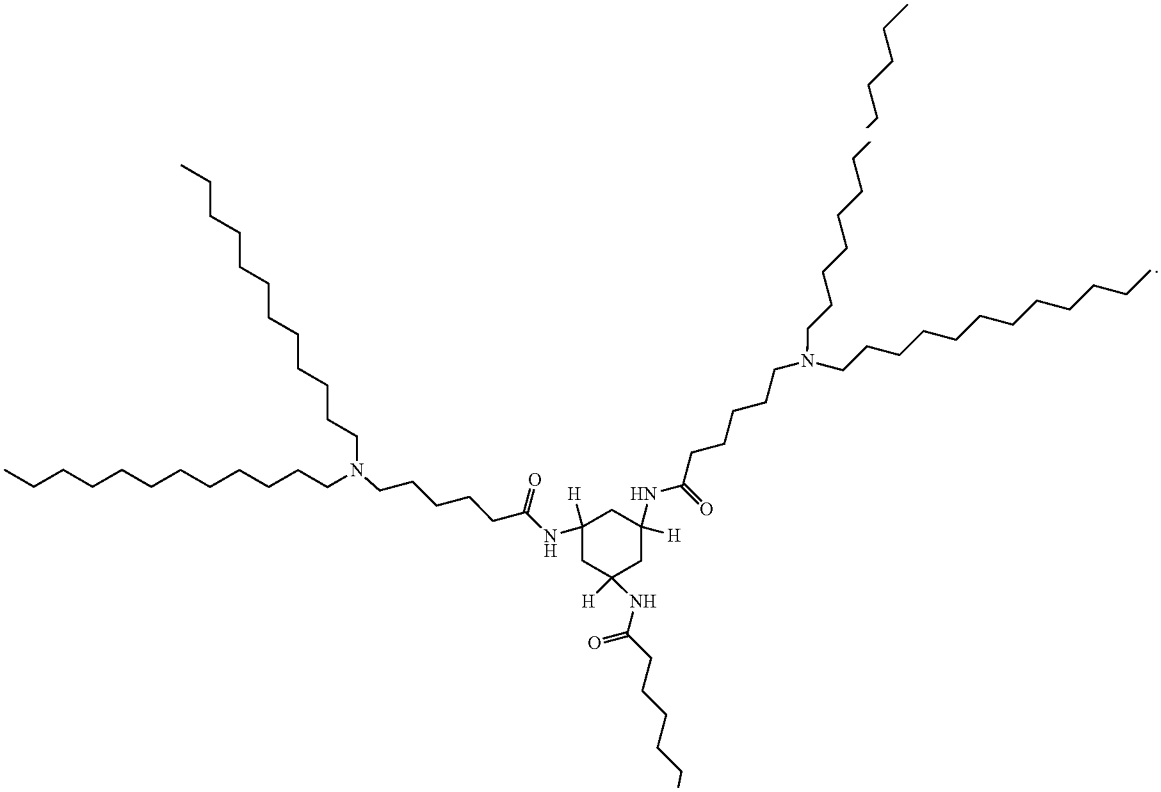
.

-continued
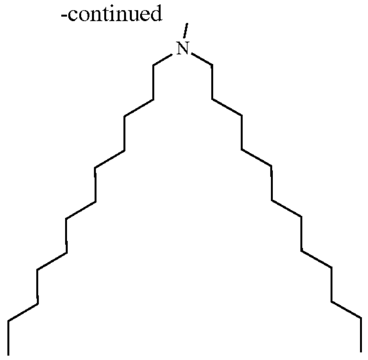
* * * * *

SEQUENCE LISTING

```
Sequence total quantity: 8
SEQ ID NO: 1           moltype = DNA  length = 23
FEATURE                Location/Qualifiers
source                 1..23
                       mol_type = other DNA
                       organism = synthetic construct
SEQUENCE: 1
atcaacatat ggtgagcgag ctg                                          23

SEQ ID NO: 2           moltype = DNA  length = 26
FEATURE                Location/Qualifiers
source                 1..26
                       mol_type = other DNA
                       organism = synthetic construct
SEQUENCE: 2
aagaattcct atcatctgtg ccccag                                       26

SEQ ID NO: 3           moltype = DNA  length = 21
FEATURE                Location/Qualifiers
source                 1..21
                       mol_type = other DNA
                       organism = synthetic construct
SEQUENCE: 3
cgagaggagg gtctcaaaga g                                            21

SEQ ID NO: 4           moltype = DNA  length = 20
FEATURE                Location/Qualifiers
source                 1..20
                       mol_type = other DNA
                       organism = synthetic construct
SEQUENCE: 4
atttcgggaa ggctgctgtc                                              20

SEQ ID NO: 5           moltype = DNA  length = 20
FEATURE                Location/Qualifiers
source                 1..20
                       mol_type = other DNA
                       organism = synthetic construct
SEQUENCE: 5
aatcccatca ccatcttcca                                              20

SEQ ID NO: 6           moltype = DNA  length = 20
FEATURE                Location/Qualifiers
source                 1..20
                       mol_type = other DNA
                       organism = synthetic construct
SEQUENCE: 6
tggactccac gacgtactca                                              20

SEQ ID NO: 7           moltype = DNA  length = 21
FEATURE                Location/Qualifiers
source                 1..21
                       mol_type = other DNA
                       organism = synthetic construct
SEQUENCE: 7
aacgtgctgg ttattgtgct g                                            21

SEQ ID NO: 8           moltype = DNA  length = 20
FEATURE                Location/Qualifiers
source                 1..20
                       mol_type = other DNA
                       organism = synthetic construct
SEQUENCE: 8
aagtcgtgct gcttcatgtg                                              20
```